US007947286B2

(12) United States Patent
Lehrer et al.

(10) Patent No.: US 7,947,286 B2

(45) Date of Patent: May 24, 2011

(54) DROSOPHILA CELL LINES PRODUCING RECOMBINANT SECRETABLE FILOVIRUS SURFACE GLYCOPROTEINS LACKING THE MEMBRANE SPANNING DOMAIN

(75) Inventors: Axel Thomas Lehrer, Honolulu, HI (US); David Edward Clements, Honolulu, HI (US); Tom Humphreys, Honolulu, HI (US)

(73) Assignee: PanThera Biopharma LLC, Aiea, HI (US)

( * ) Notice: Subject to any disclaimer, the term of this patent is extended or adjusted under 35 U.S.C. 154(b) by 126 days.

(21) Appl. No.: 11/545,093

(22) Filed: Oct. 5, 2006

(65) Prior Publication Data

US 2007/0082011 A1 Apr. 12, 2007

Related U.S. Application Data

(60) Provisional application No. 60/724,747, filed on Oct. 7, 2005.

(51) Int. Cl.
*A61K 39/12* (2006.01)
*C12P 21/04* (2006.01)

(52) U.S. Cl. .................................... 424/204.1; 435/70.1

(58) Field of Classification Search ........................ None
See application file for complete search history.

(56) References Cited

U.S. PATENT DOCUMENTS

| | | | | |
|---|---|---|---|---|
| 6,136,561 | A * | 10/2000 | Ivy et al. | 435/69.3 |
| 6,200,959 | B1 * | 3/2001 | Haynes et al. | 514/44 |
| 6,517,842 | B1 | 2/2003 | Hevey | |
| 6,544,780 | B1 | 4/2003 | Wang | |
| 6,964,762 | B2 | 11/2005 | Wang | |
| 6,984,504 | B2 | 1/2006 | Hart | |
| 7,090,852 | B2 | 8/2006 | Hevey | |
| 7,094,598 | B2 | 8/2006 | Nabel | |
| 7,267,823 | B2 | 9/2007 | Hart | |
| 2006/0099225 | A1 | 5/2006 | Bavari | |
| 2006/0251681 | A1 | 11/2006 | Heyey | |

FOREIGN PATENT DOCUMENTS

| | | | |
|---|---|---|---|
| WO | WO 00/00616 | A3 | 1/2000 |
| WO | WO 03/092582 | A2 | 11/2003 |
| WO | WO 2005/063798 | A1 | 7/2005 |
| WO | WO 2006/037038 | A1 | 4/2006 |

OTHER PUBLICATIONS

Muerhoff, A. S., et al., 2004, Enzyme-linked immunosorbent assays using recombinant envelope protein expressed in COS-1 and Drosophila S2 cells for detection of West Nile Virus immunoglobulin M in serum or cerebrospinal fluid, Clin. Diag. Lab. Immunol. 11(4):651-657.*

Wilson JA, et al. 2000. "Epitopes involved in antibody-mediated protection from Ebola virus." Science.; 287(5458): 1664-1666.

Wilson JA, et al. 2001. "Vaccine potential of Ebola virus VP24, VP30, VP35, and VP40 proteins." Virology; 286(2): 384-390.

Xu L, et al. 1998. "Immunization for Ebola virus infection." Nat Med.; 4(1): 37-42.

Bukreyev et al. (1995) "The complete nucleotide sequence of the Popp (1967) strain of Marburg virus: a comparison with the Musoke (1980) strain," *Archives of Virology*, 140:1589-1600.

Dolnik et al. (2004) "Ectodomain shedding of the glycoprotein GP of Ebola virus," *EMBO J.*, 23:2175-2184.

Geisbert et al. (2002) "Evaluation in Nonhuman Primates of Vaccines against Ebola Virus," *Emerg Infect Dis.*, 8(5): 503-507.

GenBank Accession No. NC 002549, "Zaire ebolavirus, complete genome," Dec. 8, 2008.

Hart (2003) "Vaccine research efforts for filoviruses," *Int J Parasitol.*, 33(5-6): 583-595.

Hevey et al. (1997) "Antigenicity and vaccine potential of Marburg virus glycoprotein expressed by baculovirus recombinants," *Virology*, 239(1): 206-216.

Hevey et al. (2002) "Marburg virus vaccines: comparing classical and new approaches," *Vaccine*, 20(3-4): 586-593.

Mellquist-Riemenschneider et al. (2003) "Comparison of the protective efficacy of DNA and baculovirus-derived protein vaccines for EBOLA virus in guinea pigs," *Virus Res.*, 92(2): 187-193.

Sanchez et al. (2005) "Complete genome sequence of an Ebola virus (Sudan species) responsible for a 2000 outbreak of human disease in Uganda," *Virus Research*, 113:16-25.

Swenson et al. (2005) "Virus-like particles exhibit potential as a pan-filovirus vaccine for both Ebola and Marburg viral infections," *Vaccine*, 23(23): 3033-3042.

Volchkov et al. (1998) "Processing of the Ebola virus glycoprotein by the proprotein convertase furin," *PNAS*, 95(10): 5762-5767.

Volchkov et al. (1998) "Release of Viral Glycoproteins during Ebola Virus Infection" *Virology*, 245(1): 110-119.

Wahl-Jensen et al. (2005) "Effects of Ebola Virus Glycoproteins on Endothelial Cell Activation and Barrier Function" *J. Virol.*, 79(16): 10442-10450.

Warfield et al. (2003) "Ebola virus-like particles protect from lethal Ebola virus infection." *PNAS*, 26(100): 15889-15894.

Warfield et al. (2004) "Marburg virus-like particles protect guinea pigs from lethal Marburg virus infection," *Vaccine*. 22(25-26): 3495-3502.

Will et al. (1993) "Marburg virus gene 4 encodes the virion membrane protein, a type I transmembrane glycoprotein," *J. Virol.*, 67(3):1203-1210.

(Continued)

*Primary Examiner* — Jeffrey S Parkin

(74) *Attorney, Agent, or Firm* — Quine Intellectual Property Law Group, P.C.; Paul Littlepage

(57) ABSTRACT

Filovirus subunit protein immunogens are produced using a recombinant expression system and combined with one or more adjuvants in immunogenic formulations. The subunit proteins include GP95, GP-FL, VP40, VP24, and NP derived from Ebola Virus and Marburg Virus. Adjuvants include saponins, emulsions, alum, and dipeptidyl peptidase inhibitors. The disclosed immunogenic formulations are effective in inducing strong antibody responses directed against individual Filovirus proteins and intact Filovirus particles as well as stimulating cell-mediated immune responses to the Filoviruses.

14 Claims, 6 Drawing Sheets

OTHER PUBLICATIONS

Wilson et al. (2000) "Epitopes involved in antibody-mediated protection from Ebola virus," *Science*, 287(5458): 1664-1666.

Wilson et al. (2001) "Vaccine potential of Ebola virus VP24, VP30, VP35, and VP40 proteins," *Virology*, 286(2): 384-390.

Xu et al. (1998) "Immunization for Ebola virus infection," *Nat Med*. 4(1): 37-42.

Alazard-Dany et al. (2006) "Ebola virus glycoprotein GP is not cytotoxic when expressed constitutively at a moderate level," J. General Virol., 87:1247-1257.

Han (2007) "Permeabilization of the plasma membrane by Ebola virus GP2," Virus Genes, 34(3):273-281.

Marzi et al. (2006) "Modulation of virion incorporation of Ebolavirus glycoprotein: effects on attachment, cellular entry and neutralization," Virology, 352:345-356.

Sáez-Cirión et al. (2003) "Pre-transmembrane sequence of Ebola glycoprotein interfacial hydroprobicity distribution and interaction with membranes," FEBS Letters, 533:47-53.

Simmons et al. (2002) "Ebola virus glycoproteins induce global surface protein down-modulation and looss of cell adherence," J. Virology, 76(5):2518-2528.

Sullivan et al. (2003) "Ebola virus pathogenesis: implications for vaccines and therapies," J. Virology, 77(18):9733-9737.

Takada et al. (2000) "Downregulation of β1 integrins by Ebola virus glycoprotein: implication for virus entry," Virology, 278:20-26.

Volchkov et al. (2001) "Recovery of infectious Ebola virus from complementary DNA: RNA editing of the GP gene and viral cytotoxicity," Science, 291:1965-1969.

Watanabe et al. (2000) "Functional importance of the coiled-coil of the Ebola virus glycoprotein," J. Virology:10194-10201.

Yang et al. (1998) "Distinct cellular interactions of secreted and transmembrane Ebola virus glycoproteins," Science, 279:1034-1037.

Yang et al. (2000) "Identification of the Ebola virus glycoprotein as the main viral determinant of vascular cell cytotoxicity and injury," Nature Medicine, 6(8)886-889.

* cited by examiner

Figure 1 – Schematic structure of Ebola virus particle (from Feldmann and Kiley 1999)

Figure 2 – Expression of Ebola VP40, VP24 and GP documented on 12% SDS-PAGE

Figure 3: SDS-PAGE analysis of GP batches

Figure 4: SDS-PAGE analysis of the VP40 batches
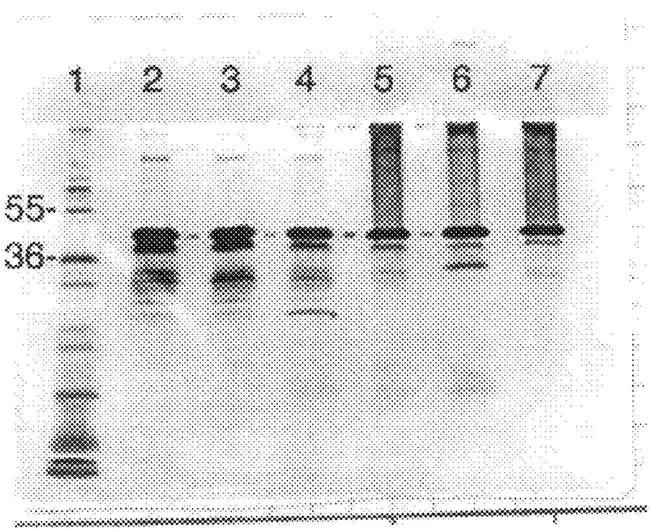
Figure 5: SDS-PAGE analysis of purified VP24
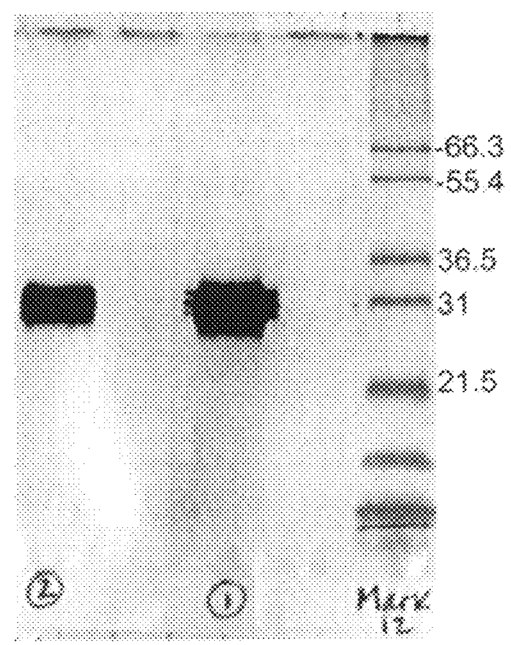

Figures 6, 7:
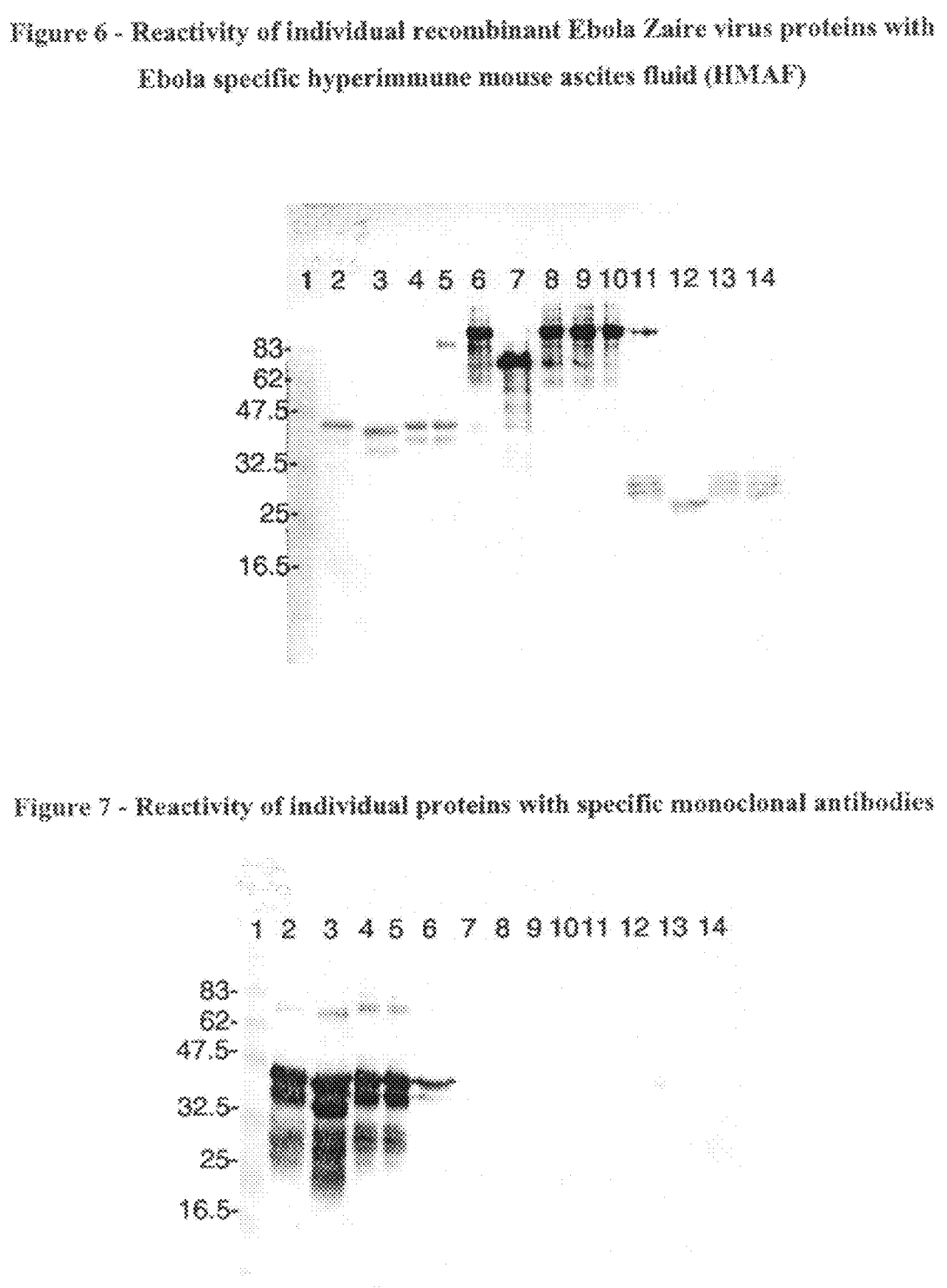

Figure 6 - Reactivity of individual recombinant Ebola Zaire virus proteins with Ebola specific hyperimmune mouse ascites fluid (HMAF)

1 2 3 4 5 6 7 8 9 10 11 12 13 14

83-
62-
47.5-
32.5-
25-
16.5-

Figure 7 - Reactivity of individual proteins with specific monoclonal antibodies 1 2 3 4 5 6 7 8 9 10 11 12 13 14

83-
62-
47.5-
32.5-
25-
16.5-

Figure 8- Reactivity of individual proteins with specific monoclonal antibodies
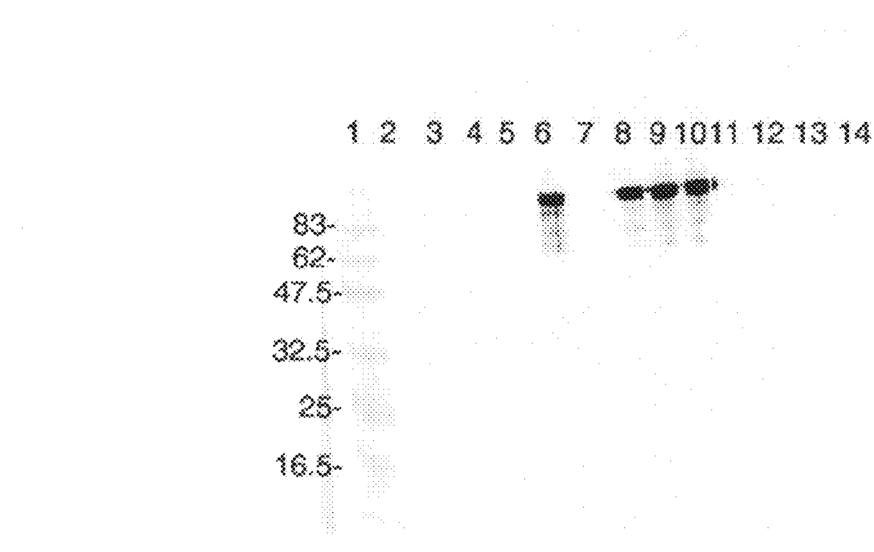
Figure 9 - Reactivity of individual proteins with specific monoclonal antibodies
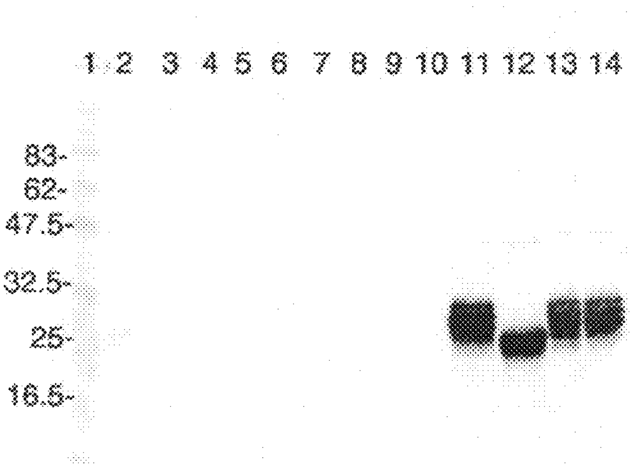

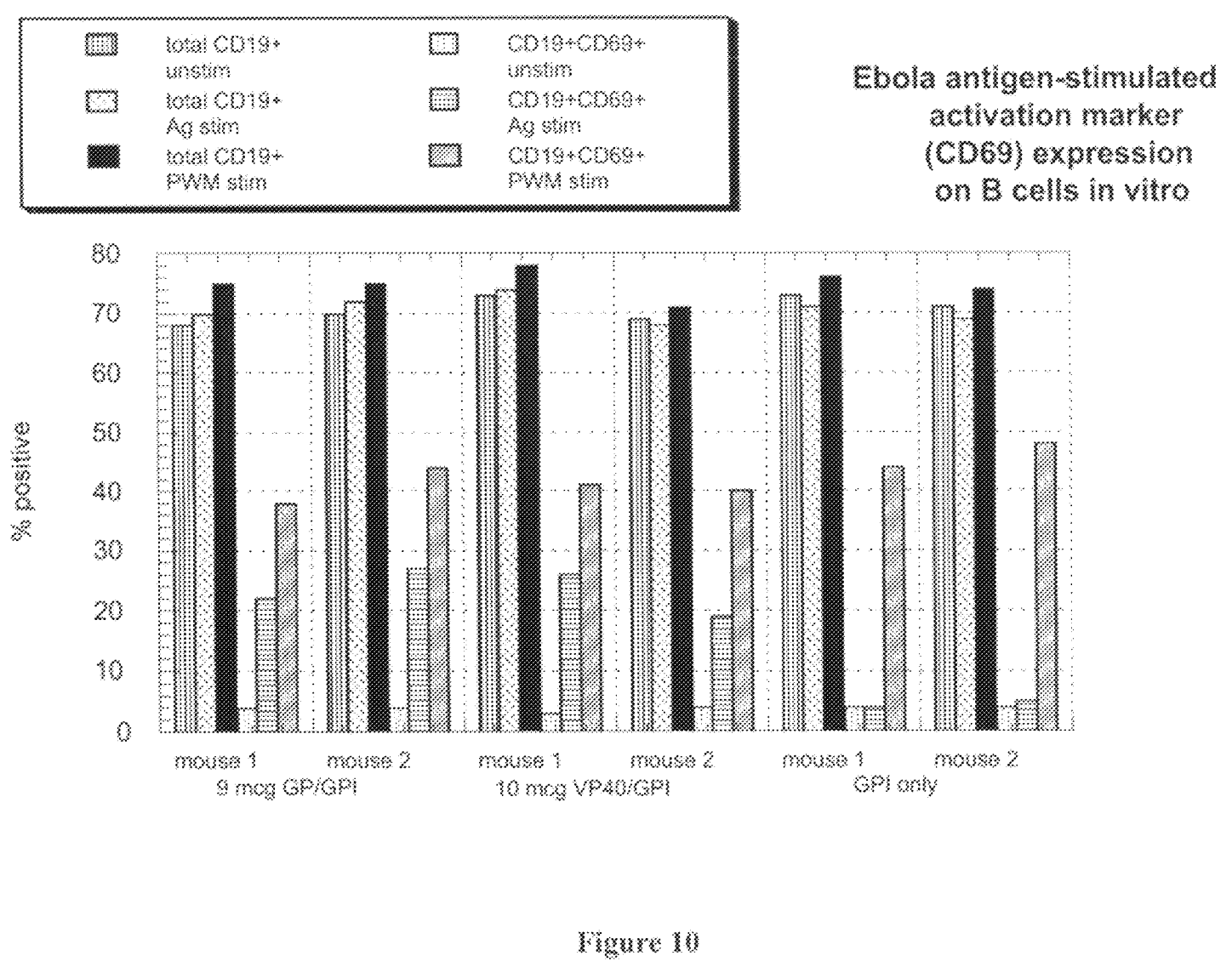

Ebola antigen-stimulated activation marker (CD69) expression on B cells in vitro total CD19+ unstim
total CD19+ Ag stim
total CD19+ PWM stim
CD19+CD69+ unstim
CD19+CD69+ Ag stim
CD19+CD69+ PWM stim % positive 0
10
20
30
40
50
60
70
80 mouse 1
mouse 2
9 mcg GP/GPI
mouse 1
mouse 2
10 mcg VP40/GPI
mouse 1
mouse 2
GPI only

Figure 10

DROSOPHILA CELL LINES PRODUCING RECOMBINANT SECRETABLE FILOVIRUS SURFACE GLYCOPROTEINS LACKING THE MEMBRANE SPANNING DOMAIN

RELATED APPLICATION

This application claims the benefit of U.S. Provisional Patent Application No. 60/724,747, filed Oct. 7, 2005, which prior application is hereby incorporated by reference in its entirety.

STATEMENT REGARDING FEDERALLY SPONSORED RESEARCH AND DEVELOPMENT

This invention was made with Government support under contract DAMD 17-00-C-0032 awarded by the United States Department of Defense (USAMRMC). The Government has certain rights in this invention.

INCORPORATION OF SEQUENCE LISTING

A sequence listing file in ST.25 format on CD-ROM is appended to this application and fully incorporated herein by reference. The sequence listing information recorded in computer readable form is identical to the written sequence listing herein (per WIPO ST.25 para. 39, the information recorded on the form is identical to the written sequence listing). With respect to the appended CD-ROM, the format is ISO 9660; the operating system compatibility is MS-Windows; the single file contained on the CD-ROM is named "EBO.ADJ.03.ST25.txt" and is a text file produced by PatentIn 3.3 software; the file size in bytes is 63 KB; and the date of file creation is 2 Oct. 2006.

BACKGROUND OF THE INVENTION

1. Technical Field

The invention relates to protection against Filovirus induced hemorrhagic fevers using recombinant proteins. The invention, more specifically, concerns several recombinant Filovirus structural proteins produced from eukaryotic cells. In the invention, proteins are post-translationally modified and are purified so that native structure is retained, thereby providing material for use as immunogens to elicit protection against virally induced disease.

"Subunit protein" is defined here as any protein derived or expressed independently from the complete organism that it is derived from. Furthermore, a subunit protein may represent a full length native protein sequence or any fraction of the full length native protein sequence. Additionally, a subunit protein may contain in addition to the full length or partial protein sequence, one or more sequences, which may contain sequences that are homologous or heterologous to the organism from which the primary sequence was derived. This definition is significantly broader than the concept of a subunit protein as a single protein molecule that co-assembles with other protein molecules to form a multimeric or oligomeric protein. The subunit proteins of the invention are produced in a cellular production system by means of recombinant DNA methods and, after purification, are formulated in a vaccine.

2. Related Art

Ebola and Marburg viruses are the only two members of the Filovirus family. They are enveloped, negative strand RNA viruses. The viral RNAs have a length of approximately 19 kb and their genome structure is 3'-NP-VP35-VP40-GP-VP30-VP24-L-5'. Upon entry into the cytoplasm of host cells, individual subgenomic, viral mRNA species are transcribed by viral RNA polymerase (RdRp). While the host cell synthesizes viral proteins in the cytoplasm, RNA dependent RNA polymerase (L) in complex with VP35 replicates the complete Filovirus RNA. Viral RNA together with nucleoprotein NP and VP30 forms the nuclear core complex. The nuclear core is inserted into Filovirus envelopes formed by the viral matrix protein VP40 in combination with VP24 and mature viral surface glycoprotein (GP) anchored into the host cell membrane. A schematic diagram of a mature Filovirus particle is shown in FIG. 1.

Marburg virus was first identified in an outbreak that occurred during 1967 in Marburg, Germany. The first human cases were animal handlers, and it was established that the source of infection were monkeys imported from Africa. For the next 9 years there were no reported outbreaks of Filovirus induced hemorrhagic fevers. In 1976, the Zaire subtype of Ebola virus first appeared in an outbreak in the Democratic Republic of Congo (known then as Zaire). A second outbreak occurred in the same year in Sudan caused by the Sudan subtype which showed lower fatality rates. Later two more subtypes were identified, Ebola Ivory-Coast and Ebola Reston. To date a total of 18 Ebola virus outbreaks have caused 1860 cases of human disease and resulted in 1296 deaths. Six Marburg virus outbreaks have to date caused 613 human infections and were fatal in 494 cases (source: WHO). Case fatality rates are dependent on the specific subtype of Filovirus causing the disease and generally vary between 50-90%, with Ebola Zaire and Marburg viruses showing the highest mortality rates. Primates are the only confirmed natural hosts for Filoviruses and human outbreaks can usually be traced back to contact with infected primates. Even though bats could serve as a potential Marburg and Ebola virus reservoir based on observations and laboratory experiments (Swanepoel et al. 1996, Leroy et al. 2005), no natural reservoir has been confirmed to date (Feldmann et al 2004).

Despite relatively few outbreaks, Ebola and Marburg viruses are well known due to their extreme virulence. Both viruses cause fulminant hemorrhagic fevers and death in up to 90% of human infections depending on the infecting strain and route of infection. Although the viruses are endemic only to certain parts of central Africa and the Philippines, the threat of a bioterrorist attack using Ebola virus has raised concern about the virus worldwide. Intentional exposure of non-human primates with aerosolized Ebola virus (Johnson et al. 1995) has demonstrated that a bioterrorist attack using Ebola or Marburg virus is feasible and could affect thousands of people. In outbreaks, it is believed that human-to-human spread only occurs upon direct contact with bodily fluids of an infected patient. However, it has been documented that an unintentional animal to animal infection was possible even without direct body contact of the individually caged rhesus monkeys (Jaax et al. 1995). In addition, recent revelations related to the efforts to produce weaponized Marburg virus in the former Soviet Union (Alibek 1999) reinforced the need to prioritize Ebola/Marburg viruses as a biodefense target. While state of the art medical treatment increases the chances of survival for patients, there are currently no antiviral therapies available to cure the disease, nor a vaccine that protects healthy individuals from infection. Supportive treatment is costly and resource demanding due to the need for strict containment. An Ebola or Marburg virus outbreak, especially in a densely populated urban area, whether caused by natural transmission or terrorist attack, could lead to many casualties and have a dramatic impact on public health systems. A safe and effective vaccine or antiviral treatment that could be used to protect healthcare workers, other at-risk persons, and travelers is therefore highly desirable.

The nucleotide sequence analysis of gene 4 of Marburg virus revealed the basic features of Filovirus surface glycoproteins (singular, "GP"; plural, "GPs") (Will et al. 1993). Filovirus GPs typically possess a hydrophobic signal peptide at the N-terminus, a hydrophilic external domain, a hydrophobic transmembrane anchor and a small hydrophilic cytoplasmic tail. The signal peptide is removed during the maturation of the glycoproteins and the external domain is heavily glycosylated, with carbohydrates accounting for approximately 50% of the molecular weight of the mature protein. Most research on the biology of Filoviruses focuses on GP, a type I transmembrane glycoprotein. GP is involved in cell entry and is therefore presumed to be a key target for virus neutralization. The Filovirus glycoproteins, on the genomic as well as on the protein level, show strain specific features; Filoviruses can therefore be differentiated and identified based on GP structure. Further analysis of the proteins expressed in Ebola and Marburg virus-infected cells revealed that in addition to the mature GP, Ebola, but not Marburg, viruses express a soluble glycoprotein (sGP). This product results from early translation termination and lacks the majority of the C-terminal region of mature GP (Volchkov et al. 1998). Since it lacks the transmembrane domain it is secreted as dimers into the extracellular space. GP and sGP are synthesized from the same gene. While sGP is synthesized from the direct mRNA transcript, it was shown that the expression of mature GP requires post-transcriptional editing of the mRNA. Expression of the edited GP gene in mammalian cells results in trimerization and the formation of characteristic spikes on the cell surface. In contrast, sGP is secreted as antiparallel-oriented homodimers stabilized by intermolecular disulfide bonds (Volchkova et al. 1998). An Ebola virus mutant was generated from cDNA that included the edited form of the GP gene (expressing mature GP only). This mutant showed a much higher cytotoxicity in comparison to wild-type Ebola virus, which is most likely linked to the much higher concentration of GP present in infected cells (Volchkov et al. 2001). The focus of the current application is on expression of the native mature GP which is expected to form trimeric structures. Immune responses targeting the native structure are more likely to protect individuals from disease than responses targeting non-native (e.g., sGP) structures.

After translation of the post-transcriptionally edited mRNA into the native (non-mutant) polypeptide, $preGP_{er}$, in the endoplasmatic reticulum, the $preGP_{er}$ polypeptide is heavily glycosylated to form preGP. Furin cleavage separates preGP into two mature subunits, GP1 and GP2, which are linked by an intermolecular disulfide bond (Volchkov et al. 1998). Mutational analysis revealed that inter- and intramolecular disulfide bonding is highly conserved and important for virus entry. Jeffers et al. (2002) suggest that disulfide bonds play a more important role in formation of functional glycoprotein than the presence of N-linked glycosylations. A similar post-translational cleavage into GP1 and GP2 is also observed on Marburg virus GP (Volchkov et al. 2000). A summary of the different pathways of Filovirus GP synthesis can be found in Feldmann et al. 2001.

The surface glycoproteins, i.e., the GPs, may contribute to the cytopathic effects observed in Filovirus infections via a variety of direct and indirect mechanisms. It has been shown that mature Ebola GP alone induces cellular detachment in cell cultures without inducing cell death (Chan et al. 2000). This is in contrast to sGP or GP1 which do not induce cellular detachment. Interestingly, Marburg virus GP does not induce similar detachment. Further characterization of the cytopathicity of GP identified that cell detachment was dependent on dynamin (Sullivan et al., 2005). It has also been shown that native mature GP can trigger activation of primary human macrophages resulting in production of proinflammatory cytokines (Wahl-Jensen et al. 2005). As Filovirus disease is often associated with overproduction of cytokines, this represents a possible mechanism for direct cytopathic effect (see further discussion of pathogenesis of Filovirus disease below). Again, this activity was associated with native, mature GP (trimeric form) and not GP1 and sGP. Furthermore, GP may contribute to the severe pathogenicity of Filovirus infection via indirect mechanisms (e.g., by inhibiting a potent protective immune response to the virus). It has been demonstrated that GP can decrease cell surface expression of MHC class I molecules (Sullivan et al., 2005). This may result in decreased immune responses upon infection. In addition, secretion of sGP as well as shedding of GP1 from virus infected cells (Dolnik et al. 2004) may diminish the activity of neutralizing antibodies.

The Filovirus surface glycoprotein is the only viral protein that is exclusively localized on the surface of the virus particles and possesses structural features to facilitate cell binding and fusion with the cell membrane. It was demonstrated that Ebola GP binds to the cell surface exposed lectins DC-SIGN and DC-SIGNR (Simmons et al. 2003). These lectins are exposed on early infection target cells such as dendritic and other antigen presenting cells and binding of these molecules may facilitate fusion efficiency by changing GP's conformation. Work by Takada et al. (2004) further confirmed the enhancement of Filovirus cell entry caused by galactose- and N-acetylgalactosamine specific C-type lectins (hMGL) present on these early target cells. The role of GP1 in cell surface receptor-binding has been suggested. Extensive mutational analysis has identified the N-terminal third of GP1 as the region most important for this first step of viral entry (Manicassamy et al. 2005). Sequence analysis of GP2 revealed the presence of a putative fusion domain (Volchkov et al. 1992). Ruiz-Arguello et al. (1998) demonstrated in vitro that the putative fusion peptide possesses liposome-binding capability. Mutational analysis using pseudotyped vesicular stomatitis viruses confirmed these findings, suggesting that the fusion process of Ebola virus might mirror that of influenza or human immunodeficiency viruses (Ito et al. 1999). A model was developed based on the hydrophobicity of the fusion peptide and tested in vitro; the testing confirmed that the fusion peptide spans residues 25 to 35 of the GP2 protein (Adam et al. 2004). Gomara et al. (2004) demonstrated further that an internal proline residue in the fusion peptide is responsible for the necessary membrane destabilization to initiate the fusion process. GP2 assembles into a rod-like trimeric structure which resembles that of other viral membrane-fusion proteins such as HIV gp41 or influenza HA2 (Weissenhorn et al. 1998). The crystal structure revealed that an internal GP2 fragment forms a trimer with a central three-stranded coiled coil structure surrounded by shorter C-terminal helices packed in an antiparallel conformation into hydrophobic grooves on the surface of the coiled coils (Malashkevich et al. 1999). Further functional analysis of the coiled-coil interactions revealed their importance in facilitating the entry of Ebola virus into host cells and demonstrated that inhibitors of this interaction could act as efficient antiviral compounds. Thus, in a mature, wild-type GP, the GP2 portion of GP is likely involved in trimerization and fusion, while the GP1 portion is likely involved in binding to the cellular receptors and facilitating entry into target cells.

To date no effective antiviral treatment against Filoviruses is available. Bray (2003) provides a comprehensive review of methods to defend against the use of Filoviruses as biological weapons. In another publication, Geisbert and Jahrling (2004) report the current status of progress towards protection against viral hemorrhagic fevers in general. In addition to immunotherapeutics and antivirals, the publication discusses several potentially supportive interventions targeting the host immune system. Potent antiviral compounds could either target virus proteins or host proteins required for appropriate virus protein processing during the viral lifecycle. The surface glycoprotein GP is a prime antiviral target because of its involvement in host cell entry. DC-SIGN binding can effectively be inhibited with hyperbranched dendritic polymers functionalized with mannose (Rojo and Delgado 2004). Another potential antiviral drug, cyanovirin-N, also exploits the DC-SIGN binding activity of GP and shows activity inhibiting GP-pseudotyped lentivirus entry into HeLa cells (Barrientos et al. 2004c). Another study demonstrated that monomeric as well as dimeric cyanovirin-N show approximately the same antiviral activity (Barrientos et al. 2004b). The importance of endosomal proteolysis by cathepsin B and L for Ebola virus entry was demonstrated by Chandran et al. (2005) and further confirmed by Schornberg et al. (2006). This suggests that cathepsin inhibitors may show activity as anti-Ebola virus drugs.

Filovirus matrix proteins (VP40) possess the general characteristic functionality of virus matrix proteins, although they show only 2-7% sequence identity to matrix proteins of other virus families (Paramyxoviridae, Rhabdoviridae, Bornaviridae). The late domain sequences important for virus budding are some of the few structurally conserved features present on the proteins of different virus families (Timmins et al. 2004). The crystal structure of a truncated Ebola virus VP40 protein (Dessen et al. 2000) revealed that it consists of two domains with unique folds connected by a flexible linker. At the beginning of the second domain is a trypsin-cleavage site after amino acid 212. The N-terminal cleavage fragment shows spontaneous hexamerization in vitro (Ruigrok et al. 2000). The N-terminal domain of VP40 is involved in the protein-protein interactions required for oligomerization while the C-terminal part is responsible for membrane-binding properties. Denaturing conditions (such as 4M urea) or membrane association induce hexamer formation of full-length VP40 (Scianimanico et al. 2000). VP40-hexamers formed from three antiparallel homodimers line the inside of Filovirus particles. On electron micrographs of Ebola virus VP40 oligomers hexameric and octameric structures were identified (Timmins et al. 2003). The disc-shaped octamers are formed in association with RNA by four antiparallel homodimers of Ebola VP40. The crystal structure revealed that the interaction with RNA induces two conformational changes of the protein (Gomis-Rüth et al. 2003). In contrast to Ebola virus VP40, the Marburg virus matrix protein forms oligomers that stack up to form complex polymeric structures. Therefore the oligomeric status could not be determined by electron microscopy.

In addition to the in vitro characterization of VP40, the cellular mechanisms involved in Filovirus budding from mammalian cells have been studied. Timmins et al. (2001) demonstrated that full-length Ebola VP40, but not the C-terminally truncated protein, is released into the culture supernatant of mammalian cells and that the matrix protein seems to be released inside vesicles. The expression of VP40 alone leads to secretion of few Filovirus-like particles, but co-expression with GP increases the formation of these structures (Noda et al. 2002, Kolesnikova et al. 2004b). Panchal et al. 2003 demonstrated in vivo that oligomers of full length Ebola VP40 are formed only in association with membranes. These oligomers seem to be transported via lipid rafts to the site of assembly. It was also shown that VP40 recruits the cellular protein Tsg101 via specific interaction with an intrinsic late budding domain (PTAP) (Licata et al. 2003). Tsg101 is involved in the vacuolar sorting pathway of mammalian cells and is important for efficient budding of numerous viruses. In addition, hexamers of VP40 can bind to the WW domain of human Nedd4, another protein involved in the late endosomal pathway necessary for efficient virus budding (Timmins et al. 2003). It was demonstrated by Yasuda et al. (2003) that Nedd4 regulates the egress of Ebola virus-like particles from mammalian cells. Despite only 29% sequence homology to the Ebola matrix protein, Marburg virus VP40 protein also associates with membranes of the late endosomal compartment both in virus-infected cells as well as in recombinant expression in mammalian cells (Kolesnikova et al. 2002, Kolesnikova et al. 2004a). While the Tsg101-binding PTAP motif is absent from Marburg virus VP40, the PPXY motif for binding of Nedd4 (Yasuda et al., 2003) is found in Marburg virus and may also to be important for efficient budding. Ebola virus VP40 shows the properties of a microtubule-associate protein (MAP) because of its binding to tubulin. It enhances tubulin polymerization in vitro (Ruthel et al. 2005). It further stabilizes microtubules against depolymerization and could therefore play a role in directed transport of virus particles to the site of budding Reviews describing the current knowledge of the impact of VP40 on molecular mechanisms involved in Filovirus cellular trafficking (Aman et al 2003) and the current understanding of the process of Filovirus budding (Jasenosky and Kawaoka 2004) have been published.

The nucleoprotein (NP) of Marburg virus self-assembles tubule-like structures when recombinantly expressed in mammalian cells. These aggregates resemble structures observed in sections of viral inclusions of Marburg virus infected cells (Kolesnikova et al. 2000). In association with cellular RNA (when expressed in Sf21 cells), Marburg virus NP forms regularly structured loose coils (Mavrakis et al. 2002). High salt treatment tightens the coiling. Ebola virus NP expressed recombinantly in mammalian cells forms intact nucleocapsids only if expressed in combination with Ebola VP35 and VP24 (Huang et al. 2002). Other virus proteins are not necessary for nucleocapsid formation, but post-translational O-glycosylation of NP is required to facilitate VP35-binding. NP increases the release of Ebola virus-like particles if co-expressed with VP40 in mammalian cells. Further addition of Ebola GP potentiates this effect (Licata et al. 2004).

The structure and function of the minor matrix protein VP24 are not fully understood. While co-expression of VP24 and VP40 in mammalian cells does not increase VLP release, co-expression of VP40, NP and VP24 in mammalian cells yields a higher amount of Ebola VLPs than co-expression of VP40 and NP alone, suggesting that VP24 may interact with NP (Licata et al. 2004). In cells infected with Ebola virus, as well as upon recombinant expression, VP24 appears to be concentrated in the perinuclear region (Han et al. 2003). VP24 from virus infected mammalian cells is not glycosylated via N-linked sugar residues and appears to tetramerize. Studies have further shown that VP24 strongly interacts with lipid bilayers and is potentially located within lipid rafts. Recent studies have shown that VP24 is essential for the formation of a functional ribonucleoprotein complex (Hoenen et al. 2006). In addition, it has been shown that VP24 seems to block proper IFN signaling giving another potential explanation of how Filoviruses evade the host immune responses (Reid et al. 2006).

The two small proteins contained in the nucleocapsid complex have different functions. VP35 is an essential part of the Filovirus nucleocapsid (Huang et al. 2002, Mühlberger et al. 1998) but the exact role in capsid assembly has not been shown yet. VP35 is a type I IFN antagonist and therefore a major contributor to Filovirus pathogenicity (Basler et al. 2003, Hartman et al. 2004). The role of the phosphoprotein VP30 is linked to transcription activation of the nucleocapsid complex. It was shown that phosphorylation on two serine residues (40 and 42) is essential for binding to NP and therefore inclusion into the nuclear core complex (Modrof et al. 2001). Phosphorylation negatively regulates transcription activation mediated by VP30 and phosphorylase inhibition can therefore inhibit Ebola virus growth (Modrof et al. 2002). It was further shown that the effect of VP30 seems to be directed at a very early step in transcription initiation (Weik et al. 2002). VP30 oligomerizes due to an internal cluster of hydrophobic residues (containing four leucine residues). Mutation of the leucine residues or application of a peptide binding to this region abolishes VP30-dependent Ebola virus transcription activation (Hartlieb et al. 2003).

The pathogenesis of Ebola virus infection is still not fully understood, even though progress towards understanding the mechanisms has been made in recent years. One finding with most hemorrhagic fever cases caused by Filoviruses is that lesions caused by the viral infection are not severe enough to account for terminal shock and death of the host. Yet this is the most common cause of death in viral hemorrhagic fevers. This suggests the involvement of inflammatory mediators as an important part in the pathogenic pathways. A simplified primate model (Sullivan et al. 2003b) suggests that initial host immune responses as well as cell damage due to infection of monocytes and macrophages causes the release of pro-inflammatory cytokines. Infection of endothelial cells causes damage to the endothelial barrier which in combination with effects of the cytokines leads to loss in vascular integrity resulting in hemorrhage and vasomotor collapse (primary cause of death in Ebola patients). Another model further elaborates on the detailed chain of events (Geisbert and Jahrling. 2004). The authors suggest that cytokines released by initially infected monocytes and macrophages recruit further macrophages to the sites of infection. This makes more target cells available for viral exploitation and further amplifies the dysregulated host response, leading to loss of lymphocytes by apoptosis. Ebola virus enhances expression of tissue factor, resulting in activation of the clotting pathway and formation of fibrin in the vasculature. These coagulation disorders are complemented by infection of hepatocytes and adrenal cortical cells resulting in impaired synthesis of important clotting factors. Studies of human Ebola Sudan patients showed leucopenia and unresponsive PBMC's, high viral loads in infected monocytes and elevated nitric oxide levels to be associated with a fatal outcome of the disease (Sanchez et al. 2004).

Primates are the only animals known to develop disease following natural infection with Filoviruses. However, in order to research virus biology, several animal models of disease have been developed, including a non-human primate model, guinea pig models, and a mouse model for Ebola virus infection using a mouse-adapted Ebola Zaire virus. Fisher-Hoch and McCormick (1999) describe several of these animal models and a publication by Ryabchikova et al. (1999) reviews animal pathology of Filoviral infections in more detail. Animal models have been used to develop the current pathogenesis model based on in vitro experiments using primate monocyte/macrophage cultures (Feldmann et al. 1996, Ströher et al. 2001) as well as in vivo experiments comparing the coagulation changes in mice, guinea pigs, and monkeys (Bray et al. 2001). While small animal models can provide insight into the virus life cycle and pathogenicity and help as an economical choice for vaccine and antiviral drug development, only non-human primates show a disease progression similar to human disease (Geisbert et al. 2002). Pathogenesis in the cynomolgus macaque model of Ebola Hemorrhagic Fever has been described in detail by Geisbert et al. (2003).

Since there is no treatment to cure Filovirus induced hemorrhagic fevers, the majority of patients succumb to the disease. However, between 10 to 50% (depending on virus strain and medical support available) of infected humans survive the disease. Following the large 1995 outbreak of Ebola Zaire in the Democratic Republic of Congo, sera of patients were analyzed. It was found that while IgM and IgG antibodies appeared at approximately the same time after onset of disease, high IgM titers persisted for a much shorter time in survivors in comparison to fatal cases (Ksiazek et al. 1999). IgG titers in survivors were detectable for at least two years following recovery. Ebola virus patients receiving convalescent sera during their illness have been reported to show a higher survival rate (Mupapa et al. 1999). Based on this observation, immune mouse sera from mice receiving sublethal doses of Ebola virus were transferred to naïve immunodeficient mice. Dose-dependent protection against virus challenge was observed in recipients of immune sera (Gupta et al 2001). Recombinant human monoclonal antibodies were constructed via phage display from bone marrow RNA of two Ebola survivors (Maruyama et al. 1999) and in vitro virus neutralization was demonstrated with one of these antibodies (Maruyama et al. 1999b). The same human monoclonal antibody was able to provide pre- and post-exposure prophylaxis in the guinea pig model of Ebola hemorrhagic fever (Parren et al. 2002). Similarly, mouse monoclonal antibodies to Ebola GP applied pre- or post-exposure were successful to protect mice against lethal Ebola virus challenge (Wilson et al. 2000). Another route to provide antibody-based protection against viral diseases is the preparation of hyperimmune serum in non-susceptible animals. Sera prepared in sheep and goats tested successfully for protection in the guinea pig model of Ebola virus (Kudoyarova-Zubavichene et al. 1999). A similarly prepared equine anti-Ebola Zaire serum was tested for protection in baboons, mice and guinea pigs. Results were inconsistent and showed low levels of protection in mice and monkeys, while all guinea pigs were protected against a lethal dose of Ebola virus. While viremia and disease onset in cynomolgus monkeys treated with the equine hyperimmune serum challenged with Ebola virus was delayed, all animals succumbed to the disease when protective antibodies had been depleted (Jahrling et al. 1996, Jahrling et al. 1999). One potential reason for the failure of passive immunizations in non-human primates could be antibody-dependent enhancement of infection (as demonstrated in vitro by Takada et al. 2003b). A further hurdle for the prophylactic or therapeutic use of neutralizing antibodies could be strain specificity. Out of five different neutralizing epitopes that have been identified on Ebola Zaire GP, none seems to have neutralizing activity against glycoproteins from the Sudan, Ivory Coast or Reston strains of Ebola virus or against the glycoprotein of Marburg virus (Takada et al. 2003).

In contrast to the mostly dramatic symptomatic cases of Filovirus infections, asymptomatic cases have been reported (Leroy et al. 2000). In only a few of these cases, specific antibody responses against Ebola virus proteins could be detected. Interestingly, the responses were directed against NP as well as VP40, and not against Filovirus glycoprotein, which is thought to be the main protective antigen and the target for virus neutralizing antibodies. The asymptomatic individuals furthermore showed early and strong inflammatory responses with high levels of circulating cytokines. These clinical parameters emphasize the importance of proper humoral and cell-mediated immunity in protection against Filovirus infection. Induction of cytotoxic T cells directed against GP was observed upon immunization of mice with liposome-encapsulated irradiated Ebola virus particles (Rao et al. 1999). Responses seem to be dependent on proper delivery of antigen to antigen presenting cells (APC). It was further demonstrated that the liposome-encapsulated virus particles can induce T cell help necessary to protect mice against lethal challenge (Rao et al. 2002). However, the same vaccine did not provide good protection in a primate model. Another study reports the generation of protective cytotoxic T lymphocytes after 2 or 3 immunizations with recombinant VEE replicons expressing Ebola NP (Wilson and Hart 2001). Even though the cellular response achieved did not yield 100% protection in the mouse model, it provides evidence that proper cellular responses will aid in protection. Identification of CTL epitopes on the nucleoprotein may lead to the discovery of potential defense mechanisms (Simmons et al. 2004). Another experiment in the mouse model demonstrated that cytotoxic memory T cells alone can protect against death, but that a persistent infection can develop if mice are deficient in helper T-cells or mount an insufficient humoral response (Gupta et al. 2004). This suggests a potential mechanism for development of a natural reservoir host animal for Filoviruses.

One of the characteristic features of Filovirus disease in infected primates is the rapid decline in the number of circulating lymphocytes. It was shown that Ebola virus induces apoptosis in natural killer cell populations by day two post-infection (Reed et al. 2004). It may therefore inhibit activation of lymphocytes by eliminating the subsets that are most likely to be capable of mounting an effective response to the virus. The viral component responsible for this has not been identified yet, although Ebola virus immune suppression seems to be linked to a domain of the surface glycoprotein and/or the VP35 protein. Studies with Ebola and Marburg virus-like particles containing GP and VP40 (Bosio et al. 2004) demonstrated activation of human myeloid dendritic cells. In contrast, administration of live or inactivated Ebola virus does not induce dendritic cell maturation. Other virus proteins not contained in the recombinant particles may be responsible for preventing this early immune response. Particles containing only the viral matrix protein VP40 were able to specifically activate natural killer cells and induce an early protective immunity against Ebola virus infection 1-3 days after immunization (Warfield et al. 2004). It was shown that the protection was mediated by perforin-mediated lysis of target cells by NK cells. This highlights another pathway that may be critical to provide successful protection against Filovirus infection.

Conventional vaccine approaches against Filovirus infection, such as attenuated or killed Filovirus particles are not generally considered feasible due to the high safety risks involved. Demonstration of proper attenuation of live viral strains in humans would be much too risky to consider and the risk of reversion would further complicate this approach. For example, a serendipitously acquired virus strain which had proven to be nonlethal to strain 13 guinea pigs proved to be lethal to Hartley guinea pigs (Hevey et al. 2002). Production of large quantities of virus to generate a killed vaccine would likewise be unacceptable from a safety point of view. Instead, several modem vaccine approaches have been the major area of research. Approaches evaluated or under evaluation include DNA vaccines, adeno-, alpha- or vesicular stomatitis virus vectored vaccines, and recombinantly produced proteins. Summarizing overviews of the advances in developing vaccines to protect against Filovirus induced hemorrhagic fevers were published in several review papers (Enserink 2003, Hart 2003, Geisbert and Jahrling 2004).

Xu et al. (1998) reported successful protection of guinea pigs against Ebola virus infection after injecting animals with 3 doses of DNA vaccines expressing either Ebola surface glycoprotein, the soluble glycoprotein sGP, or the nucleoprotein. A similar approach (Vanderzanden et al. 1998) reported successful protection of mice against Ebola virus infection after gene gun application of 4 or 5 doses of DNA vaccines encoding Ebola GP or NP. Protection of non-human primates against Ebola virus infection has been demonstrated after immunization with three doses of a combination of DNA vaccines followed by a boost utilizing a recombinant adenovirus vector expressing Ebola Zaire GP (Sullivan et al. 2000). The Vaccine Research Center at NIH is currently developing a prime-boost vaccine for human use based on this approach. It has further been shown that a single dose of the recombinant adenovirus can elicit a protective response against Ebola virus challenge four weeks after immunization (Sullivan et al. 2003). Data provided by these immunological studies strongly suggest the importance of Ebola GP in development and persistence of vaccine protection (Sullivan et al. 2003b). DNA vaccines need to be applied many times in order to raise effective immune responses. They could potentially lead to the development of autoimmune diseases and the use of strong promoters contained in the used plasmids may present a safety risk in human application. Recombinant adenoviruses may not be efficacious as vaccines on individuals with pre-existing immunity to adenoviruses and can for the same reason only be applied once. Due to safety concerns, development of adenoviral vectors for gene therapy and vaccine development has slowed in past years. In a clinical trial using adenovirus vectors for gene therapy, a patient died due to complications associated with the use of Ad5 virus (Raper et al. 2003).

Another approach for vaccine development focused on the use of alphavirus (VEE) replicons. Using vectors expressing several Marburg virus structural proteins, Hevey et al. (1998) were able to demonstrate that guinea pigs developed high specific serum antibody titers and could be protected if Marburg GP, NP or VP35 proteins were applied. Marburg virus VP40, VP30 or VP24 did not protect against viral challenge. Analogous vectors expressing Ebola virus GP, NP, VP24, VP30 or VP40 (Wilson et al 2001, Pushko et al. 2001) showed a significant level of protection against homologous challenge in vaccinated mice and guinea pigs. Passive transfer of immune sera was unsuccessful in providing protection against disease.

Recently a new vaccine approach has been tested utilizing replication-competent vesicular stomatitis virus vectors expressing surface and secreted glycoproteins of Ebola Zaire and Marburg viruses. A VSV vector expressing Ebola surface GP protected mice against lethal challenge (Garbutt et al. 2004). Further studies showed protection against homologous (but not heterologous) Filovirus challenge in guinea pigs and cynomolgus monkeys (Jones et al. 2005). Daddario-DiCaprio et al. (2006) showed that this vaccine may even provide post-exposure protection if administered at a high dose within 20-30 minutes after infection.

Virus-like particles based on recombinant proteins expressed in mammalian cell lines have been evaluated for their potential as protective vaccines against Filovirus infections. Particles containing Ebola GP and VP40 have shown to be more successful in protecting mice against lethal Ebola virus challenge than inactivated virus particles (Warfield et al. 2003). This indicates that virus inactivation may destroy necessary native structural features on the contained virus proteins. It was further demonstrated that Marburg virus-like particles constructed using Marburg virus GP and VP40 successfully induced protection against Marburg virus infection in guinea pigs, while Ebola VLPs were not protective against Marburg virus challenge (Warfield et al. 2004). Only a vaccine containing both Marburg and Ebola virus-like particles was able elicit protection against challenge with both types of Filoviruses in the guinea pig model (Swenson et al. 2005) demonstrating a lack of cross-protection between Filoviruses.

Marburg virus GP was expressed by baculovirus recombinants in Sf9 and *Trichoplusia ni* cells as full-length or truncated version without the transmembrane region. Culture supernatants formulated with Ribi adjuvant (Jennings, V. M. Review of Selected Adjuvants Used in Antibody Production. ILARJ 37:119-125. 1995) were utilized to immunize guinea pigs. Protection was achieved only against the homologous Marburg virus strain (Hevey et al. 1997). It was furthermore demonstrated that passive transfer of immune sera conferred protection to naïve guinea pigs. Baculovirus expressed full length or truncated Ebola GP was administered to guinea pigs alone (2 doses) or in a prime-boost scheme following one dose of a DNA vaccine. Prime-boost and the protein-only vaccines (applied with adjuvant) induced protective immunity in less than 50% of the animals (Mellquist-Riemenschneider et al. 2003).

An article published by Hevey et al. 2002 compared the protection in guinea pigs provided by several Marburg virus GP-based vaccine strategies. Approaches included a DNA vaccine, VEE-replicons, baculovirus expressed recombinant GP or a prime-boost approach combining DNA vaccine and recombinant protein. The study suggested that DNA vaccines and replicon-based vaccines were particularly interesting. Hart (2003) cautions that it may be dangerous to focus a vaccine approach solely on the surface glycoproteins. Certain individuals may not develop the desired T-cell responses to GP and may therefore not be protected.

Adjuvants are materials that increase the immune response to a given antigen. Since the first report of such an enhanced immunogenic effect by materials added to an antigen (Ramon, G., *Bull. Soc. Centr. Med. Vet.* (1925) 101:227-234), a large number of adjuvants have been developed, but only calcium and aluminum salts are currently licensed in the United States for use in human vaccine products. Numerous studies have demonstrated that other adjuvants are significantly more efficacious for inducing both humoral and cellular immune responses. However, most of these have significant toxicities or side-effects which make them unacceptable for human and veterinary vaccines. In fact, even aluminum hydroxide has recently been associated with the development of injection site granulomas in animals, raising safety concerns about its use. Because of these problems, significant efforts have been invested in developing highly potent, but relatively non-toxic adjuvants. A number of such adjuvant formulations have been developed and show significant promise (Cox, J. C. and Coulter, A. R., *Vaccine* (1997) 15:248-256; Gupta, R. K. and Siber, G. R., *Vaccine* (1995) 13:1263-1276), especially in combination with recombinant products. Several of these modern adjuvants are being tested in preclinical and clinical trials designed to examine both efficacy and safety.

The main modes of action of adjuvants include (i) a depot effect, (ii) direct immunomodulation through interaction with receptors, etc., on the surface of immune cells and (iii) targeting antigens for delivery into specific antigen-presenting cell populations (e.g., through the formation of liposomes or virosomes). The depot effect results from either the adsorption of protein antigens onto aluminum gels or the emulsification of aqueous antigens in emulsions. In either case this results in the subsequent slow release of these antigens into the circulation from local sites of deposition. This prevents the rapid loss of most of the antigen that would occur by passage of the circulating antigen through the liver. Immunomodulation involves stimulation of the "innate" immune system through interaction of particular adjuvants with cells such as monocytes/macrophages or natural killer (NK) cells. These cells become activated and elaborate proinflammatory cytokines such as TNF-$\alpha$ and IFN-$\gamma$, which in turn stimulate T lymphocytes and activate the "adaptive" immune system. Bacterial cell products, such as lipopolysaccharides, cell wall derived material, DNA, or oligonucleotides often function in this manner (Krieg, A. M. et al., *Nature* (1995) 374:546; Ballas, Z, J, et al., *J. of Immunology* (2001) 167:4878-4886; Chu, R. S., et al., *J. Exp. Med.* (1997) 186:1623; Hartmann, G. and Krieg, A., *J. Immunol.* (2000) 164:944-952; Hartmann, G., et al., *J. of Immunol.* (2000) 164:1617-1624; Weeratna, R. D. et al., *Vaccine* (2000) 18:1755-1762; U.S. Pat. Nos. 5,663,153; 5,723,335; 6,194,388; 6,207,646; 6,214,806; 6,218,371; 6,239,116; 6,339,068; 6,406,705; 6,429,199). Targeting of antigens to (and within) antigen presenting cells is accomplished through the delivery and fusion of antigen bearing vehicles (e.g., liposomes or virosomes) with antigen presenting cells, thereby delivering the antigen into the intracellular pathways necessary for presentation of antigen in the context of MHC Class I and/or II molecules (Leserman, L., *J. Liposome Res.* (2004) 14:175-89; Bungener et al., *Vaccine* (2005) 23:1232-41).

In addition to these more traditional adjuvants, various new technologies are under development. One of them includes the use of dipeptidyl peptidases, which have shown promising results in human cancer therapy. The biological activity of dipeptidyl peptidases may reflect adjuvant-like properties (e.g. generating cytokine and chemokine production), as shown in preclinical animal models in response to their administration. These responses are believed to enhance both antigen-presentation to naive T-cells and the co-stimulation of antigen-specific T-cells. The use of adjuvants in combination with recombinant antigens is widely known in the art and can result in vaccines with better efficacy.

Thus, there is an unmet need for vaccines against Filoviruses. A key technical problem to be solved is the efficient production of conformationally relevant Filovirus surface glycoproteins, as well as additional structural proteins, that serve as potent immunogens in vaccinated subjects. Related technical problems are the production and formulation of effective vaccines that have improved costs of production and distribution.

SUMMARY OF THE INVENTION

The inventors have identified unique combinations of antigens and adjuvants that induce relevant protective immune responses and have shown an acceptable safety profile in vaccinated individuals. These unique formulations depend upon several novel, properly folded recombinant subunit proteins (Filovirus GP, VP40, VP24 or NP) combined with one or more adjuvants, such as saponins, emulsions, and alum-based formulations. These antigen/adjuvant combinations (1) induce or enhance relevant, protective immune responses, such as protein specific antibody and cell mediated responses, and (2) maintain an acceptable safety profile. The disclosed invention provides immunogenic compositions containing as active ingredients recombinantly-produced Filovirus glycoprotein(s), and optionally, additional structural virus proteins. A preferred embodiment of the disclosed invention comprises the recombinant truncated surface glycoprotein of one or more Ebola or Marburg viruses as active ingredients. A preferred embodiment of the disclosed invention alternatively includes a full-length Filovirus surface glycoprotein and/or several other structural Filovirus proteins. A preferred embodiment of the disclosed invention also includes an adjuvant, such as a saponin or a saponin-like material (e.g., GPI-0100, ISCOMATRIX®), alum-based formulations (e.g., Alhydrogel®), or emulsion-based formulations (e.g., ISA-51, Co-Vaccine HT, Ribi R-700), either alone or in combination with other immunostimulants and adjuvants, as a component of the immunogenic formulations described herein. Typically, the disclosed immunogenic formulations are capable of eliciting the production of antibodies against Filoviruses, for example Ebola Zaire, and stimulating cell-mediated immune responses.

Other aspects of this invention include use of a therapeutically effective amount of the immunogenic composition in an acceptable carrier for use as an immunoprophylactic against Filovirus infection and a therapeutically effective amount of the immunogenic composition in an acceptable carrier as a pharmaceutical composition.

BRIEF DESCRIPTION OF THE DRAWINGS

Figure 1:
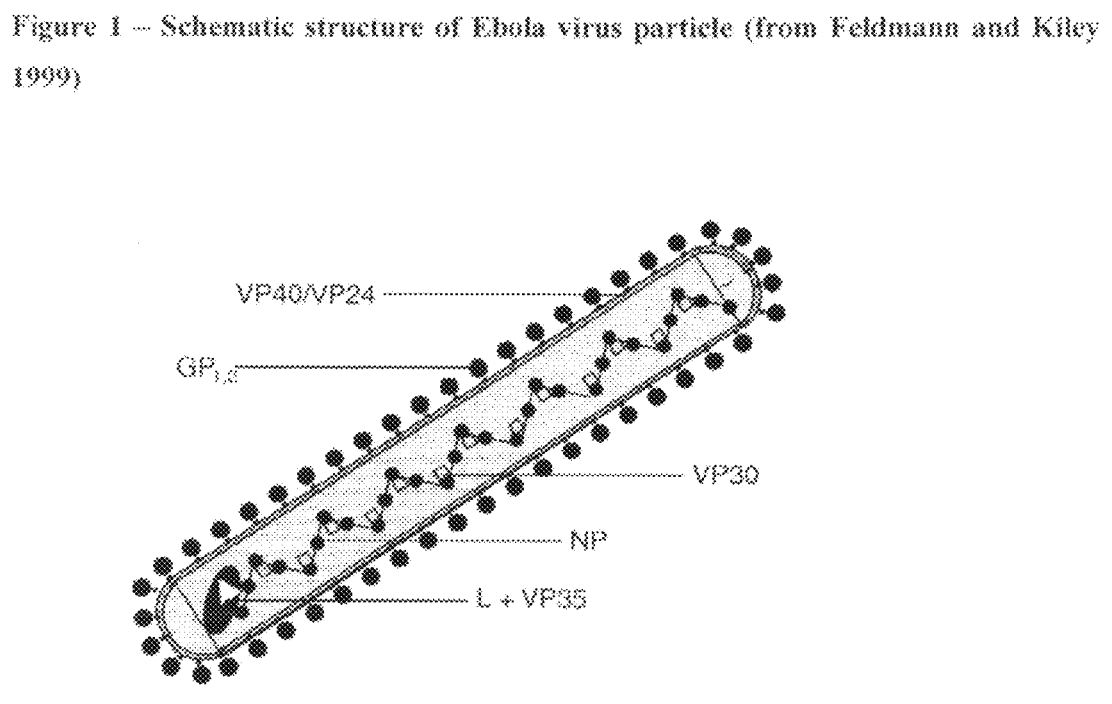

FIG. 1 shows a schematic structure of Ebola virus particle.

FIG. 2 shows a Sodium Dodecyl Sulfate Polyacrylamide Gel electrophoresis (SDS-PAGE) panel demonstrating expression and secretion of Ebola Zaire GP95, VP40 and VP24 proteins. Loading of gel: Lanes 1, 6 and 11—prestained broad range protein marker showing molecular weights in kDa (NEB); Lanes 2-4—each loaded with 10 μl of 3 different culture supernatants from a VP40 expression line (reducing sample buffer); Lanes 7-9—each loaded with 10 μl of 3 different culture supernatants from a VP24 expression line (non reducing); lanes 13-15—each loaded with 10 μl of 3 different culture supernatants from GP95 expression line (non reducing conditions).

FIG. 3 shows an SDS-PAGE panel demonstrating Immunoaffinity Chromatography (IAC) purified Ebola Zaire GP95 under reducing and non-reducing conditions. Sample loading on 10% Coomassie stained SDS-PAGE gel: (1) prestained broad range molecular weight marker with molecular weights in kDa (NEB; www.neb.com); (2) 1 μg GP95, reducing conditions; (3+9) 1 μg GP95, PNGase treated to remove N-linked glycosylations, reducing conditions; (4+10) 1 μg GP95, fully deglycosylated, reducing conditions; (5 and 6) fetuin as control to verify proper enzymatic deglycosylation; (8) 1 μg GP95, non-reducing conditions. A: identifies band of GP95, B: shows GP1 region, C: identifies location of deglycosylated GP1, D: GP2 (2 or more bands), E: deglycosylated GP2.

FIG. 4 shows an SDS-PAGE panel demonstrating IAC purified Ebola Zaire VP40 under reducing and non-reducing Conditions. Sample loading on silver-stained 12% SDS-PAGE gel (1 μg VP40 loaded per lane): (1) Mark12 (Invitrogen Corp.)—molecular weights in kDa, (2) VP40 (lot #588-161) reduced, (3) VP40 (lot #609-73) reduced, (4) VP40 (lot #619-23) reduced, (5) VP40 (lot #588-161) not reduced, (6) VP40 (lot #609-73) not reduced, (7) VP40 (lot #169-23) not reduced.

FIG. 5 shows an SDS-PAGE panel demonstrating IAC purified Ebola Zaire VP24 under reducing and non-reducing conditions. VP24 is expressed by S2 cells in three glycoforms (mono-, di- and tri-glycosylated) which co-purify on the IAC column. The lanes have been loaded with Mark12 (protein marker from Invitrogen Corp.)—molecular weights in kDa, (1)=1.0 μg final purified VP24 and (2)=0.1 μg final purified VP24.

FIG. 6 shows an SDS-PAGE panel demonstrating reactivity of individual recombinant Ebola Zaire virus proteins with Ebola specific hyperimmune mouse ascites fluid (HMAF). FIG. 6 is a Western blot of 12% SDS-PAGE gel with following loading pattern: Lane 1—prestained broad range protein marker (NEB)—molecular weights in kDa; Lanes 2, 4, 5—each loaded with 10 μl of 3 different culture supernatants from VP40 expression line (reducing conditions), lane 3: PNGase treated supernatant from VP40 expression line (reducing conditions); Lane 6: loaded with 10 μl of culture supernatant from GP95 expression line (non reducing conditions); Lane 7: loaded with 10 μl of PNGase treated supernatant from GP95 expression line (reducing conditions); Lanes 8, 9, 10: each loaded with 10 μl of 3 different culture supernatants from GP95 expression line (non reducing), lanes 11, 13 and 14—each loaded with 10 μl of 3 different culture supernatants from VP24 expression line, lane 12: PNGase treated supernatant from VP24 expression line (non reducing conditions). Western blot was probed with anti-Ebola HMAF (reactive against ZEBOV, SEBOV, REBOV).

FIG. 7 shows an SDS-PAGE panel demonstrating the reactivity of individual recombinant proteins with a VP40-specific monoclonal antibody. FIG. 7 is a Western blot of 12% SDS-PAGE gel with identical loading to FIG. 6, but probed with A10A (binds to ZEBOV VP40)—which antibody binds to glycosylated and non-glycosylated proteins, and also reacts with VP40 dimers.

FIG. 8 shows an SDS-PAGE panel demonstrating the reactivity of individual recombinant proteins with a GP-specific monoclonal antibody. FIG. 8 is a Western blot of 12% SDS-PAGE gel with identical loading to FIG. 6, but probed with the conformationally sensitive antibody 13C6 (reactive against ZEBOV GP). The antibody does not bind to the deglycosylated GP95 protein (see lane 7).

FIG. 9 shows an SDS-PAGE panel demonstrating the reactivity of individual recombinant proteins with a VP24-specific monoclonal antibody. FIG. 9 is a Western blot of 12% SDS-PAGE gel with identical loading to FIG. 6, but probed with BG11 (reactive against ZEBOV VP24)—which antibody binds to the three glycoforms as well as deglycosylated forms.

FIG. 10 is a histograph showing induction of B Cell Memory in Balb/c Mice with recombinant Ebola Zaire GP95 and VP40.

DESCRIPTION OF THE PREFERRED EMBODIMENTS

The invention described herein provides subunit Filovirus immunogenic formulations that are produced using a recombinant expression system; the formulations typically include one or more adjuvants. The disclosed immunogenic formulations are effective in inducing strong antibody responses directed against individual Filovirus proteins and intact Filovirus particles as well as stimulating cell-mediated immune responses to the viruses (see Examples 3 and 4).

The inventors and their colleagues have successfully developed a method of expression in insect cell culture systems that produce recombinant structural proteins from Filoviruses such as Ebola Zaire, Ebola Sudan or Marburg virus. The surface glycoprotein is either expressed full length or in a truncated form, removing about 5% of the mature protein. The scope of the truncated proteins used in the invention includes any surface glycoprotein subunit secretable by the expression system. The preferred truncation deletes the membrane spanning portion (situated within the GP2 region, entailing approximately the carboxy-terminal 30 amino acids, thus allowing it to efficiently be secreted into the extracellular medium, facilitating recovery). "Expression" and "to express" are synonymous with "secretion" and "to secrete" as used herein. Cloning and expressing full length Filovirus GP is possible, but secretion is less efficient due to the membrane anchor. However, the membrane spanning domain does not contain any known antigenic epitopes and inclusion of the membrane spanning domain reduces yields; therefore the membrane spanning domain and the cytosolic tail portions of GP are not included in the preferred antigen, a subunit, surface glycoprotein of Filoviruses described below and called "GP95". "Secretable" means able to be secreted, and typically secreted, from the transformed cells in the expression system. Furthermore, the expressed proteins have been shown to be properly glycosylated and achieve native conformation as determined by reactivity with the conformationally sensitive monoclonal antibody, 13C6-1-1 ("13C6"; Wilson et al., 2000) (Example 2). The proteins are potent immunogens when administered in combination with modern adjuvants (Examples 3 and 4) and have been shown to induce protective efficacy in a small animal model for Ebola Hemorrhagic Fever (see Example 5 below). Thus the inventors have found a novel solution to a key technical problem: the efficient production of conformationally relevant Filovirus surface glycoproteins that serve as potent immunogens in vaccinated subjects.

The invention also provides for the use of adjuvants as components in an immunogenic composition compatible with the purified proteins to boost the immune response resulting from vaccination. One or more preferred adjuvants are selected from the group comprising saponins (e.g., GPI-0100 (Hawaii Biotech, Inc., Aiea, Hawaii), ISCOMATRIX® (CSL Limited, Parkville, Victoria, Australia)) (saponin, saponin-derivative, and saponin-like substances are collectively referred to herein as "saponin-based"), alum-based adjuvants (e.g., Alhydrogel (Superfos Export Co., 15 Amaliegade, Copenhagen, Denmark), or emulsion-based adjuvants (e.g., Co-Vaccine HT (Co-Vaccine BV, Lelystad, Flevoland, Netherlands), Ribi R-700 (GlaxoSmithKline, Philadelphia, Pa.), Montanide ISA-51 (Seppic, Paris, France). Aluminum-based adjuvants (collectively, "alum" or "alum-based adjuvants") are aluminum hydroxide, aluminum phosphate, or a mixture thereof. Aluminum hydroxide (commercially available as "Alhydrogel®") was used as alum in the Examples.

The antigens used in the disclosed immunogenic compositions typically comprise one or more truncated Filovirus surface glycoprotein subunits and may further contain additional structural virus protein subunits. For example, a preferred immunogenic composition comprises one or more surface glycoprotein subunits (preferably GP95) expressed and secreted from insect cells, preferably *Drosophila* S2 cells. The surface glycoprotein subunit (i.e., truncated, secretable GP95 protein) from the Ebola Zaire virus ("ZEBOV") is used in the prototype vaccine composition. Surface glycoproteins subunits from other Filoviruses, such as Marburg virus ("MARV"), e.g. of the Musoke, Angola or Popp strains, Ebola Sudan Virus ("SEBOV"), Ebola Ivory-Coast Virus ("ICEBOV") or Ebola Reston Virus ("REBOV") can be used as replacement or additional antigens in the disclosed invention.

One or more optional recombinant Filovirus structural protein subunits can be included in the disclosed immunogenic composition. For example, one or more insect cell, preferably *Drosophila* Schneider 2 cell-expressed, structural protein subunits (preferably VP40, VP24, or NP), preferably from the homologous Filovirus, are included in some embodiments of the disclosed immunogenic compositions. Inclusion of such structural protein subunits typically results in exceptionally potent vaccine formulations.

The combination of one or more viral subunit GP95, with or without other structural protein subunits, and optionally with one or more adjuvants, induces very high titer antibodies in mice. For example, certain combinations of a saponin-based adjuvant, preferably GPI-0100, with a given recombinant antigen, yield a high titer of antibodies and cell-mediated immune responses. Examples illustrating the immunogenicity and protective efficacy of such novel combinations are disclosed below (Examples 3, 4 and 5).

For C-terminally truncated protein subunits of the invention, the C-terminal truncation point can be varied up to plus or minus 2% of the length of the specified sequence length of a given protein so long as such variation does not affect secretion of the protein and conformation of the epitopes of the secreted subunit protein. For instance, the specified length of the ZEBOV GP95 protein subunit is 617 residues, but the actual truncation point may range from approximately 605 residues to 629 residues so long as such variation does not affect secretion of ZEBOV GP95 and conformation of the epitopes of the secreted ZEBOV GP95.

Surface Glycoprotein Subunits (GP95)

In a preferred embodiment of the invention, the recombinant protein subunits of the Filovirus vaccine formulations described herein are produced by a eukaryotic expression system, *Drosophila melanogaster* Schneider 2 ("*Drosophila* S2" or simply "S2") cells (Johansen, H. et al., *Genes Dev.* (1989) 3:882-889; Ivey-Hoyle, M., *Curr. Opin. Biotechnol.* (1991) 2:704-707; Culp, J. S., et al., *Biotechnology* (NY) (1991) 9:173-177). This method of expression successfully produces recombinant surface glycoproteins from Filoviruses, such as Ebola Zaire (ZEBOV). These proteins are truncated at the C-terminus, leaving approximately 95% of the mature surface glycoprotein (GP95) sequence. The truncation deletes the membrane spanning region of the protein, thus allowing it to be efficiently secreted into the extracellular medium using a homologous or heterologous secretion signal, facilitating recovery. Alternatively, full-length GP (GP-FL) may be expressed using a homologous or heterologous secretion signal. The expressed proteins (GP95 and GP-FL) have been shown to be properly glycosylated and to maintain native conformation as determined by reactivity with a conformationally sensitive monoclonal antibody (13C6, see Example 2). The amino acid sequence listing of ZEBOV GP95 is SEQ ID: 1. The nucleotide sequence listing, including leading and trailing nucleotides (collectively, "bookends") used in cloning, that encodes ZEBOV GP95 is SEQ ID: 2. The nucleotide sequence listing, without "bookends" used in cloning, that encodes ZEBOV GP95 is SEQ ID: 3. The amino acid sequence listing of SEBOV GP95 is SEQ ID: 4. The nucleotide sequence listing, including leading and trailing nucleotides (collectively, "bookends") used in cloning, that encodes SEBOV GP95 is SEQ ID: 5. The nucleotide sequence listing, without "bookends" used in cloning, that encodes SEBOV GP95 is SEQ ID: 6. The amino acid sequence listing of MARV GP95 is SEQ ID: 7. The nucleotide sequence listing, including leading and trailing nucleotides (collectively, "bookends") used in cloning, that encodes MARV GP95 is SEQ ID: 8. The nucleotide sequence listing, without "bookends" used in cloning, that encodes MARV GP95 is SEQ ID: 9. The amino acid sequence listing of ZEBOV GP-FL is SEQ ID: 10. The nucleotide sequence listing, including leading and trailing nucleotides (collectively, "bookends") used in cloning, that encodes ZEBOV GP-FL is SEQ ID: 11. The nucleotide sequence listing, without "bookends" used in cloning, that encodes ZEBOV GP-FL is SEQ ID: 12.

In another embodiment of the invention, GP95 is defined more broadly as a truncated surface glycoprotein that comprises two subunits (GP1 and GP2-95) that are linked via a disulfide bridge, wherein the polypeptide has been secreted as a recombinant protein from *Drosophila* cells, and wherein the polypeptide generates antibody responses to a homologous strain of a species of Filovirus.

In another preferred embodiment, the surface glycoprotein subunit further comprises a hydrophilicity profile characteristic of at least a homologous 95% portion of a surface glycoprotein (GP) starting from the first amino acid at the N-terminus of the mature surface glycoprotein of a strain of a species of Filovirus. In other words, amino acids can be substituted in the sequence comprising GP-FL or GP95 so long as the hydrophilicity profile and immunogenicity are unchanged.

The immunogenicity and protective efficacy of such GP proteins have also been demonstrated in an animal model (see Examples 3-5).

"GP95" in one instance refers to a polypeptide that spans a Filovirus surface glycoprotein, preferably one starting from the N-terminal amino acid of the mature surface glycoprotein and ending at an amino acid in the range of the $647^{th}$ to $648^{th}$ amino acid, for example, such GP95 can be the polypeptide comprising amino acids 33 to 647 of ZEBOV or SEBOV or amino acids 19 to 648 of MARV.

"GP-FL" in one instance refers to a polypeptide that spans a Filovirus surface glycoprotein, preferably one starting from the N-terminal amino acid of the mature surface glycoprotein and ending at an amino acid in the range of the $676^{th}$ to $681^{st}$ amino acid, for example, such GP-FL can be the polypeptide comprising amino acids 33 to 676 of ZEBOV or SEBOV or amino acids 19 to 681 of MARV.

Preferably, the ZEBOV surface glycoprotein subunit is a portion of the ZEBOV surface glycoprotein that comprises approximately 95% of its length starting from amino acid residue 1 at its N-terminus and which portion has been recombinantly produced and secreted from *Drosophila* cells. In another embodiment, GP95 is at least 80%, or 85%, or 90%, or 95% homologous over the entire sequence relative to native Filovirus GP, or alternatively relative to the sequence listings disclosed in SEQ ID NOS: 1, 4, and 7, as the case may be, so long as such variation from native Filovirus GP, or SEQ ID NOS:1, 4, and 7, respectively, does not affect secretion of the GP95 subunit and conformation of the epitopes of the secreted GP95 subunit.

In another embodiment, GP-FL is at least 80%, or 85%, or 90%, or 95% homologous over the entire sequence relative to native Filovirus GP, or alternatively relative to the sequence listing disclosed in SEQ ID NO:10, so long as such variation from native Filovirus GP, or SEQ ID NO:10, respectively, does not affect secretion of the GP-FL subunit and conformation of the epitopes of the secreted GP-FL subunit.

More preferably, GP is derived from homologs or variants as described above, e.g., all Ebola Zaire strains as well as any serotypes of: Ebola Sudan virus (SEBOV), Ebola Ivory-Coast and Marburg virus (MARV). The GP95 and GP-FL proteins preferably are produced from vectors containing the DNA encoding the Filovirus GP fused to a heterologous secretion signal (e.g. BiP (Kirkpatrick et al., 1995) or TPA (Culp et al., 1991)). The proteins are processed by cellular signalases to release the mature GP95 or GP-FL proteins.

In one embodiment, the immunogenic composition comprises the surface glycoprotein subunit derived from Ebola Zaire virus. Preferably, the GP95 subunit from Ebola Zaire virus is purified by immunoaffinity chromatography (IAC) using a monoclonal antibody (e.g. 13C6; Wilson et al., 2000) as described in Example 2. Alternatively, the GP95 subunit from Ebola Zaire virus is purified by conventional chromatography methods or alternative affinity purification methods (e.g., wheat germ lectin chromatography (Dolnik et al. 2004)), which are known to one skilled in the art.

In one embodiment, the immunogenic composition comprises the surface glycoprotein subunit derived from Ebola Sudan virus. Preferably, the GP95 subunit from Ebola Sudan virus is purified by immunoaffinity chromatography (IAC) using a monoclonal antibody (e.g., 13C6) as described in Example 2. Alternatively, the GP95 subunit from Ebola Sudan virus is purified by conventional chromatography methods or alternative affinity purification methods (e.g., wheat germ lectin chromatography (Dolnik et al. 2004)) which are known to one skilled in the art.

In one embodiment, the immunogenic composition comprises the surface glycoprotein subunit derived from Marburg virus. Preferably, the GP95 subunit from Marburg virus is purified by immunoaffinity chromatography (IAC) using a monoclonal antibody as described for Ebola Zaire GP95 in Example 2. Alternatively, the GP95 subunit from Marburg virus is purified by conventional chromatography methods or alternative affinity purification methods (e.g., wheat germ lectin chromatography (Dolnik et al. 2004)), which are known to one skilled in the art.

Trimeric GP95

Numerous studies have demonstrated that immunogenicity is directly related both to the size of the immunogen and to the antigenic complexity of the immunogen. Thus, in general, larger antigens make better immunogens. The native form of GP found on the surface of the Filovirus virion is a homotrimer (Volchkov et al. 1998b). The majority of the recombinant GP95 protein prepared using the method of production disclosed herein is present in solution as trimers and dimers in addition to a smaller portion of monomer. Trimers of GP may be stabilized by protein cross-linking agents (e.g., formaldehyde, EGS) after purification. In a preferred embodiment, the surface glycoproteins from ZEBOV, SEBOV or MARV are prepared as trimeric antigens.

Matrix Protein (VP40)

In addition to the Filovirus surface glycoproteins discussed above, the immunogenic formulations of the described invention optionally include the Filovirus matrix protein VP40. The recombinant protein components of the Filovirus vaccine formulations described herein are produced by a eukaryotic expression system, *Drosophila melanogaster* Schneider 2 (S2) cells (see references above). This method of expression successfully produces recombinant matrix proteins from Filoviruses, such as Ebola Zaire (ZEBOV). These proteins are expressed full length and may be expressed as a fusion with a eukaryotic secretion signal (e.g., from BiP or TPA) thus allowing it to be efficiently secreted into the extracellular medium, facilitating recovery. Furthermore, the secreted protein has been shown to be glycosylated, while the non-secreted protein is not. The secreted V40 was shown to maintain native conformation as determined by reactivity with a VP40-specific monoclonal antibody M-HD06-A10A ("A10A") produced by United States Army Medical Research Institute for Infectious Diseases ("USAMRIID"), as shown in Example 2. The amino acid sequence listing of ZEBOV VP40 is SEQ ID: 13. The nucleotide sequence listing, including leading and trailing nucleotides (collectively, "bookends") used in cloning, that encodes ZEBOV VP40 is SEQ ID: 14. The nucleotide sequence listing, without "bookends" used in cloning, that encodes ZEBOV VP40 is SEQ ID: 15.

In another embodiment of the invention, VP40 is defined more broadly as a full length matrix protein that comprises one or more N-linked glycosylations, wherein the polypeptide has been secreted with or without the use of an eukaryotic secretion signal as a recombinant protein from *Drosophila* cells, and wherein the polypeptide generates antibody responses to a homologous or heterologous strain of a species of Filovirus.

In another preferred embodiment, the matrix protein further comprises a hydrophilicity profile characteristic of a homologous matrix protein (VP40) starting from the first amino acid at the N-terminus of the matrix protein of a strain of a species of Filovirus. In other words, amino acids can be substituted in the sequence comprising VP40 so long as the hydrophilicity profile and immunogenicity are unchanged.

The immunogenicity of such VP40 proteins have also been demonstrated in an animal model (see Examples 3-5).

"VP40" in one instance refers to a polypeptide that spans the entire Filovirus matrix protein, preferably one starting from the N-terminal amino acid of the mature matrix protein and ending at an amino acid in the range of the $303^{rd}$ to $326^{th}$ amino acid, for example, such VP40 can be the polypeptide comprising amino acids 1 to 326 of the ZEBOV protein.

Preferably, the ZEBOV matrix protein is a portion of the ZEBOV matrix protein that comprises up to 100% of its length starting from amino acid residue 1 at its N-terminus and which portion has been recombinantly produced and secreted with or without a heterologous secretion signal from *Drosophila* cells. In another embodiment, VP40 is at least 80%, or 85%, or 90% or 95% homologous over the entire sequence relative to native Filovirus VP40, or alternatively relative to the sequence listing disclosed in SEQ ID NO:13, so long as such variation from native Filovirus, or SEQ ID NO:13, respectively, VP40 does not affect secretion of the VP40 subunit and conformation of the epitopes of the secreted VP40 subunit. More preferably, VP40 is derived from homologs or variants as described above, e.g., all Ebola virus variants as well as any serotypes of Marburg virus (MARV). The VP40 proteins preferably are produced from vectors containing the DNA encoding the VP40 proteins fused at the N-terminus to a heterologous secretion signal (e.g., BiP or TPA). The proteins are processed by cellular signalases to release the mature and glycosylated VP40 proteins. The VP40 proteins alternatively are produced without secretion signal from vectors containing the DNA encoding the VP40 proteins. The proteins are released at similar expression levels via alternative pathways into the culture supernatant mimicking the protein shedding observed from Filovirus infected cells.

In one embodiment, the immunogenic composition comprises the VP40 matrix protein derived from Ebola Zaire virus. Preferably, recombinant VP40 from Ebola Zaire virus is purified by immunoaffinity chromatography (IAC) using a monoclonal antibody (e.g., A10A) as described in Example 2. Alternatively, the recombinant VP40 from Ebola Zaire virus is purified by conventional chromatography methods which are known to one skilled in the art.

Minor Matrix Protein (VP24)

In addition to the Filovirus surface glycoproteins discussed above, the immunogenic formulations of the described invention optionally include the Filovirus minor matrix protein VP24. The Filovirus vaccine formulations described herein are produced by a eukaryotic expression system, *Drosophila melanogaster* Schneider 2 (S2) cells (see references above). This method of expression successfully produces recombinant minor matrix proteins from Filoviruses, such as Ebola Zaire (ZEBOV). The proteins are expressed full length and are expressed as a fusion with a eukaryotic secretion signal (e.g., BiP or TPA) thus allowing it to be efficiently secreted into the extracellular medium, facilitating recovery. Furthermore, the secreted protein has been shown to be glycosylated (Example 2). It was shown to maintain native conformation as determined by reactivity with a VP24-specific monoclonal antibody (BG11, see Example 2). The amino acid sequence listing of ZEBOV VP24 is SEQ ID: 16. The nucleotide sequence listing, including leading and trailing nucleotides (collectively, "bookends") used in cloning, that encodes ZEBOV VP24 is SEQ ID: 17. The nucleotide sequence listing, without "bookends" used in cloning, that encodes ZEBOV VP24 is SEQ ID: 18.

In another embodiment of the invention, VP24 is defined more broadly as a full-length, minor matrix protein, wherein the polypeptide has been secreted as a recombinant protein from *Drosophila* cells which may or may not be glycosylated, and wherein the polypeptide generates antibody responses to a homologous or heterologous strain of a species of Filovirus.

In another preferred embodiment, the minor matrix protein further comprises a hydrophilicity profile characteristic of a homologous portion of a minor matrix protein (VP24) starting from the first amino acid at the N-terminus of the minor matrix protein of a strain of a species of Filovirus. In other words, amino acids can be substituted in the sequence comprising VP24 so long as the hydrophilicity profile and immunogenicity are unchanged.

The immunogenicity and protective efficacy of such glycosylated VP24 proteins have also been demonstrated in an animal model (see Examples 3-5).

"VP24" in one instance refers to a polypeptide that spans a Filovirus minor matrix protein, preferably one starting from the N-terminal amino acid of the mature minor matrix protein and ending at an amino acid in the range of the $251^{st}$ to $253^{rd}$ amino acid, for example, such VP24 can be the polypeptide comprising amino acids 1 to 251 of ZEBOV virus.

Preferably, the ZEBOV minor matrix protein VP24 is a portion of the ZEBOV minor matrix protein that comprises up to 100% of its length starting from amino acid residue 1 at its N-terminus and which protein has been recombinantly produced and secreted with a heterologous secretion signal from *Drosophila* cells. In another embodiment, VP24 is at least 80%, or 85%, or 90% or 95% homologous over the entire sequence relative to native Filovirus VP24, or alternatively relative to the sequence listing disclosed in SEQ ID NO:16, so long as such variation from native Filovirus VP24 does not affect secretion of the VP24 subunit and conformation of the epitopes of the secreted VP24 subunit. More preferably, VP24 is derived from homologs or variants as described above, e.g., all Ebola virus variants as well as any serotypes of Marburg virus (MARV). The VP24 proteins preferably are produced from vectors containing the DNA encoding the VP24 proteins fused at the N-terminus to a heterologous secretion signal (e.g., BiP or TPA). The proteins are processed by cellular signalases to release the mature and glycosylated VP24 proteins.

In one embodiment, the immunogenic composition comprises the minor matrix protein derived from Ebola Zaire virus. Preferably, recombinant VP24 from Ebola Zaire virus is purified by immunoaffinity chromatography (IAC) using a monoclonal antibody, for example Z-AC01-BG11-01

("BG11"; Wilson et al., 2001), as described in Example 2. Alternatively, the recombinant VP24 from Ebola Zaire virus is purified by conventional chromatography methods, which are known to one skilled in the art.

Nucleoprotein Subunits (NP)

In addition to the Filovirus glycoproteins discussed above, the immunogenic formulations of the described invention optionally include the Filovirus nucleoprotein NP. The Filovirus vaccine formulations described herein are produced by a eukaryotic expression system, *Drosophila melanogaster* Schneider 2 (S2) cells (see references above). This method of expression successfully produces recombinant nucleoproteins from Filoviruses, such as Ebola Zaire (ZEBOV). These proteins are expressed full length or as truncated subunits and may be expressed as a fusion with a eukaryotic secretion signal (e.g., from BiP or TPA) thus allowing it to be secreted into the extracellular medium, facilitating recovery. Furthermore, the expressed protein has been shown to be glycosylated. It was shown to maintain native conformation as determined by reactivity with two monoclonal antibodies (D04-AE8 and FB03-BE08, see Example 2). The amino acid sequence listing of ZEBOV NP is SEQ ID: 19. The nucleotide sequence listing, including leading and trailing nucleotides (collectively, "bookends") used in cloning, that encodes ZEBOV NP is SEQ ID: 20. The nucleotide sequence listing, without "bookends" used in cloning, that encodes ZEBOV NP is SEQ ID: 21.

In another embodiment of the invention, NP is defined more broadly as a full length nucleoprotein that may comprise one or more N-linked glycosylations, wherein the polypeptide may have been secreted with the use of an eukaryotic secretion signal as a recombinant protein from *Drosophila* cells, and wherein the polypeptide generates antibody responses to a homologous or heterologous strain of a species of Filovirus.

In another preferred embodiment, the nucleoprotein further comprises a hydrophilicity profile characteristic of a homologous nucleoprotein (NP) starting from the first amino acid at the N-terminus of the nucleoprotein of a strain of a species of Filovirus. In other words, amino acids can be substituted in the sequence comprising NP so long as the hydrophilicity profile and immunogenicity are unchanged.

"NP" in one instance refers to a polypeptide that spans the nucleoprotein, preferably one starting from the N-terminal amino acid of the mature nucleoprotein and ending at an amino acid in the range of the $692^{nd}$ to $739^{th}$ amino acid, for example, such NP can be the polypeptide comprising amino acids 1 to 739 of ZEBOV virus.

Preferably, the ZEBOV nucleoprotein NP is a portion of the ZEBOV nucleoprotein that comprises up to 100% of its length starting from amino acid residue 1 at its N-terminus and which portion has been recombinantly produced with or without a heterologous secretion signal from *Drosophila* cells. In another embodiment, NP is at least 80%, or 85%, or 90% or 95% homologous over the entire sequence relative to native Filovirus NP, or alternatively relative to the sequence listing disclosed in SEQ ID NO:19, so long as such variation from native Filovirus NP or SEQ ID NO:19, respectively, does not affect secretion of the NP subunit and conformation of the epitopes of the secreted NP subunit. More preferably, NP is derived from homologs or variants as described above, e.g., all Ebola virus variants as well as any serotypes of Marburg virus (MARV). The NP proteins preferably are produced from vectors containing the DNA encoding the NP proteins. The NP proteins alternatively are produced from vectors containing the DNA encoding the NP proteins fused at the N-terminus to a heterologous secretion signal (e.g., BiP or TPA). The proteins are then processed by cellular signalases to release the mature and glycosylated NP proteins.

In one embodiment, the immunogenic composition comprises the nucleoprotein derived from Ebola Zaire virus. Preferably, recombinant NP from Ebola Zaire virus is purified by immunoaffinity chromatography (IAC) using a monoclonal antibody (e.g., Z-D04-AE8 produced by the United States Army Medical Research Institute for Infectious Diseases) as described in Example 2. Alternatively, the recombinant NP from Ebola Zaire virus is purified by conventional chromatography methods, which are known to one skilled in the art.

Adjuvants

In addition to the antigenic components described above, the invention optionally contains an adjuvant which aids in inducing a potent, protective immune response to the conformationally relevant antigen, Saponin or Saponin-Based Adjuvants In an especially preferred embodiment of the invention, a saponin or saponin-based adjuvant such as ISCOMATRIX® or GPI-0100 are added to the recombinant subunit surface glycoprotein, with or without additional structural proteins in the composition. Targeting specific antigen-presenting cell (APC) populations may involve a particular receptor on the surface of the APC, which could bind the adjuvant/antigen complex and thereby result in more efficient uptake and antigen processing as discussed above. For example, a carbohydrate-specific receptor on an APC may bind the sugar moieties of a saponin such as ISCOMATRIX® or GPI-0100 (Kensil, C. R. et al., *J. Immunol.* (1991) 146:431-437; Newman M. J. et al., *J. Immunol.* (1992) 148:2357-2362; U.S. Pat. Nos. 5,057,540; 5,583,112; 6,231,859). Although the validity of the invention is not bound by this theory, a possible mechanism of action may be that if the saponin is also bound to an antigen, this antigen would thus be brought into close proximity of the APC and more readily taken up and processed. Similarly, if the adjuvant forms micellar or liposomal complexes with antigen and the adjuvant can interact or fuse with the APC membrane, this may allow the antigen access to the cytosolic or endogenous pathway of antigen processing. As a result, peptide epitopes of the antigen may be presented in the context of MHC class I molecules on the APC, thereby inducing the generation of CD8+ cytotoxic T lymphocytes ("CTL"; Newman et al., supra; Oxenius, A., et al., *J. Virol.* (1999) 73: 4120).

A saponin is any plant glycoside with soapy action that can be digested to yield a sugar and a sapogenin aglycone. Sapogenin is the nonsugar portion of a saponin. It is usually obtained by hydrolysis, and it has either a complex terpenoid or a steroid structure that forms a practicable starting point in the synthesis of steroid hormones. The saponins of the invention can be any saponin as described above or saponin-like derivative with hydrophobic regions, especially the strongly polar saponins, primarily the polar triterpensaponins such as the polar acidic bisdesmosides, e.g. saponin extract from Quillajabark Araloside A, Chikosetsusaponin IV, Calendula-Glycoside C, chikosetsusaponin V, Achyranthes-Saponin B. Calendula-Glycoside A, Araloside B, Araloside C, Putranjia-Saponin III, Bersamasaponiside, Putrajia-Saponin IV, Trichoside A, Trichoside B, Saponaside A, Trichoside C, Gypsoside. Nutanoside, Dianthoside C, Saponaside D, aescine from *Aesculus hippocastanum* or sapoalbin from *Gyposophilla struthium*, preferably, saponin extract *Quillaja saponaria* Molina and Quil A. In addition, saponin may include glycosylated triterpenoid saponins derived from *Quillaja Saponaria* Molina of Beta Amytin type with 8-11 carbohydrate moieties as described in U.S. Pat. No. 5,679,354. Saponins as defined herein include saponins that may be combined with other materials, such as in an immune stimulating complex ("ISCOM")-like structure as described in U.S. Pat. No. 5,679,354. Saponins also include saponin-like molecules derived from any of the above structures, such as GPI-0100, such as described in U.S. Pat. No. 6,262,029.

Preferably, the saponins of the invention are amphiphilic natural products derived from the bark of the tree, *Quillaia saponaria*. Preferably, they consist of mixtures of triterpene glycosides with an average molecular weight ($M_W$) of 2000. A particularly preferred embodiment of the invention is a purified fraction of this mixture.

The most preferred embodiment of the invention is one or more GP95 proteins combined with ISCOMATRIX® or GPI-0100 to produce a vaccine formulation able to induce potent, safe, protective immune responses in vaccinated subjects, including members of the immunodeficient population.

Emulsion and Emulsion-Based Adjuvants

In another preferred embodiment, an emulsion or emulsion-based adjuvant, such as Montanide ISA-51, Co-Vaccine HT, or Ribi R-700, is added to the recombinant subunit GP protein, with or without additional structural proteins in the composition. Emulsions and emulsion-based vaccines such as those formulated with Montanide ISA-51 (see Example 3) are known in the art (Podda A. and G. DelGiudice, Expert Rev. Vaccines (2003) 2:197-203; Banzhoff A. et al., Gerontology (2003) 49:177-84) and are believed to function primarily through a depot effect. CoVaccine HT does not function in this manner. Rather it most likely functions as an immune modulator, since it contains carbohydrate moieties bound to micro-droplets of vegetable oil, which is thought to mimic the bacterial cell surface. Thus, while this adjuvant is physically an emulsion, its mode of action as an adjuvant is that of an immunomodulator. Ribi R-700 (or other adjuvants of the Ribi Adjuvant System, (GlaxoSmithKline, Philadelphia, Pa.) contains highly purified microbial cell wall constituents such as monophosphoryl lipid A (MPL) and Synthetic Trehalose Dicorynomycolate (TDM) in an emulsion of metabolizable oil. Like CoVaccine HT, Ribi R-700 also demonstrates a immunomodulatory effect in addition to the depot and antigen presentation advantages of an emulsion.

While reports in the literature (Podda and DelGiudice; Banzhoff et al.) have suggested that addition of emulsions such as MF59 to subunit vaccines may overcome some of the immune difficulties in the elderly, side by side evaluation with another unadjuvanted, subunit-like (split influenza) vaccine formulation failed to show an added benefit (Ruf et al.), resulting in a lack of medical endorsement for the use of the MF59 adjuvanted vaccine (Prescrire Int.). Addition of carbohydrates or immunostimulatory molecules to an emulsion (e.g., Co-Vaccine HT) is believed to further enhance the adjuvant effect through more effective stimulation of antigen presenting cells as described above. Thus, the combination of an emulsion-based adjuvant containing additional immunostimulatory molecules with a conformationally relevant recombinant Filovirus surface glycoprotein produces a particularly potent vaccine composition. In a highly preferred embodiment, ZEBOV GP95 is combined with Co-Vaccine HT to produce a vaccine formulation able to induce potent, protective immune responses in vaccinated subjects.

In a preferred embodiment, the recombinant Filovirus surface glycoprotein, with or without additional structural proteins in the composition, is formulated with aluminum-based adjuvants (collectively, "alum" or "alum-based adjuvants") such as aluminum hydroxide, aluminum phosphate, or a mixture thereof. Aluminum-based adjuvants remain the only adjuvants currently registered for human use in the United States and their effectiveness is widely recognized. Aluminum-based adjuvants are believed to function via a depot mechanism and the combination of the conformationally relevant Filovirus surface glycoprotein antigen with the depot effect is sufficient to induce a potent immune response in vaccinated individuals.

Dipeptidyl Peptidase Inhibitors

Dipeptidyl Peptidase Inhibitors are synthetic molecules that inhibit the dipeptidyl peptidase (DPP) family of serine proteases. These enzymes digest proteins found naturally in the body and regulate tumor growth and immune responses. Inhibition of certain DPPs appears to stimulate the immune system to mount an attack against infectious agents or tumors. Inhibition of DPP 8/9 in monocytes has been shown to induce the release of IL-1β, a key molecule stimulating immune responses, which then stimulates cytokine and chemokine production (www.pther.com).

The cytokines and chemokines involved in the response to orally administered DPP inhibitors are known to promote the body's own anti-tumor defenses, including the activity of T-cells, neutrophils, monocytes/macrophages and natural killer cells. Based on the same mechanism, the responses to externally administered antigens can be enhanced.

Administration and Use

The described invention thus concerns and provides a means for preventing or attenuating infection by Filovirus. As used herein, a vaccine is said to prevent or attenuate a disease if administration of the vaccine to an individual results either in the total or partial immunity of the individual to the disease, or in the total or partial attenuation (i.e., suppression) of a symptom or condition of the disease.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The active vaccines of the invention can be used alone or in combination with other active vaccines such as those containing other active subunits or formulations containing or expressing homologous or heterologous immunogens. Corresponding or different subunits from one or several serotypes may be included in a particular formulation.

The therapeutic compositions of the described invention can be administered parenterally by subcutaneous, intramuscular, intradermal, or transdermal (e.g., topical) application.

Many different techniques exist for the timing of the immunizations when a multiple administration regimen is utilized. It is preferable to use the compositions of the invention more than once to increase the levels and diversities of expression of the immunoglobulin repertoire as well as the population size of mature T-cells in the immunized subject. Typically, if multiple immunizations are given, they will be given one to two months apart.

To immunize subjects against Filovirus-induced disease for example, the vaccines containing the subunit(s) are administered to the subject in conventional immunization protocols involving, usually, multiple administrations of the vaccine. Administration is typically by injection, typically intramuscular or subcutaneous injection; however, other modes of administration may also be employed.

According to the described invention, an "effective amount" of a therapeutic composition is one which is sufficient to achieve a desired biological effect. Generally, the dosage needed to provide an effective amount of the composition will vary depending upon such factors as the subject's age, condition, sex, and extent of disease, if any, and other variables which can be adjusted by one of ordinary skill in the art. The antigenic preparations of the invention can be administered by either single or multiple dosages of an effective amount. Effective amounts of the compositions of the invention can vary from 0.01-500 μg per dose, more preferably from 0.1-20 μg per dose, and most preferably 1-5 μg per dose.

EXAMPLES

Example 1

Cloning of Filovirus Structural Genes and Expression in Insect Cells

Cloning of Required Genes into Vectors for Expression in Insect Cells

Sequences for expression of four selected Ebola Zaire virus proteins nucleoprotein NP, glycoprotein GP and the small viral proteins VP24 and VP40 were accessed from Genbank (www.ncbi.nlm.nih.gov/Genbank/index.html) Ebola Zaire, Mayinga strain; accession number NC_002549. PCR amplification used specially designed DNA primers and cDNA plasmids to prepare the properly positioned inserts containing required restriction sites and stop codons. This allowed directional cloning into the selected expression vectors (pMT/BiP/V5-His A (with BiP secretion signal) and pMT/V5-His A (no secretion signal), Invitrogen Corp., www.invitrogen.com). All plasmids contained the *Drosophila* metallothionein promoter to allow inducible protein expression in insect cells.

The endogenous secretion signal (first 32 amino acids) of the surface glycoprotein GP gene was removed to allow for standardized expression conditions in all constructs using the well characterized BiP secretion signal. Native full-length GP contains a membrane anchor at the C-terminal end. In one construct the full-length GP was cloned. In another construct, the membrane anchor was removed in order to achieve maximum secretion of the expressed protein (last 29 amino acids deleted) with the resulting product comprising 95% of the full-length GP protein and being referred to as GP95. As NP and VP40 are not normally secreted proteins, expression was evaluated from both a secreted and non-secreted construct. Table 1 summarizes the cloned coding sequences.

For details about the preparation of the expression plasmids and use in the *Drosophila* expression system, see commonly assigned U.S. Pat. Nos. 6,165,477; 6,416,763; 6,432,411; and 6,749,857, the contents of which are fully incorporated herein by reference. Unless otherwise defined herein, the definitions of terms used in such commonly assigned patents and related to the *Drosophila* expression system shall apply herein. The DNA sequences cloned into the plasmids in such commonly assigned patents are, of course, different from, and superseded by, the cloned Filovirus sequences disclosed herein.

TABLE 1

Summary of cloned genomic sequences for expression of Ebola subunit proteins

| Ebola subunit protein | Plasmid | Cloned genomic information (position in bp)* | Expressed subunit protein (based on wildtype protein) |
|---|---|---|---|
| Glycoprotein (GP95) (secreted) | pMT/BiP-EboZ-GP95 | 6135-7979 (edited) | amino acids 33-647 |
| Nucleoprotein (NP) (secreted) | pMT/BiP-EboZ-NP | 470-2689 | Full length |
| VP24 (secreted) | pMT/BiP-EboZ-VP24 | 10346-11101 | Full length |
| VP40 (secreted) | pMT/BiP-EboZ-VP40 | 4479-5459 | Full length |
| Glycoprotein Full-length (GP-FL) (secreted) | pMT/BiP-EboZ-GP-FL | 6135-8069 (edited) | amino acids 33-676 |
| Nucleoprotein (NP NS) (not secreted) | pMT-EboZ-NP-NS | 470-2689 | Full length |
| VP40 NS (not secreted) | pMT-EboZ-VP40-NS | 4479-5459 | Full length |

*Basepair numbers listed are based on Genbank accession number NC_002549)

Stable Transformation of *Drosophila* S2 Cells and Analysis of Protein Expression

*Drosophila* S2 cells adapted to ExCell 420 (SAFC; www.sigmaaldrich.com) were co-transformed with one of the expression plasmids for Ebola Zaire VP40 (secreted or non-secreted), VP24, NP (secreted or non-secreted) or GP (95% or full-length) and one of the selectable marker plasmids pCoHygro or pCoBlast (Invitrogen Corp.; www.invitrogen.com) using the calcium phosphate coprecipitation method. Stable expression of each individual subunit was verified in at least 1-2 duplicate cell lines. Samples of culture medium following induction with 200 μM $CuSO_4$ were evaluated by polyacrylamide gel electrophoresis followed by Coomassie staining and Western Blot. Blots were probed with anti-Ebola HMAF (polyvalent hyperimmune mouse ascitic fluid) or individual monoclonal antibodies reactive against Ebola Zaire virus proteins. HMAF (raised in ICR mice immunized with irradiated SEBOV, ZEBOV and REBOV) reacted with all expressed Ebola subunit proteins. Some background reactions were observed when HMAF was used, whereas monoclonal antibodies detected only the appropriate subunits.

A summary of expression yields and product properties can be found in Table 2.

TABLE 2

Summary of Expression for Recombinant Ebola Virus Proteins

| Ebola Subunit Protein | Aminoacid sequence contained* | Predicted molecular weight | Estimated expression level | Comments on expressed protein |
|---|---|---|---|---|
| VP40 (secreted) | 1-326 (full length) | 35.4 kDa | 10-20 mg/L | Uniform expression pattern of major (>90%) and minor (<10%) band of singly glycosylated product. Potentially differentially folded products. |

TABLE 2-continued

Summary of Expression for Recombinant Ebola Virus Proteins

| Ebola Subunit Protein | Aminoacid sequence contained* | Predicted molecular weight | Estimated expression level | Comments on expressed protein |
|---|---|---|---|---|
| VP24 (secreted) | 1-251 (full length) | 28.5 kDa | 10-20 mg/L | Product secreted as three glycoforms. |
| NP (secreted) | 1-739 (full length) | 83.6 kDa | 1-2 mg/L | Majority of the expression product is secreted, various product sizes in supernatant, single band product in cell fraction. |
| GP95 (secreted) | 33-647 | 67.6 kDa | 10 mg/L | Single band suggests uniform glycosylation status of the product. |
| VP40 NS (Non-secreted) | 1-326 (full length) | 35.2 kDa | 1-5 mg/L | Approximately half of the protein is retained within cells, the rest can be found in culture supernatant. No glycosylation and much lower expression level compared to secreted VP40. |
| NP NS (Non-Secreted) | 1-739 (full length) | 83.3 kDa | 1-5 mg/L | >90% retained inside the cells, one uniform size of product of around 100 kDa. Higher yield than when expressed in secreted form. |
| GP-FL | 33-676 | 70.9 kDa | 1-5 mg/L | Majority of protein is secreted as a single size product. Expression level is lower than for truncated GP. |

*Position based on native Ebola virus proteins as contained in Genbank NC_002549

Production of Soluble Secreted Ebola VP40, VP24, GP95 and NP Proteins

Figures 2, 3:
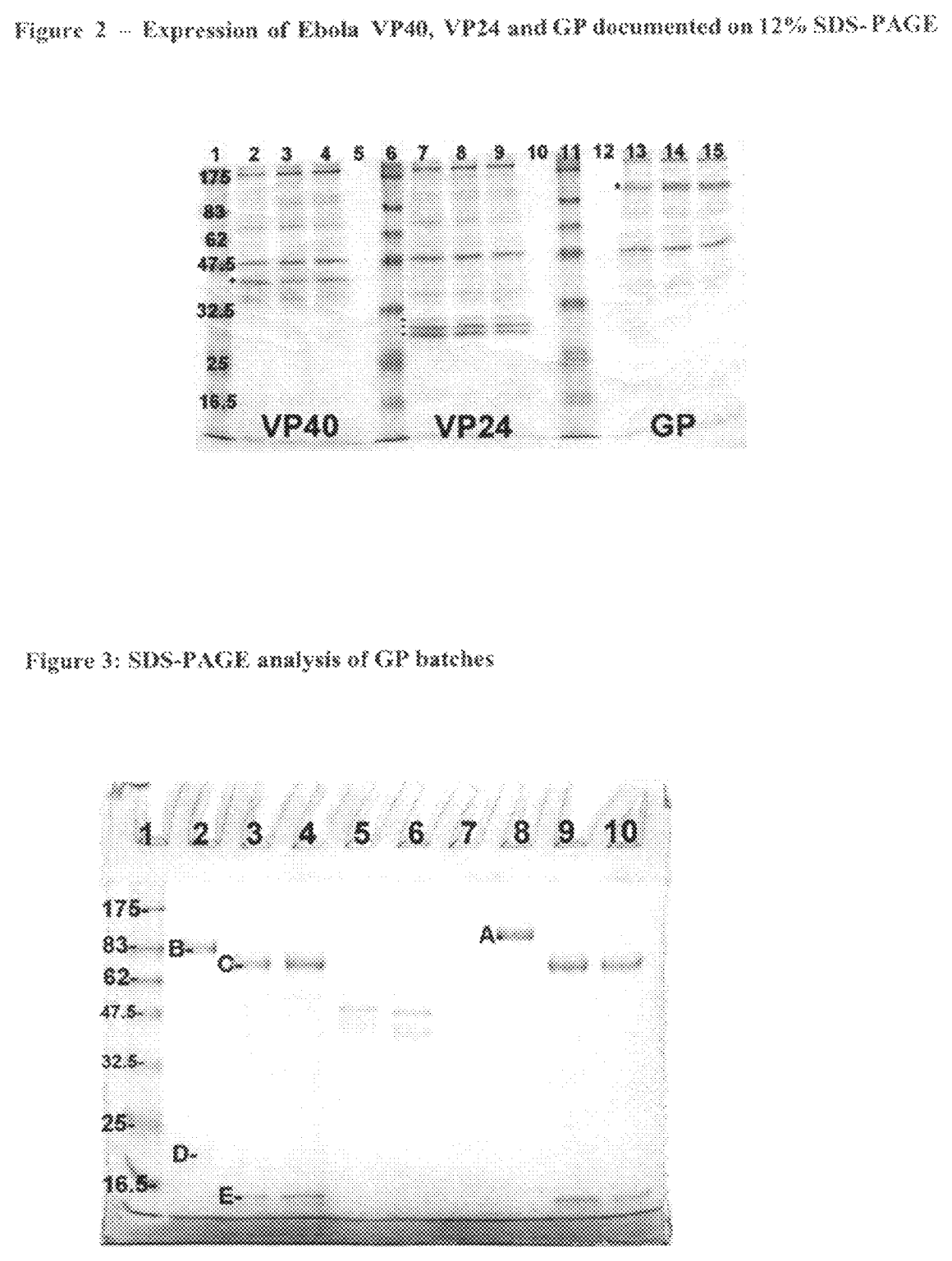

The cell lines expressing secreted forms of VP40, VP24, GP95 or NP were scaled up and several 400 ml spinner flask cultures or a stirred-tank Bioreactor were inoculated at 1-2× $10^6$ cells/ml. Expression in each culture flask was induced after 48 hours by adding $CuSO_4$ to the media. Culture supernatants were harvested on day 7. Expression was verified by polyacrylamide gel electrophoresis and Western Blot. FIG. 2 shows a Coomassie stained PAGE gel containing expression products from selected spinner flask culture supernatants.

Example 2

Purification of Recombinant Filovirus Proteins

Monoclonal antibodies specific to individual Ebola virus proteins obtained from United States Army Medical Research Institute for Infectious Diseases ("USAMRIID") (Table 3) were coupled to NHS-sepharose (Amersham; www.amershambiosciences.com) at ratios of 10 mg to 1 ml of matrix. Culture medium was loaded directly onto the immunoaffinity chromatography (IAC) columns and bound protein was eluted with 20 mM glycine buffer at pH 2.5 after a PBS wash. Eluates were neutralized and buffer exchanged into PBS using ultrafiltration devices (Centriplus, Millipore; www.millipore.com). Final products were filtered using 0.2 μm syringe filters and protein content determined by UV absorption and gel-electrophoresis. Silver staining of final gels was used to determine the approximate purity of proteins (FIGS. 3, 4 and 5). Yields and purity of each protein are summarized in Table 4.

TABLE 3

Monoclonal antibodies used for Ebola subunit purification

| Antibody specificity | Antibody name |
|---|---|
| VP24 | Z-AC01-BG11-01 |
| VP40 | M-HD06-A10A |
| GP | 13C6-1-1 |
| NP | ZD04-AE8 |
| NP | FB03-BE-08 |

TABLE 4

Summary of purified soluble Ebola proteins

| Soluble Ebola protein | Estimated Purity | Amount purified |
|---|---|---|
| VP24 | >95% | 13.9 mg |
| GP95 (batch 1) | >90% | 10.5 mg |
| GP95 (batch 2) | >90% | 12.1 mg |
| GP95 (batch sw) | >90% | 37.9 mg |
| VP40 (batch 1) | 85-90% | 3.55 mg |
| VP40 (batch 2) | 90% | 2.8 mg |
| VP40 (batch 3) | 85-90% | 3.8 mg |

The glycosylation status of purified soluble VP40, VP24, NP and GP95 proteins was determined using PNGase (New England Biolabs, www.neb.com) or an enzymatic deglycosylation kit (E-DEGLY, Sigma, www.sigma-aldrich.com) to remove N- or O-linked sugars from the tested proteins. Molecular weight analysis of glycosylated versus non-glycosylated proteins was conducted on SDS-PAGE gels using Coomassie staining. This was correlated with results from gels probed with a glycoprotein in-gel stain kit (Invitrogen; www.probes.invitrogen.com) and Western blots probed with antibodies reactive to individual proteins (see FIGS. 6-9).

GP

For recombinant GP95 protein, a 10 ml immunoaffinity column (prepared with 107 mg of EGP13C6 MAb) was used to purify three batches from 800 ml (batch 1), 1200 ml (batch 2) or 4000 ml (batch sw) culture supernatant as described above. Coomassie stained SDS-PAGE gels were used to analyze the product (FIG. 3). One major product can consistently be observed (>90% purity) in purified material of all batches.

The size of the secreted product is estimated to be approximately 110 kDa (full length—see lane 8). In a reduced sample (lane 2), GP1 can be observed around 90 kDa and GP2 at approximately 20 kDa, indicating efficient post-translational processing by furin. Native protein gels as well as FPLC data (size exclusion chromatography) suggest that the majority of GP95 in solution is present as dimers and trimers. A Western blot probed with the conformationally sensitive antibody 13C6 is shown in FIG. 8.

Purified GP95 was also analyzed by MALDI-ToF. The molecular weight of the GP95 aglycon (monomer) is 89 kDa and the N-linked glycosylation adds an additional 21.4 kDa per monomer.

GP contains 7 potential N-linked glycosylation sites, 5 in the GP 1 region and two in the GP2 region. N-linked glycosylations were confirmed in both regions by PNGase treatment. Analysis showed no evidence for O-linked glycosylation of the up to 21 potential O-glycosylation sites.

VP40

For the purification of 3 batches (lots #588-161, #609-73 and #619-23VP40 protein a 2 ml immunoaffinity column (prepared with 19 mg of M-HD06-A10 A MAb) was used. 800 to 1600 ml of culture supernatant were loaded directly onto the IAC column and VP40 eluted after a PBS wash. Silver stained gels were used to analyze the products of all three lots (FIG. 4). VP40 is secreted by S2 cells as two products that co-purify on the IAC column. The apparent sizes of the two VP40 bands on protein gels are 44 and 40 kDa. A Western blot probed with the Ebola Zaire VP40-specific monoclonal antibody A10A is shown in FIG. 7.

Both forms of secreted VP40 show a single N-linked sugar moiety as determined by PNGase digestion and consistently appear as a major and a minor band product on SDS-PAGE gels. Dimers and higher oligomers are observed as a “smear” above the major protein band under non-reducing conditions but disappear under reducing conditions (FIG. 4). Based on enzymatic deglycosylation, there is no indication of O-linked glycosylation in VP40 expressed and secreted from insect cells.

N-terminal sequencing of both of the VP40 bands showed efficient processing of the BiP secretion signal and the amino acid sequence of the first 10 amino acids was identical. This rules out that the alternate translation initiation site at $M_{14}$ is being used by our insect cell line. This alternate expression product was confirmed when VP40 was expressed in mammalian cells (Jasenosky et al. 2001).

Purified VP40 (lot #588-161) was also analyzed by MALDI-ToF (Autoflex, Bruker Daltonics, www.bdal.com). It showed a molecular weight of 36.8 kDa for the secreted VP40 with one confirmed N-linked glycosylation. The theoretical weight of the aglyco-form is 35.4 kDa. Peptide mass fingerprint data suggests that the glycosylation site at Asn25 is processed. The second site at Asn222 is apparently not glycosylated.

VP24

For recombinant VP24 protein, a 10 ml immunoaffinity column (prepared with 93 mg of Z-AC1-BG11 MAb) was used to purify VP24 from 800 ml of culture supernatant. The purification scheme was as described above. Silver stained gels were used to analyze the product (FIG. 5). The apparent molecular weights for the three bands on this silver stained PAGE gel are 32, 29 and 26 kDa which can be attributed to the presence of single, double and triple glycosylated products. PNGase treatment results in reduction to one band of lower molecular weight (~25 kDa) on SDS-PAGE. Purity of the product is estimated at >95%. A Western blot of purified VP24 probed with ZEBOV specific monoclonal antibody reactive against VP24 is shown in FIG. 9.

Purified VP24 (predicted molecular weight of polypeptide: 28.4 kDa) shows the following molecular weights by MALDI-ToF: 28.9, 29.9 and 30.9 kDa. The peptide mass fingerprint suggests that the protein is partially glycosylated at the predicted sites Asn86, Asn187 and Asn248.

NP

Both available NP reactive monoclonal antibodies were coupled to NHS-sepharose (approx. 100 mg of monoclonal antibody bound to 10 ml sepharose). Both columns were tested for their ability to purify NP recombinant protein. The binding efficiency of both NP columns was low compared to GP or VP24 columns. The Z-D04-AE8 column in comparison to the FB03-BE-08 column showed higher yields. The purification of recombinant NP proteins from S2 culture medium by this method resulted in product that was estimated to be below 50% in purity.

Example 3

Immunogenicity of Recombinant Ebola Virus Proteins in Balb/c Mice

The immunogenicity of the purified recombinant VP24, VP40, and GP95 proteins was tested in Balb/c mice. The candidate vaccines were formulated using two adjuvants with different modes of action. The saponin-based GPI-0100 (Hawaii Biotech, Inc.) provides a direct immuno-stimulatory and -modulatory effect, while Montanide ISA-51 (Seppic, www.seppic.com) is an oil-in-water emulsion that provides a depot effect. Mice were immunized by subcutaneous injection three times at 4-week intervals with the test vaccine formulations. Details of the experimental groups are summarized in Table 5 below. One week after the third dose, 5 mice from each group were splenectomized. The rest were terminally bled two weeks after the third dose. All mice were also tail-bled at weeks 2 and 6. Splenocytes were stimulated in vitro with antigen and analyzed for proliferative capacity and secretion of cytokines post-stimulation (by ELISA). Antigen specific antibody titers in the tail- and terminal bleeds were determined by ELISA using immunizing antigent irradiated Ebola virus as coating antigen.

TABLE 5

Mouse immunogenicity study using soluble recombinant Ebola virus proteins

| Group no. | Adjuvant | Immunogen | No. of mice | Formulation | Route |
|---|---|---|---|---|---|
| 1 | GPI-0100 | 10 μg GP95 | 15 | 100 μg of GPI-0100 is mixed with 10 μg antigen and PBS | s.c. |
| 2 | ISA-51 | 10 μg GP95 | 15 | 50% ISA-51 is mixed into adequate volume of immunogen in PBS | s.c. |
| 3 | GPI-0100 | 10 μg VP-40 | 10 | 100 μg of GPI-0100 is mixed with 10 μg antigen and PBS | s.c. |
| 4 | ISA-51 | 10 μg VP-40 | 10 | 50% ISA-51 is mixed into adequate volume of immunogen in PBS | s.c. |
| 5 | GPI-0100 | 10 μg VP-24 | 10 | 100 μg of GPI-0100 is mixed with 10 μg antigen and PBS | s.c. |
| 6 | ISA-51 | 10 μg VP-24 | 10 | 50% ISA-51 is mixed into adequate volume of immunogen in PBS | s.c. |

TABLE 5-continued

| Mouse immunogenicity study using soluble recombinant Ebola virus proteins | | | | | |
|---|---|---|---|---|---|
| Group no. | Adjuvant | Immuno-gen | No. of mice | Formulation | Route |
| 7 | GPI-0100 | NONE | 10 | 100 μg of GPI-0100 is mixed with PBS | s.c. |
| 8 | ISA-51 | NONE | 10 | 50% ISA-51 is mixed into adequate volume of PBS | s.c. |

The results of the immunogenicity study are summarized in Table 6. The Stimulation Indices present the fold-increase of tritiated thymidine uptake in antigen-stimulated cells divided by unstimulated control cells of the same animal. To allow comparison, data from adjuvant-only control groups stimulated with respective antigens has also been included. The ELISA titers are expressed as the GMT of individual EC50 titers based on sigmoid curve fitting on a logarithmic scale (using Origin 7.5 software, www.originlab.com).

The lymphoproliferation data reveals strong immune responses to all three recombinant Ebola proteins. The specific stimulation indices (SI) ranged from 2.2 up to 15.1 where an SI≧3 is generally considered significant. Relatively high levels of cytokines (IL-4, IL-5, IL-10) were secreted by stimulated splenocytes, particularly in the groups receiving the GPI-0100 adjuvant.

Interferon gamma (IFN-γ) levels rose to levels clearly above control values and suggest that Th1 type responses have been induced with all three immunogens. Formulations with both adjuvants seem to induce approximately equal IFN-γ responses with all three antigens.

ELISA titers obtained with all three immunogens show that relatively high serum titers against the antigens were induced following 2 vaccine doses with further increase following administration of a 3$^{rd}$ dose.

TABLE 6

| Summary of results of mouse immunogenicity study | | | | | | | | |
|---|---|---|---|---|---|---|---|---|
| Vaccine formulation | Stimulation Index | IL-4 [ng/ml] | IL-5 [ng/ml] | IL-10 [ng/ml] | IFN-γ [ng/ml] | ELISA titer (post dose 1) | ELISA titer (post dose 2) | ELISA titer (post dose 3) |
| GP95 (GPI-0100) | 15.1 ± 3.5 | 5.0 ± 0.5 | 10.9 ± 1.8 | 6.6 ± 1.0 | 5.8 ± 1.0 | <250 | 7325 | 9949 |
| GP95 (ISA51) | 10.6 ± 4.9 | 1.4 ± 0.1 | 2.1 ± 0.5 | 1.6 ± 0.4 | 5.5 ± 2.1 | <250 | 934 | 3384 |
| GPI-0100 control (GP stimulated) | 1.0 ± 0.1 | 0.02 ± 0.00 | 0.06 ± 0.00 | 0.04 ± 0.00 | 0.15 ± 0.01 | <250 | <250 | <250 |
| ISA51 control (GP stimulated) | 1.1 ± 0.2 | 0.01 ± 0.01 | 0.06 ± 0.00 | 0.04 ± 0.00 | 0.14 ± 0.01 | <250 | <250 | <250 |
| VP40 (GPI-0100) | 3.0 ± 0.3 | 7.0 ± 1.3 | 20.2 ± 1.0 | 11.8 ± 1.4 | 6.3 ± 2.0 | 441 | 18699 | 21767 |
| VP40 (ISA51) | 4.4 ± 1.0 | 2.3 ± 0.2 | 12.4 ± 2.5 | 8.8 ± 1.0 | 5.1 ± 0.4 | 275 | 5538 | 25866 |
| GPI-0100 control (VP40 stimulated) | 1.1 ± 0.2 | 0.01 ± 0.00 | 0.05 ± 0.00 | 0.04 ± 0.00 | 0.09 ± 0.03 | <250 | <250 | <250 |
| ISA51 control (VP40stimulated) | 0.9 ± 0.1 | 0.00 ± 0.00 | 0.05 ± 0.00 | 0.04 ± 0.01 | 0.22 ± 0.14 | <250 | <250 | <250 |
| VP24 (GPI-0100) | 6.2 ± 2.1 | 6.4 ± 0.9 | 23.8 ± 1.7 | 14.8 ± 1.7 | 5.4 ± 1.4 | <250 | 3764 | 7780 |
| VP24 (ISA51) | 2.2 ± 0.7 | 1.2 ± 0.3 | 9.5 ± 2.6 | 5.9 ± 1.4 | 6.6 ± 0.4 | <250 | 1521 | 7662 |
| GPI-0100 control (VP24 stimulated) | 1.0 ± 0.1 | 0.02 ± 0.00 | 0.08 ± 0.02 | 0.05 ± 0.01 | 0.33 ± 0.14 | <250 | <250 | <250 |
| ISA51 control (VP24 stimulated) | 0.9 ± 0.1 | 0.01 ± 0.01 | 0.06 ± 0.01 | 0.04 ± 0.00 | 0.16 ± 0.03 | <250 | <250 | <250 |

As described above, immune mouse sera from the first immunogenicity study were tested by ELISA using the recombinant proteins as coating antigens. In addition, the same sera were titered using irradiated Ebola virus particles as coating antigens. Table 7 compares the geometric mean titers of the highest dilution yielding an absorption value of 0.2 above background after color development.

TABLE 7

| Comparison of ELISA titers in the same immune mouse sera obtained using different coating antigens: | | | | | | |
|---|---|---|---|---|---|---|
| | Recombinant protein antigens | | | irradiated Ebola virus | | |
| | post dose 1 | post dose 2 | post dose 3 | post dose 1 | post dose 2 | post dose 3 |
| GP95 (GPI-0100) | 250 | 27858 | 64000 | <100 (33) | 1397 | 3363 |
| GP95 (ISA-51) | <250 | 6964 | 16000 | <100 (33) | 155 | 580 |
| VP24 (GPI-0100) | <250 | 16000 | 36758 | <100 (33) | <100 (33) | 51 |
| VP24 (ISA-51) | <250 | 9190 | 36758 | <100 (33) | 124 | 33 |
| VP40 (GPI-0100) | 2297 | 147033 | 256000 | 41 | 37710 | 30271 |
| VP40 (ISA-51) | 758 | 48503 | 256000 | 64 | 15659 | 30271 |

TABLE 7-continued

Comparison of ELISA titers in the same immune mouse sera obtained using different coating antigens:

| | Recombinant protein antigens | | | irradiated Ebola virus | | |
|---|---|---|---|---|---|---|
| | post dose 1 | post dose 2 | post dose 3 | post dose 1 | post dose 2 | post dose 3 |
| GPI-0100 control | <250 | <250 | <250 | <100 (33) | <100 (33) | 41 |
| ISA-51 control | <250 | <250 | <250 | <100 (33) | <100 (33) | <100 (33) |

The two methods yielded different relative titer values likely due to the different sources and composition of coating antigen. 0.375 μg of each individual recombinant protein (either GP95, VP40 or VP24) was applied per well resulting in a controlled amount of protein. In contrast, when irradiated virus was used as coating antigen, the relative amounts of each viral protein reflected the composition of the virus particles. VP40 is the major protein in virus particles. High titers in the assay can be attributed to its abundance of about 40% of the total virus protein. In contrast, GP is the major surface protein, but represents only 2-5% of the particle mass. Therefore, relatively less GP protein is contained in each virus-coated well, perhaps resulting in lower overall titers. Similarly, VP24 is only a minor component (2-5%) of virions and in addition resides exclusively inside the particle. It therefore would not be unexpected that anti-VP24 ELISA titers measured against whole virus would be lower than the anti-VP40 and anti-GP titers. The results show that immunization with Ebola proteins expressed in *Drosophila* S2 cells results in production of high titer antibodies that are reactive with intact viral particles.

Example 4

Optimization of Ebola Vaccine Formulations Based on Recombinant Proteins

The major vaccine candidate protein (GP95) was tested at 1, 3 or 9 μg formulated with three adjuvants (GPI-0100 (Hawaii Biotech, Inc.), CoVaccine HT® (CoVaccine, www.covaccine.com) and Ribi-700 (GlaxoSmithKline, Philadelphia, Pa.) while VP40 was tested only at 10 μg per dose using the same three adjuvants. 10 Balb/c mice per group were vaccinated three times at four-week intervals (Table 8). Tail bleeds were collected 2 weeks after the first and second immunizations. Three mice were splenectomized 4 days following the third dose, three on day seven. The remaining four mice from each group were terminally bled 14 days post third immunization.

TABLE 8

Dose/adjuvant formulation study groups:

| Group no. | Adjuvant | Immunogen | No. of mice | Formulation | Adm. |
|---|---|---|---|---|---|
| 1 | GPI-0100 | 1 μg GP95 | 10 | 250 μg of GPI-0100 is mixed with antigen and PBS | 2 sites s.c. |
| 2 | CoVaccine HT | 1 μg GP95 | 10 | 0.1 ml of CoVaccine HT is mixed with 0.1 ml of immunogen in PBS | 2 sites s.c. |
| 3 | RIBI R-700 | 1 μg GP95 | 10 | Prepare formulation according to manufacturer's instructions | 2 sites s.c. |
| 4 | GPI-0100 | 3 μg GP95 | 10 | 250 μg of GPI-0100 is mixed with antigen and PBS | 2 sites s.c. |
| 5 | CoVaccine HT | 3 μg GP95 | 10 | 0.1 ml of CoVaccine HT is mixed with 0.1 ml of immunogen in PBS | 2 sites s.c. |
| 6 | RIBI R-700 | 3 μg GP95 | 10 | Prepare formulation according to manufacturer's instructions | 2 sites s.c. |
| 7 | GPI-0100 | 9 μg GP95 | 10 | 250 μg of GPI-0100 is mixed with antigen and PBS | 2 sites s.c. |
| 8 | CoVaccine HT | 9 μg GP95 | 10 | 0.1 ml of CoVaccine HT is mixed with 0.1 ml of immunogen in PBS | 2 sites s.c. |
| 9 | RIBI R-700 | 9 μg GP95 | 10 | Prepare formulation according to manufacturer's instructions | 2 sites s.c. |
| 10 | GPI-0100 | 10 μg VP-40 | 10 | 250 μg of GPI-0100 is mixed with antigen and PBS | 2 sites s.c. |
| 11 | CoVaccine HT | 10 μg VP-40 | 10 | 0.1 ml of CoVaccine HT is mixed with 0.1 ml of immunogen in PBS | 2 sites s.c. |
| 12 | RIBI R-700 | 10 μg VP-40 | 10 | Prepare formulation according to manufacturer's instructions | 2 sites s.c. |
| 13 | GPI-0100 | NONE | 10 | 250 μg of GPI-0100 is mixed with PBS | 2 sites s.c. |
| 14 | CoVaccine HT | NONE | 10 | 0.1 ml of CoVaccine HT is mixed with 0.1 ml of PBS | 2 sites s.c. |
| 15 | RIBI R-700 | NONE | 10 | Prepare formulation according to manufacturer's instructions | 2 sites s.c. |

Analysis of antibodies raised (ELISA titers) of the combined dose/adjuvant study are shown in Table 9. Titers are expressed as the dilution yielding the half maximal absorption value (determined by using a sigmoidal curve fitting algorithm). Homologous antigen preparations (GP95 or VP40) from the same lots used for immunizations were used as coating antigens.

TABLE 9

Summary of ELISA titers from the dose/adjuvant study

| Vaccine formulation | Recombinant GP95 as coating antigen Post dose 1 | Post dose 2 | Post dose 3 | Recombinant VP40 as coating antigen Post dose 1 | Post dose 2 | Post dose 3 |
|---|---|---|---|---|---|---|
| 1 μg GP95 (250 μg GPI-0100) | <250 | 4097 | 24644 | ND | ND | ND |
| 3 μg GP95 (250 μg GPI-0100) | <250 | 6215 | 16577 | ND | ND | ND |
| 9 μg GP95 (250 μg GPI-0100) | <250 | 10403 | 18627 | ND | ND | ND |
| 1 μg GP95 (CoVaccine HT) | <250 | <250 | 1179 | ND | ND | ND |
| 3 μg GP95 (CoVaccine HT) | <250 | 581 | 7588 | ND | ND | ND |
| 9 μg GP95 (CoVaccine HT) | <250 | 1345 | 7297 | ND | ND | ND |
| 1 μg GP95 (Ribi R-700) | <250 | <250 | <250 | ND | ND | ND |
| 3 μg GP95 (Ribi R-700) | <250 | <250 | 696 | ND | ND | ND |
| 9 μg GP95 (Ribi R-700) | <250 | <250 | 2913 | ND | ND | ND |
| 10 μg VP40 (250 μg GPI-0100) | ND | ND | ND | 906 | 22732 | 57638 |
| 10 μg VP40 (CoVaccine HT) | ND | ND | ND | 697 | 9023 | 22689 |
| 10 μg VP40 (Ribi R-700) | ND | ND | ND | 157 | 9429 | 24045 |
| Control (250 μg GPI-0100) | <250 | <250 | <250 | <250 | <250 | <250 |
| Control (CoVaccine HT) | <250 | <250 | <250 | <250 | <250 | <250 |
| Control (Ribi R-700) | <250 | <250 | <250 | <250 | <250 | <250 |

*(ND: titer not determined)

Table 10 shows the cytokine secretion data obtained from antigen-stimulated immune splenocytes. It also lists the Stimulation Index expressed as the fold-increase of tritiated thymidine uptake in antigen-stimulated cells divided by unstimulated control cells of the same animal. Data from adjuvant-only control groups is included, stimulated with the antigen shown. Results shown are the mean values with standard deviation obtained using splenocyte preparations from three individual mice per group harvested on day 4 (upper value) and 7 (lower value) post 3$^{rd}$ dose of vaccine.

TABLE 10

Summary of Cellular Responses Elicited During the Dose/Adjuvant Study

| Vaccine formulation | Stimulation index | IL-4 [ng/ml] | IL-5 [ng/ml] | TNF-α [ng/ml] | IFN-γ [ng/ml] |
|---|---|---|---|---|---|
| 1 μg GP95 (250 μg GPI-0100) | 4.3 ± 3.6 | 0.9 ± 1.2 | 8.3 ± 1.2 | 1.0 ± 0.3 | 3.8 ± 2.2 |
| 3 μg GP95 (250 μg GPI-0100) | 6.5 ± 3.6 | 1.7 ± 1.8 | 7.4 ± 1.3 | 1.3 ± 0.7 | 4.6 ± 0.4 |
| 9 μg GP95 (250 μg GPI-0100) | 5.7 ± 3.3 | 1.3 ± 1.3 | 3.3 ± 2.9 | 1.2 ± 1.6 | 2.6 ± 2.5 |
| 1 μg GP95 (CoVaccine HT) | 9.7 ± 5.6 | 0.0 ± 0.0 | 2.8 ± 0.5 | 1.4 ± 0.1 | 3.4 ± 0.3 |
| 3 μg GP95 (CoVaccine HT) | 5.7 ± 0.8 | 0.0 ± 0.0 | 3.3 ± 1.2 | 1.4 ± 0.3 | 3.5 ± 0.7 |
| 9 μg GP95 (CoVaccine HT) | 6.1 ± 1.7 | 2.3 ± 3.4 | 3.9 ± 3.0 | 1.4 ± 1.0 | 3.4 ± 1.5 |
| 1 μg GP95 (Ribi R-700) | 1.8 ± 0.7 | 0.0 ± 0.0 | 0.3 ± 0.5 | 1.4 ± 1.0 | 2.8 ± 2.2 |
| 3 μg GP95 (Ribi R-700) | 33.0 ± 34.0 | 0.0 ± 0.0 | 0.3 ± 0.4 | 1.0 ± 1.6 | 1.7 ± 2.8 |
| 9 μg GP95 (Ribi R-700) | 18.7 ± 6.9 | 0.0 ± 0.0 | 0.1 ± 0.1 | 0.3 ± 0.3 | 0.3 ± 0.3 |
| Control (250 μg GPI-0100) GP95 stim. | 1.2 ± 0.5 | 0.0 ± 0.0 | 0.0 ± 0.0 | 0.0 ± 0.0 | 0.0 ± 0.0 |
| Control (CoVaccine HT) GP95 stimulated | 1.2 ± 0.5 | 0.0 ± 0.0 | 0.0 ± 0.0 | 0.0 ± 0.0 | 0.0 ± 0.0 |

TABLE 10-continued

Summary of Cellular Responses Elicited During the Dose/Adjuvant Study

| Vaccine formulation | Stimulation index | IL-4 [ng/ml] | IL-5 [ng/ml] | TNF-α [ng/ml] | IFN-γ [ng/ml] |
|---|---|---|---|---|---|
| Control (Ribi R-700) GP95 stimulated | 1.1 ± 0.2 | 0.0 ± 0.0 | 0.0 ± 0.0 | 0.0 ± 0.0 | 0.0 ± 0.0 |
| 10 μg VP40 (250 μg GPI-0100) | 2.9 ± 0.8 | 4.2 ± 3.6 | 6.2 ± 2.1 | 0.9 ± 0.7 | 1.9 ± 2.2 |
| 10 μg VP40 (CoVaccine HT) | 20.9 ± 7.9 | 3.7 ± 3.6 | 4.8 ± 2.6 | 0.7 ± 0.4 | 1.6 ± 0.4 |
| 10 μg VP40 (Ribi R-700) | 26.5 ± 15.0 | 0.0 ± 0.0 | 0.8 ± 1.5 | 0.0 ± 0.0 | 0.0 ± 0.0 |
| Control (GPI-0100) VP40 stim. | 1.2 ± 0.3 | 0.0 ± 0.0 | 0.0 ± 0.0 | 0.0 ± 0.0 | 0.0 ± 0.0 |
| Control (CoVaccine HT) VP40 stim. | 1.6 ± 0.5 | 0.0 ± 0.0 | 0.0 ± 0.0 | 0.0 ± 0.0 | 0.0 ± 0.0 |
| Control (Ribi R-700) VP40 stimulated | 1.4 ± 0.2 | 0.0 ± 0.0 | 0.0 ± 0.0 | 0.0 ± 0.0 | 0.0 ± 0.0 |

Overall the GPI-0100 adjuvant shows a strong advantage with both antigens compared to other formulations for both humoral and cellular responses. Based on the same immunological markers, CoVaccine HT appears to have a moderate effect. The responses elicited by formulations containing Ribi R-700 (especially based on cytokine responses) are the lowest. As seen in the previous immunogenicity study, the kinetics of the response to VP40 are more rapid compared to the other antigens.

Splenocytes from immunized mice receiving the leading vaccine formulations (GP95 and VP40 formulated with GPI-0100) harvested on day 4 post third dose were cultured at a final concentration of $2\times10^6$/ml in the presence (or absence) of either GP95 or VP40 antigens or Pokeweed mitogen (PWM) at final concentrations of 5 μg/ml for 18 hrs. Cells were then harvested, washed, and stained with fluorochrome-conjugated antibodies to stain for cell surface (CD3 or CD19) and activation markers (CD69), and then analyzed by flow cytometry.

The data shown in FIG. 10 demonstrates that the total percentage of CD 19+ B-cells stayed approximately the same regardless of the treatment (none, PWM, or antigen). Addition of Pokeweed mitogen activated (CD69+) about 40% of the cells in all mice tested. In contrast to the control groups (GPI-0100 only), the cells of the four mice immunized with recombinant Ebola antigens showed a substantial increase (five fold above background or more) in expression of surface activation marker CD69 in response to in vitro antigen stimulation. This suggests that the tested vaccine formulations induce strong cellular memory in vaccinated Balb/c mice.

Example 5

Protective Efficacy of Ebola Vaccine Candidates in the Mouse Challenge Model for Ebola Zaire Vaccine formulations containing 10 μg of either GP95, VP40, or VP24 as individual antigens or the mix of all three, unadjuvanted or in combination with the adjuvants GPI-0100, CoVaccine HT, Talabostat or PT-510 (both from Point Therapeutics, Inc., Boston, Mass.) were tested at USAMRIID in the mouse challenge model for protection against Ebola Zaire virus. GPI-0100 as well as CoVaccine HT were co-administered to animals in injectable formulations, while Talabostat (10 μg doses) and PT-510 (80 μg doses) were given by oral gavage on days −1, 0 and +1 relative to injection of antigen preparation (these animals received antigen preparations in PBS). Three doses of vaccine were administered subcutaneously in 4-week intervals and yielded high serum antibody titers in all vaccinated mice (table 11). VP40 showed excellent immunogenicity which can be seen in the ELISA titers raised by unadjuvanted formulations in groups 11 (even after one dose). GP95 alone (group 1) showed a similar immunogenicity as VP40 while VP24 without adjuvant is raising moderate ELISA antibody titers. The efficacy against virus challenge by i.p. injection of 100 pfu of mouse adapted Ebola virus approximately two weeks after the last dose is also shown in table 11. The column showing survivors lists animals that remained healthy for up to 20 days after challenge (when the experiment was terminated) and all surviving mice in groups 3, 4, 5, 16, 17, 18, 19 and 20 remained healthy throughout the study. In contrast, survivors in groups 1, 2, 8, 10 and 22 developed signs of disease for at least one day during the experiment. The vaccine formulation containing Ebola Zaire GP95 with CoVaccine HT as well as Talabostat or PT-510 completely protected all of the animals from both morbidity and mortality. Vaccine formulations containing all three antigens (GP95, VP40 and VP24) and either of the adjuvants showed the same level of protection. Furthermore, the combination of the three proteins without adjuvant, completely protected 9/10 animals. GP95 alone or formulated with GPI-0100 partially protected the animals against death but not morbidity. Interestingly, 6 of 10 animals in the group vaccinated with VP24 in formulation with CoVaccine HT as well as two animals receiving the antigens and oral doses of PT-510 survived the challenge. In contrast, all animals receiving VP40 alone with or without adjuvant succumbed to the infection despite very high levels of serum antibodies.

In combination, these results demonstrate that vaccine formulations containing recombinant Ebola subunit antigens produced from stably transformed insect cell lines have the potential to be used as efficacious vaccine products, even without adjuvant.

TABLE 11

Vaccine formulations and results of the mouse challenge study

| Group no. | Adjuvant | Immunogen | No. of mice | ELISA titers first | second | third | Day 20 (Jul. 05, 2005) dead | healthy | Percent alive |
|---|---|---|---|---|---|---|---|---|---|
| 1 | NONE | 10 μg GP95 | 10 | 155 | 520 | 14030 | 3 | 7 all were sick | 70% |
| 2 | GPI-0100 | 10 μg GP95 | 10 | 100 | 1251 | 19507 | 1 | 9 all were sick | 90% |
| 3 | CoVaccine HT | 10 μg GP95 | 10 | 300 | 58520 | 65315 | 0 | 10 | 100% |
| 4 | Talabostat | 10 μg GP95 | 10 | 90 | 14030 | 72900 | 0 | 9 | 100% |
| 5 | PT510 | 10 μg GP95 | 10 | 100 | 14913 | 72900 | 0 | 9 | 100% |
| 6 | NONE | 10 μg VP24 | 10 | 72 | 139 | 580 | 10 | 0 | 0% |
| 7 | GPI-0100 | 10 μg VP24 | 10 | 46 | 89 | 579 | 10 | 0 | 0% |
| 8 | CoVaccine HT | 10 μg VP24 | 10 | 155 | 27,122 | 37,710 | 4 | 6 all were sick | 60% |
| 9 | Talabostat | 10 μg VP24 | 10 | 193 | 1251 | 12570 | 10 | 0 | 0% |
| 10 | PT510 | 10 μg VP24 | 10 | 193 | 335 | 2419 | 8 | 2 (were sick) | 20% |
| 11 | NONE | 10 μg VP40 | 10 | 100 | 139 | 24,300 | 10 | 0 | 0% |
| 12 | GPI-0100 | 10 μg VP40 | 10 | 80 | 33,786 | 101,359 | 10 | 0 | 0% |
| 13 | CoVaccine HT | 10 μg VP40 | 10 | 3,754 | 1,415,647 | 1,968,300 | 10 | 0 | 0% |
| 14 | Talabostat | 10 μg VP40 | 10 | 269 | 647 | 244096 | 10 | 0 | 0% |
| 15 | PT510 | 10 μg VP40 | 10 | 193 | 580 | 339389 | 10 | 0 | 0% |
| 16 | NONE | mix | 10 | 155 | 900 | 21,772 | 1 | 9 | 90% |
| 17 | GPI-0100 | mix | 10 | 112 | 33,786 | 101,359 | 0 | 10 | 100% |
| 18 | CoVaccine HT | mix | 10 | 1,740 | 378,800 | 656,100 | 0 | 10 | 100% |
| 19 | Talabostat | mix | 10 | 235 | 8100 | 134213 | 0 | 9 | 100% |
| 20 | PT510 | mix | 10 | 128 | 4971 | 93058 | 0 | 9 | 100% |
| 21 | NONE | NONE | 9 | 64 | 72 | 72 | 9 | 0 | 0% |
| 22 | GPI-0100 | NONE | 10 | 51 | 46 | 57 | 9 | 1 Was sick | 10% |
| 23 | CoVaccine HT | NONE | 9 | 128 | 208 | 266 | 9 | 0 | 0% |
| 24 | Talabostat | NONE | 10 | 100 | 111 | 139 | 10 | 0 | 0% |
| 25 | PT510 | NONE | 10 | 125 | 100 | 112 | 10 | 0 | 0% |

We claim:

1. A composition comprising a recombinant *Drosophila* cell, wherein the cell is stably transformed with at least one expression vector encoding at least one Filovirus polypeptide wherein the polypeptide comprises a GP95 polypeptide or wherein the polypeptide comprises a truncated GPFL polypeptide, which truncated GPFL polypeptide is soluble and secretable and lacks a C-terminal transmembrane anchor.

2. The composition of claim 1 wherein the *Drosophila* cell is a *Drosophila melanogaster* cell.

3. The composition of claim 2, wherein the *Drosophila* cell is a Schneider 2 (S2) cell.

4. The composition of claim 1, wherein the expression vector comprises a nucleic acid sequence selected from the group consisting of: SEQ ID NO: 2, SEQ ID NO: 3, SEQ ID NO: 5, SEQ ID NO: 6, SEQ ID NO: 8, and SEQ ID NO: 9.

5. The composition of claim 1, wherein the Filovirus is selected from the group consisting of: Ebola Zaire, Ebola Sudan, Ebola Ivory-Coast, Ebola Reston, Marburg Musoke, Marburg Angola, and Marburg Popp.

6. The composition of claim 1, wherein the polypeptide is expressed by the cell.

7. The composition of claim 1, wherein the polypeptide further comprises a secretion signal.

8. The composition of claim 1, wherein the polypeptide comprises an amino acid sequence selected from the group consisting of: SEQ ID NO: 1, SEQ ID NO: 4, and SEQ NO: 7.

9. The composition of claim 1, wherein the truncated GPFL polypeptide comprises at least 95% of the GPFL polypeptide.

10. The composition of claim 1, wherein the polypeptide is immunogenic.

11. The composition of claim 1, wherein the polypeptide is glycosylated.

12. The composition of claim 11, wherein the polypeptide is glycosylated by the cell.

13. The composition of claim 1 or claim 11, wherein the polypeptide is recognized by monoclonal antibody 13C6-1-1.

14. The composition of claim 1, wherein the composition comprises a cell culture.

* * * * *

SEQUENCE LISTING

<160> NUMBER OF SEQ ID NOS: 21

<210> SEQ ID NO 1
<211> LENGTH: 617
<212> TYPE: PRT
<213> ORGANISM: Ebola Zaire Virus

<400> SEQUENCE: 1

Arg Ser Ile Pro Leu Gly Val Ile His Asn Ser Thr Leu Gln Val Ser
1 5 10 15

Asp Val Asp Lys Leu Val Cys Arg Asp Lys Leu Ser Ser Thr Asn Gln
20 25 30

Leu Arg Ser Val Gly Leu Asn Leu Glu Gly Asn Gly Val Ala Thr Asp
35 40 45

Val Pro Ser Ala Thr Lys Arg Trp Gly Phe Arg Ser Gly Val Pro Pro
50 55 60

Lys Val Val Asn Tyr Glu Ala Gly Glu Trp Ala Glu Asn Cys Tyr Asn
65 70 75 80

Leu Glu Ile Lys Lys Pro Asp Gly Ser Glu Cys Leu Pro Ala Ala Pro
85 90 95

Asp Gly Ile Arg Gly Phe Pro Arg Cys Arg Tyr Val His Lys Val Ser
100 105 110

```
Gly Thr Gly Pro Cys Ala Gly Asp Phe Ala Phe His Lys Glu Gly Ala
        115                 120                 125

Phe Phe Leu Tyr Asp Arg Leu Ala Ser Thr Val Ile Tyr Arg Gly Thr
    130                 135                 140

Thr Phe Ala Glu Gly Val Val Ala Phe Leu Ile Leu Pro Gln Ala Lys
145                 150                 155                 160

Lys Asp Phe Phe Ser Ser His Pro Leu Arg Glu Pro Val Asn Ala Thr
                165                 170                 175

Glu Asp Pro Ser Ser Gly Tyr Tyr Ser Thr Thr Ile Arg Tyr Gln Ala
            180                 185                 190

Thr Gly Phe Gly Thr Asn Glu Thr Glu Tyr Leu Phe Glu Val Asp Asn
        195                 200                 205

Leu Thr Tyr Val Gln Leu Glu Ser Arg Phe Thr Pro Gln Phe Leu Leu
    210                 215                 220

Gln Leu Asn Glu Thr Ile Tyr Thr Ser Gly Lys Arg Ser Asn Thr Thr
225                 230                 235                 240

Gly Lys Leu Ile Trp Lys Val Asn Pro Glu Ile Asp Thr Thr Ile Gly
                245                 250                 255

Glu Trp Ala Phe Trp Glu Thr Lys Lys Asn Leu Thr Arg Lys Ile Arg
            260                 265                 270

Ser Glu Glu Leu Ser Phe Thr Val Val Ser Asn Gly Ala Lys Asn Ile
        275                 280                 285

Ser Gly Gln Ser Pro Ala Arg Thr Ser Ser Asp Pro Gly Thr Asn Thr
    290                 295                 300

Thr Thr Glu Asp His Lys Ile Met Ala Ser Glu Asn Ser Ser Ala Met
305                 310                 315                 320

Val Gln Val His Ser Gln Gly Arg Glu Ala Ala Val Ser His Leu Thr
                325                 330                 335

Thr Leu Ala Thr Ile Ser Thr Ser Pro Gln Ser Leu Thr Thr Lys Pro
            340                 345                 350

Gly Pro Asp Asn Ser Thr His Asn Thr Pro Val Tyr Lys Leu Asp Ile
        355                 360                 365

Ser Glu Ala Thr Gln Val Glu Gln His His Arg Arg Thr Asp Asn Asp
    370                 375                 380

Ser Thr Ala Ser Asp Thr Pro Ser Ala Thr Thr Ala Ala Gly Pro Pro
385                 390                 395                 400

Lys Ala Glu Asn Thr Asn Thr Ser Lys Ser Thr Asp Phe Leu Asp Pro
                405                 410                 415

Ala Thr Thr Thr Ser Pro Gln Asn His Ser Glu Thr Ala Gly Asn Asn
            420                 425                 430

Asn Thr His His Gln Asp Thr Gly Glu Glu Ser Ala Ser Ser Gly Lys
        435                 440                 445

Leu Gly Leu Ile Thr Asn Thr Ile Ala Gly Val Ala Gly Leu Ile Thr
    450                 455                 460

Gly Gly Arg Arg Thr Arg Arg Glu Ala Ile Val Asn Ala Gln Pro Lys
465                 470                 475                 480

Cys Asn Pro Asn Leu His Tyr Trp Thr Thr Gln Asp Glu Gly Ala Ala
                485                 490                 495

Ile Gly Leu Ala Trp Ile Pro Tyr Phe Gly Pro Ala Ala Glu Gly Ile
            500                 505                 510

Tyr Ile Glu Gly Leu Met His Asn Gln Asp Gly Leu Ile Cys Gly Leu
        515                 520                 525

Arg Gln Leu Ala Asn Glu Thr Thr Gln Ala Leu Gln Leu Phe Leu Arg
    530                 535                 540
```

```
Ala Thr Thr Glu Leu Arg Thr Phe Ser Ile Leu Asn Arg Lys Ala Ile
545                 550                 555                 560

Asp Phe Leu Leu Gln Arg Trp Gly Gly Thr Cys His Ile Leu Gly Pro
                565                 570                 575

Asp Cys Cys Ile Glu Pro His Asp Trp Thr Lys Asn Ile Thr Asp Lys
            580                 585                 590

Ile Asp Gln Ile Ile His Asp Phe Val Asp Lys Thr Leu Pro Asp Gln
        595                 600                 605

Gly Asp Asn Asp Asn Trp Trp Thr Gly
    610                 615


<210> SEQ ID NO 2
<211> LENGTH: 1875
<212> TYPE: DNA
<213> ORGANISM: Ebola Zaire Virus

<400> SEQUENCE: 2

acgtacagat ctatcccact tggagtcatc cacaatagca cattacaggt tagtgatgtc      60

gacaaactag tttgtcgtga caaactgtca tccacaaatc aattgagatc agttggactg     120

aatctcgaag ggaatggagt ggcaactgac gtgccatctg caactaaaag atggggcttc     180

aggtccggtg tcccaccaaa ggtggtcaat tatgaagctg gtgaatgggc tgaaaactgc     240

tacaatcttg aaatcaaaaa acctgacggg agtgagtgtc taccagcagc gccagacggg     300

attcggggct tcccccggtg ccggtatgtg cacaaagtat caggaacggg accgtgtgcc     360

ggagactttg ccttccataa agagggtgct ttcttcctgt atgatcgact tgcttccaca     420

gttatctacc gaggaacgac tttcgctgaa ggtgtcgttg catttctgat actgccccaa     480

gctaagaagg acttcttcag ctcacacccc ttgagagagc cggtcaatgc aacggaggac     540

ccgtctagtg gctactattc taccacaatt agatatcagg ctaccggttt tggaaccaat     600

gagacagagt acttgttcga ggttgacaat ttgacctacg tccaacttga atcaagattc     660

acaccacagt ttctgctcca gctgaatgag acaatatata caagtgggaa aaggagcaat     720

accacgggaa aactaatttg gaaggtcaac cccgaaattg atacaacaat cggggagtgg     780

gccttctggg aaactaaaaa aaacctcact agaaaaattc gcagtgaaga gttgtctttc     840

acagttgtat caaacggagc caaaaacatc agtggtcaga gtccggcgcg aacttcttcc     900

gacccaggga ccaacacaac aactgaagac cacaaaatca tggcttcaga aaattcctct     960

gcaatggttc aagtgcacag tcaaggaagg gaagctgcag tgtcgcatct aacaaccctt    1020

gccacaatct ccacgagtcc ccaatccctc acaaccaaac caggtccgga caacagcacc    1080

cataatacac ccgtgtataa acttgacatc tctgaggcaa ctcaagttga acaacatcac    1140

cgcagaacag acaacgacag cacagcctcc gacactccct ctgccacgac cgcagccgga    1200

cccccaaaag cagagaacac caacacgagc aagagcactg acttcctgga ccccgccacc    1260

acaacaagtc cccaaaacca cagcgagacc gctggcaaca acaacactca tcaccaagat    1320

accggagaag agagtgccag cagcgggaag ctaggcttaa ttaccaatac tattgctgga    1380

gtcgcaggac tgatcacagg cgggagaaga actcgaagag aagcaattgt caatgctcaa    1440

cccaaatgca accctaattt acattactgg actactcagg atgaaggtgc tgcaatcgga    1500

ctggcctgga taccatattt cgggccagca gccgagggaa tttacataga ggggctaatg    1560

cacaatcaag atggtttaat ctgtgggttg agacagctgg ccaacgagac gactcaagct    1620

cttcaactgt tcctgagagc cacaactgag ctacgcacct tttcaatcct caaccgtaag    1680
```

```
gcaattgatt tcttgctgca gcgatggggc ggcacatgcc acattctggg accggactgc   1740

tgtatcgaac cacatgattg gaccaagaac ataacagaca aaattgatca gattattcat   1800

gattttgttg ataaaaccct tccggaccag ggggacaatg acaattggtg gacaggatag   1860

taactcgagg tacgt                                                    1875


<210> SEQ ID NO 3
<211> LENGTH: 1851
<212> TYPE: DNA
<213> ORGANISM: Ebola Zaire Virus

<400> SEQUENCE: 3

atcccacttg gagtcatcca caatagcaca ttacaggtta gtgatgtcga caaactagtt     60

tgtcgtgaca aactgtcatc cacaaatcaa ttgagatcag ttggactgaa tctcgaaggg    120

aatggagtgg caactgacgt gccatctgca actaaaagat ggggcttcag gtccggtgtc    180

ccaccaaagg tggtcaatta tgaagctggt gaatgggctg aaaactgcta caatcttgaa    240

atcaaaaaac ctgacgggag tgagtgtcta ccagcagcgc cagacgggat tcggggcttc    300

ccccggtgcc ggtatgtgca caaagtatca ggaacgggac cgtgtgccgg agactttgcc    360

ttccataaag agggtgcttt cttcctgtat gatcgacttg cttccacagt tatctaccga    420

ggaacgactt tcgctgaagg tgtcgttgca tttctgatac tgccccaagc taagaaggac    480

ttcttcagct cacacccctt gagagagccg gtcaatgcaa cggaggaccc gtctagtggc    540

tactattcta ccacaattag atatcaggct accggttttg gaaccaatga gacagagtac    600

ttgttcgagg ttgacaattt gacctacgtc caacttgaat caagattcac accacagttt    660

ctgctccagc tgaatgagac aatatataca agtgggaaaa ggagcaatac cacgggaaaa    720

ctaatttgga aggtcaaccc cgaaattgat acaacaatcg gggagtgggc cttctgggaa    780

actaaaaaaa acctcactag aaaaattcgc agtgaagagt tgtctttcac agttgtatca    840

aacggagcca aaaacatcag tggtcagagt ccggcgcgaa cttcttccga cccagggacc    900

aacacaacaa ctgaagacca caaaatcatg gcttcagaaa attcctctgc aatggttcaa    960

gtgcacagtc aaggaaggga agctgcagtg tcgcatctaa caacccttgc cacaatctcc   1020

acgagtcccc aatccctcac aaccaaacca ggtccggaca acagcaccca taatacaccc   1080

gtgtataaac ttgacatctc tgaggcaact caagttgaac aacatcaccg cagaacagac   1140

aacgacagca cagcctccga cactccctct gccacgaccg cagccggacc cccaaaagca   1200

gagaacacca acacgagcaa gagcactgac ttcctggacc ccgccaccac aacaagtccc   1260

caaaaccaca gcgagaccgc tggcaacaac aacactcatc accaagatac cggagaagag   1320

agtgccagca gcgggaagct aggcttaatt accaatacta ttgctggagt cgcaggactg   1380

atcacaggcg ggagaagaac tcgaagagaa gcaattgtca atgctcaacc caaatgcaac   1440

cctaatttac attactggac tactcaggat gaaggtgctg caatcggact ggcctggata   1500

ccatatttcg ggccagcagc cgagggaatt tacatagagg ggctaatgca caatcaagat   1560

ggtttaatct gtgggttgag acagctggcc aacgagacga ctcaagctct tcaactgttc   1620

ctgagagcca caactgagct acgcaccttt tcaatcctca accgtaaggc aattgatttc   1680

ttgctgcagc gatggggcgg cacatgccac attctgggac cggactgctg tatcgaacca   1740

catgattgga ccaagaacat aacagacaaa attgatcaga ttattcatga ttttgttgat   1800

aaaacccttc cggaccaggg ggacaatgac aattggtgga caggatagta a            1851


<210> SEQ ID NO 4
```

```
<211> LENGTH: 619
<212> TYPE: PRT
<213> ORGANISM: Ebola Sudan Virus

<400> SEQUENCE: 4

Arg Ser Pro Trp Met Pro Leu Gly Val Val Thr Asn Ser Thr Leu Glu
1               5                   10                  15

Val Thr Glu Ile Asp Gln Leu Val Cys Lys Asp His Leu Ala Ser Thr
            20                  25                  30

Asp Gln Leu Lys Ser Val Gly Leu Asn Leu Glu Gly Ser Gly Val Ser
        35                  40                  45

Thr Asp Ile Pro Ser Ala Thr Lys Arg Trp Gly Phe Arg Ser Gly Val
    50                  55                  60

Pro Pro Lys Val Val Ser Tyr Glu Ala Gly Glu Trp Ala Glu Asn Cys
65                  70                  75                  80

Tyr Asn Leu Glu Ile Lys Lys Pro Asp Gly Ser Glu Cys Leu Pro Pro
                85                  90                  95

Pro Pro Asp Gly Val Arg Gly Phe Pro Arg Cys Arg Tyr Val His Lys
            100                 105                 110

Ala Gln Gly Thr Gly Pro Cys Pro Gly Asp Tyr Ala Phe His Lys Asp
        115                 120                 125

Gly Ala Phe Phe Leu Tyr Asp Arg Leu Ala Ser Thr Val Ile Tyr Arg
    130                 135                 140

Gly Val Asn Phe Ala Glu Gly Val Ile Ala Phe Leu Ile Leu Ala Lys
145                 150                 155                 160

Pro Lys Glu Thr Phe Leu Gln Ser Pro Pro Ile Arg Glu Ala Val Asn
                165                 170                 175

Tyr Thr Glu Asn Thr Ser Ser Tyr Tyr Ala Thr Ser Tyr Leu Glu Tyr
            180                 185                 190

Glu Ile Glu Asn Phe Gly Ala Gln His Ser Thr Thr Leu Phe Lys Ile
        195                 200                 205

Asp Asn Asn Thr Phe Val Arg Leu Asp Arg Pro His Thr Pro Gln Phe
    210                 215                 220

Leu Phe Gln Leu Asn Asp Thr Ile His Leu His Gln Gln Leu Ser Asn
225                 230                 235                 240

Thr Thr Gly Arg Leu Ile Trp Thr Leu Asp Ala Asn Ile Asn Ala Asp
                245                 250                 255

Ile Gly Glu Trp Ala Phe Trp Glu Asn Lys Lys Asn Leu Ser Glu Gln
            260                 265                 270

Leu Arg Gly Glu Glu Leu Ser Phe Glu Ala Leu Ser Leu Asn Glu Thr
        275                 280                 285

Glu Asp Asp Asp Ala Ala Ser Ser Arg Ile Thr Lys Gly Arg Ile Ser
    290                 295                 300

Asp Arg Ala Thr Arg Lys Tyr Ser Asp Leu Val Pro Lys Asn Ser Pro
305                 310                 315                 320

Gly Met Val Pro Leu His Ile Pro Glu Gly Glu Thr Thr Leu Pro Ser
                325                 330                 335

Gln Asn Ser Thr Glu Gly Arg Arg Val Gly Val Asn Thr Gln Glu Thr
            340                 345                 350

Ile Thr Glu Thr Ala Ala Thr Ile Ile Gly Thr Asn Gly Asn His Met
        355                 360                 365

Gln Ile Ser Thr Ile Gly Ile Arg Pro Ser Ser Ser Gln Ile Pro Ser
    370                 375                 380

Ser Ser Pro Thr Thr Ala Pro Ser Pro Glu Ala Gln Thr Pro Thr Thr
385                 390                 395                 400
```

```
His Thr Ser Gly Pro Ser Val Met Ala Thr Glu Glu Pro Thr Thr Pro
                405                 410                 415

Pro Gly Ser Ser Pro Gly Pro Thr Thr Glu Ala Pro Thr Leu Thr Thr
            420                 425                 430

Pro Glu Asn Ile Thr Thr Ala Val Lys Thr Val Leu Pro Gln Glu Ser
        435                 440                 445

Thr Ser Asn Gly Leu Ile Thr Ser Thr Val Thr Gly Ile Leu Gly Ser
    450                 455                 460

Leu Gly Leu Arg Lys Arg Ser Arg Arg Gln Thr Asn Thr Lys Ala Thr
465                 470                 475                 480

Gly Lys Cys Asn Pro Asn Leu His Tyr Trp Thr Ala Gln Glu Gln His
                485                 490                 495

Asn Ala Ala Gly Ile Ala Trp Ile Pro Tyr Phe Gly Pro Gly Ala Glu
            500                 505                 510

Gly Ile Tyr Thr Glu Gly Leu Met His Asn Gln Asn Ala Leu Val Cys
        515                 520                 525

Gly Leu Arg Gln Leu Ala Asn Glu Thr Thr Gln Ala Leu Gln Leu Phe
    530                 535                 540

Leu Arg Ala Thr Thr Glu Leu Arg Thr Tyr Thr Ile Leu Asn Arg Lys
545                 550                 555                 560

Ala Ile Asp Phe Leu Leu Arg Arg Trp Gly Gly Thr Cys Arg Ile Leu
                565                 570                 575

Gly Pro Asp Cys Cys Ile Glu Pro His Asp Trp Thr Lys Asn Ile Thr
            580                 585                 590

Asp Lys Ile Asn Gln Ile Ile His Asp Phe Ile Asp Asn Pro Leu Pro
        595                 600                 605

Asn Gln Asp Asn Asp Asp Asn Trp Trp Thr Gly
    610                 615
```

```
<210> SEQ ID NO 5
<211> LENGTH: 1873
<212> TYPE: DNA
<213> ORGANISM: Ebola Sudan Virus

<400> SEQUENCE: 5

aggttccatg gatgcctttg ggtgttgtga ctaacagcac tttagaagta acagagattg     60

accagctagt ctgcaaggat catcttgcat ctactgacca gctgaaatca gttggtctca    120

acctcgaggg gagcggagta tctactgata tcccatctgc aacaaagcgt tggggcttca    180

gatctggtgt tcctcccaag gtggtcagct atgaagcggg agaatgggct gaaaattgct    240

acaatcttga aataaagaag ccggacggga gcgaatgctt acccccaccg ccagatggtg    300

tcagaggctt tccaaggtgc cgctatgttc acaaagccca aggaaccggg ccctgcccag    360

gtgactacgc ctttcacaag gatggagctt tcttcctcta tgacaggctg gcttcaactg    420

taatttacag aggagtcaat tttgctgagg ggtaattgc attcttgata ttggctaaac     480

caaaagaaac gttccttcag tcaccccca ttcgagaggc agtaaactac actgaaaata     540

catcaagtta ttatgccaca tcctacttgg agtatgaaat cgaaaatttt ggtgctcaac    600

actccacgac ccttttcaaa attgacaata atacttttgt tcgtctggac aggccccaca    660

cgcctcagtt ccttttccag ctgaatgata ccattcacct tcaccaacag ttgagtaata    720

caactgggag actaatttgg acactagatg ctaatatcaa tgctgatatt ggtgaatggg    780

ctttttggga aaataaaaaa aatctctccg aacaactacg tggagaagag ctgtctttcg    840

aagctttatc gctcaacgag acagaagacg atgatgcggc atcgtcgaga attacaaagg    900
```

```
gaagaatctc cgaccgggcc accaggaagt attcggacct ggttccaaag aattcccctg    960
ggatggttcc attgcacata ccagaagggg aaacaacatt gccgtctcag aattcgacag   1020
aaggtcgaag agtaggtgtg aacactcagg agaccattac agagacagct gcaacaatta   1080
taggcactaa cggcaaccat atgcagatct ccaccatcgg gataagaccg agctccagcc   1140
aaatcccgag ttcctcaccg accacggcac caagccctga ggctcagacc cccacaaccc   1200
acacatcagg tccatcagtg atggccaccg aggaaccaac aacaccaccg ggaagctccc   1260
ccggcccaac aacagaagca cccactctca ccaccccaga aaatataaca acagcggtta   1320
aaactgtcct gccacaggag tccacaagca acggtctaat aacttcaaca gtaacaggga   1380
ttcttgggag tcttgggctt cgaaaacgca gcagaagaca aactaacacc aaagccacgg   1440
gtaagtgcaa tcccaactta cactactgga ctgcacaaga acaacataat gctgctggga   1500
ttgcctggat cccgtacttt ggaccgggtg cggaaggcat atacactgaa ggcctgatgc   1560
ataaccaaaa tgccttagtc tgtggactta ggcaacttgc aaatgaaaca actcaagctc   1620
tgcagctttt cttaagagcc acaacggagc tgcggacata taccatactc aataggaagg   1680
ccatagattt ccttctgcga cgatggggcg ggacatgcag gatcctggga ccagattgtt   1740
gcattgagcc acatgattgg acaaaaaaca tcactgataa aatcaaccaa atcatccatg   1800
atttcatcga caacccctta cctaatcagg ataatgatga taattggtgg acgggctagt   1860
aagtcgacaa cct                                                      1873
```

<210> SEQ ID NO 6
<211> LENGTH: 1845
<212> TYPE: DNA
<213> ORGANISM: Ebola Sudan Virus

<400> SEQUENCE: 6

```
atgcctttgg gtgttgtgac taacagcact ttagaagtaa cagagattga ccagctagtc     60
tgcaaggatc atcttgcatc tactgaccag ctgaaatcag ttggtctcaa cctcgagggg    120
agcggagtat ctactgatat cccatctgca acaaagcgtt ggggcttcag atctggtgtt    180
cctcccaagg tggtcagcta tgaagcggga gaatgggctg aaaattgcta caatcttgaa    240
ataaagaagc cggacgggag cgaatgctta cccccaccgc cagatggtgt cagaggcttt    300
ccaaggtgcc gctatgttca caaagcccaa ggaaccgggc cctgcccagg tgactacgcc    360
tttcacaagg atggagcttt cttcctctat gacaggctgg cttcaactgt aatttacaga    420
ggagtcaatt ttgctgaggg ggtaattgca ttcttgatat tggctaaacc aaaagaaacg    480
ttccttcagt cacccccccat tcgagaggca gtaaactaca ctgaaaatac atcaagttat    540
tatgccacat cctacttgga gtatgaaatc gaaaatttg gtgctcaaca ctccacgacc    600
cttttcaaaa ttgacaataa tacttttgtt cgtctggaca ggccccacac gcctcagttc    660
cttttccagc tgaatgatac cattcacctt caccaacagt tgagtaatac aactgggaga    720
ctaatttgga cactagatgc taatatcaat gctgatattg gtgaatgggc tttttgggaa    780
aataaaaaaa atctctccga acaactacgt ggagaagagc tgtctttcga agctttatcg    840
ctcaacgaga cagaagacga tgatgcggca tcgtcgagaa ttacaaaggg aagaatctcc    900
gaccgggcca ccaggaagta ttcggacctg gttccaaaga attcccctgg gatggttcca    960
ttgcacatac cagaagggga aacaacattg ccgtctcaga attcgacaga aggtcgaaga   1020
gtaggtgtga acactcagga gaccattaca gagacagctg caacaattat aggcactaac   1080
ggcaaccata tgcagatctc caccatcggg ataagaccga gctccagcca aatcccgagt   1140
```

```
tcctcaccga ccacggcacc aagccctgag gctcagaccc ccacaaccca cacatcaggt   1200

ccatcagtga tggccaccga ggaaccaaca acaccaccgg gaagctcccc cggcccaaca   1260

acagaagcac ccactctcac caccccagaa aatataacaa cagcggttaa aactgtcctg   1320

ccacaggagt ccacaagcaa cggtctaata acttcaacag taacagggat tcttgggagt   1380

cttgggcttc gaaaacgcag cagaagacaa actaacacca aagccacggg taagtgcaat   1440

cccaacttac actactggac tgcacaagaa caacataatg ctgctgggat tgcctggatc   1500

ccgtactttg gaccgggtgc ggaaggcata tacactgaag gcctgatgca taaccaaaat   1560

gccttagtct gtggacttag gcaacttgca aatgaaacaa ctcaagctct gcagcttttc   1620

ttaagagcca caacggagct gcggacatat accatactca ataggaaggc catagatttc   1680

cttctgcgac gatggggcgg gacatgcagg atcctgggac cagattgttg cattgagcca   1740

catgattgga caaaaaacat cactgataaa atcaaccaaa tcatccatga tttcatcgac   1800

aaccccttac ctaatcagga taatgatgat aattggtgga cgggc                   1845
```

<210> SEQ ID NO 7
<211> LENGTH: 631
<212> TYPE: PRT
<213> ORGANISM: Marburg Virus

<400> SEQUENCE: 7

```
Arg Ser Leu Pro Ile Leu Glu Ile Ala Ser Asn Asn Gln Pro Gln Asn
1               5                   10                  15

Val Asp Ser Val Cys Ser Gly Thr Leu Gln Lys Thr Glu Asp Val His
            20                  25                  30

Leu Met Gly Phe Thr Leu Ser Gly Gln Lys Val Ala Asp Ser Pro Leu
        35                  40                  45

Glu Ala Ser Lys Arg Trp Ala Phe Arg Thr Gly Val Pro Pro Lys Asn
    50                  55                  60

Val Glu Tyr Thr Glu Gly Glu Glu Ala Lys Thr Cys Tyr Asn Ile Ser
65                  70                  75                  80

Val Thr Asp Pro Ser Gly Lys Ser Leu Leu Leu Asp Pro Pro Thr Asn
                85                  90                  95

Ile Arg Asp Tyr Pro Lys Cys Lys Thr Ile His His Ile Gln Gly Gln
            100                 105                 110

Asn Pro His Ala Gln Gly Ile Ala Leu His Leu Trp Gly Ala Phe Phe
        115                 120                 125

Leu Tyr Asp Arg Ile Ala Ser Thr Thr Met Tyr Arg Gly Arg Val Phe
    130                 135                 140

Thr Glu Gly Asn Ile Ala Ala Met Ile Val Asn Lys Thr Val His Lys
145                 150                 155                 160

Met Ile Phe Ser Arg Gln Gly Gln Gly Tyr Arg His Met Asn Leu Thr
                165                 170                 175

Ser Thr Asn Lys Tyr Trp Thr Ser Asn Asn Gly Thr Gln Thr Asn Asp
            180                 185                 190

Thr Gly Cys Phe Gly Ala Leu Gln Glu Tyr Asn Ser Thr Lys Asn Gln
        195                 200                 205

Thr Cys Ala Pro Ser Lys Ile Pro Ser Pro Leu Pro Thr Ala Arg Pro
    210                 215                 220

Glu Ile Lys Pro Thr Ser Thr Pro Thr Asp Ala Thr Thr Leu Asn Thr
225                 230                 235                 240

Thr Asp Pro Asn Asn Asp Asp Glu Asp Leu Ile Thr Ser Gly Ser Gly
                245                 250                 255
```

```
Ser Gly Glu Gln Glu Pro Tyr Thr Thr Ser Asp Ala Val Thr Lys Gln
            260                 265                 270

Gly Leu Ser Ser Thr Met Pro Pro Thr Pro Ser Pro Gln Pro Ser Thr
        275                 280                 285

Pro Gln Gln Glu Gly Asn Asn Thr Asp His Ser Gln Gly Thr Val Thr
    290                 295                 300

Glu Pro Asn Lys Thr Asn Thr Thr Ala Gln Pro Ser Met Pro Pro His
305                 310                 315                 320

Asn Thr Thr Ala Ile Ser Thr Asn Asn Thr Ser Lys Asn Asn Phe Ser
                325                 330                 335

Thr Leu Ser Val Ser Leu Gln Asn Thr Thr Asn Tyr Asp Thr Gln Ser
            340                 345                 350

Thr Ala Thr Glu Asn Glu Gln Thr Ser Ala Pro Ser Lys Thr Thr Leu
        355                 360                 365

Pro Pro Thr Gly Asn Leu Thr Thr Ala Lys Ser Thr Asn Asn Thr Lys
    370                 375                 380

Gly Pro Thr Thr Thr Ala Pro Asn Met Thr Asn Gly His Leu Thr Ser
385                 390                 395                 400

Pro Ser Pro Thr Pro Asn Pro Thr Thr Gln His Leu Val Tyr Phe Arg
                405                 410                 415

Lys Lys Arg Ser Ile Leu Trp Arg Glu Gly Asp Met Phe Pro Phe Leu
            420                 425                 430

Asp Gly Leu Ile Asn Ala Pro Ile Asp Phe Asp Pro Val Pro Asn Thr
        435                 440                 445

Lys Thr Ile Phe Asp Glu Ser Ser Ser Ser Gly Ala Ser Ala Glu Glu
    450                 455                 460

Asp Gln His Ala Ser Pro Asn Ile Ser Leu Thr Leu Ser Tyr Phe Pro
465                 470                 475                 480

Asn Ile Asn Glu Asn Thr Ala Tyr Ser Gly Glu Asn Glu Asn Asp Cys
                485                 490                 495

Asp Ala Glu Leu Arg Ile Trp Ser Val Gln Glu Asp Asp Leu Ala Ala
            500                 505                 510

Gly Leu Ser Trp Ile Pro Phe Phe Gly Pro Gly Ile Glu Gly Leu Tyr
        515                 520                 525

Thr Ala Gly Leu Ile Lys Asn Gln Asn Asn Leu Val Cys Arg Leu Arg
    530                 535                 540

Arg Leu Ala Asn Gln Thr Ala Lys Ser Leu Glu Leu Leu Leu Arg Val
545                 550                 555                 560

Thr Thr Glu Glu Arg Thr Phe Ser Leu Ile Asn Arg His Ala Ile Asp
                565                 570                 575

Phe Leu Leu Thr Arg Trp Gly Gly Thr Cys Lys Val Leu Gly Pro Asp
            580                 585                 590

Cys Cys Ile Gly Ile Glu Asp Leu Ser Arg Asn Ile Ser Glu Gln Ile
        595                 600                 605

Asp Gln Ile Lys Lys Asp Glu Gln Lys Glu Gly Thr Gly Trp Gly Leu
    610                 615                 620

Gly Gly Lys Trp Trp Thr Ser
625                 630
```

<210> SEQ ID NO 8
<211> LENGTH: 1915
<212> TYPE: DNA
<213> ORGANISM: Marburg Virus

<400> SEQUENCE: 8

```
aggttagatc tctccctatt ttagagatag ctagtaacaa tcaaccccaa aatgtggatt     60
cggtatgctc cggaactctc cagaagacag aagatgtcca tctgatggga ttcacactga    120
gtgggcaaaa agttgctgat tcccctttgg aggcatccaa gcgatgggct ttcaggacag    180
gtgtacctcc caagaatgtt gagtatacag aaggggagga agccaaaaca tgctacaata    240
taagtgtaac ggatccctct ggaaaatcct tgctgttgga tcctcctacc aacatccgtg    300
actatcctaa atgcaaaact atccatcata ttcaaggtca aaccctcat gcgcaaggga    360
tcgccctcca tttgtgggga gcatttttcc tgtatgatcg cattgcctcc acaacaatgt    420
accgaggcag agtcttcact gaagggaaca tagcagctat gattgtcaat aagacagtgc    480
acaaaatgat tttctcgagg caaggacagg ggtaccgtca catgaatctg acttctacta    540
ataaatattg gacaagtaac aatggaacac aaacgaatga cactggatgc ttcggtgctc    600
ttcaagaata caactccacg aagaatcaaa catgtgctcc gtccaaaata ccctcaccac    660
tgcccacagc ccgtccagag atcaaaccca caagcacccc aactgatgcc accacactca    720
acaccacaga cccaaacaat gatgatgagg acctcataac atccggttca gggtccggag    780
aacaggaacc ctatacaact tcagatgcgg tcactaagca agggctttca tcaacaatgc    840
cacccactcc ctcaccacaa ccaagcacgc cacagcaaga aggaaacaac acagaccatt    900
cccaaggtac tgtgactgaa cccaacaaaa ccaacacaac ggcacaaccg tccatgcccc    960
cccacaacac cactgcaatc tctactaaca acacctccaa gaacaacttc agcaccctct   1020
ctgtatcact acaaaacacc accaattacg acacacagag cacagccact gaaaatgaac   1080
aaaccagtgc cccctcgaaa acaaccctgc ctccaacagg aaatcttacc acagcaaaga   1140
gcactaacaa cacgaaaggc cccaccacaa cggcaccaaa tatgacaaat gggcatttaa   1200
ccagtccctc ccccaccccc aacccgacca cacaacatct tgtatatttc agaaagaaac   1260
gaagtatcct ctggagggaa ggcgacatgt ttcctttttct ggacgggtta ataaatgctc   1320
caattgattt tgatccagtt ccaaatacaa agacgatctt tgatgaatct tctagttctg   1380
gtgcttcggc tgaggaagat caacatgcct cccccaatat cagtttaact ttatcctatt   1440
ttcctaatat aaatgaaaac actgcctact ctggagaaaa tgagaacgat tgtgatgcag   1500
agttaagaat ttggagcgtt caggaggatg acctggcagc agggctcagt tggataccgt   1560
tttttggccc tggaatcgaa ggactttata ctgctggttt aattaaaaac caaaacaatt   1620
tggtctgcag gttgaggcgt ctagccaatc aaactgccaa atccttggaa ctcttattaa   1680
gagtcacaac cgaggaaagg acattttcct taattaatag acatgccatt gactttctac   1740
tcacaaggtg gggaggaaca tgcaaagtgc ttggacctga ttgttgcatt ggaatagaag   1800
acttgtccag gaatatttcg gaacaaattg accaaatcaa aaaagatgaa caaaaagagg   1860
ggactggttg gggtctaggt ggtaaatggt ggacatccta gtaagtcgac aacct         1915
```

<210> SEQ ID NO 9
<211> LENGTH: 1898
<212> TYPE: DNA
<213> ORGANISM: Marburg Virus

<400> SEQUENCE: 9

```
aggttagatc tctccctatt ttagagatag ctagtaacaa tcaaccccaa aatgtggatt     60
cggtatgctc cggaactctc cagaagacag aagatgtcca tctgatggga ttcacactga    120
gtgggcaaaa agttgctgat tcccctttgg aggcatccaa gcgatgggct ttcaggacag    180
gtgtacctcc caagaatgtt gagtatacag aaggggagga agccaaaaca tgctacaata    240
```

```
taagtgtaac ggatccctct ggaaaatcct tgctgttgga tcctcctacc aacatccgtg    300

actatcctaa atgcaaaact atccatcata ttcaaggtca aaaccctcat gcgcaaggga    360

tcgccctcca tttgtgggga gcatttttcc tgtatgatcg cattgcctcc acaacaatgt    420

accgaggcag agtcttcact gaagggaaca tagcagctat gattgtcaat aagacagtgc    480

acaaaatgat tttctcgagg caaggacagg ggtaccgtca catgaatctg acttctacta    540

ataaatattg gacaagtaac aatggaacac aaacgaatga cactggatgc ttcggtgctc    600

ttcaagaata caactccacg aagaatcaaa catgtgctcc gtccaaaata ccctcaccac    660

tgcccacagc ccgtccagag atcaaaccca caagcacccc aactgatgcc accacactca    720

acaccacaga cccaaacaat gatgatgagg acctcataac atccggttca gggtccggag    780

aacaggaacc ctatacaact tcagatgcgg tcactaagca agggctttca tcaacaatgc    840

cacccactcc ctcaccacaa ccaagcacgc cacagcaaga aggaaacaac acagaccatt    900

cccaaggtac tgtgactgaa cccaacaaaa ccaacacaac ggcacaaccg tccatgcccc    960

cccacaacac cactgcaatc tctactaaca acacctccaa gaacaacttc agcaccctct   1020

ctgtatcact acaaaacacc accaattacg acacacagag cacagccact gaaaatgaac   1080

aaaccagtgc cccctcgaaa acaaccctgc ctccaacagg aaatcttacc acagcaaaga   1140

gcactaacaa cacgaaaggc cccaccacaa cggcaccaaa tatgacaaat gggcatttaa   1200

ccagtccctc ccccaccccc aacccgacca cacaacatct tgtatatttc agaaagaaac   1260

gaagtatcct ctggagggaa ggcgacatgt ttccttttct ggacgggtta ataaatgctc   1320

caattgattt tgatccagtt ccaaatacaa agacgatctt tgatgaatct tctagttctg   1380

gtgcttcggc tgaggaagat caacatgcct cccccaatat cagtttaact ttatcctatt   1440

ttcctaatat aaatgaaaac actgcctact ctggagaaaa tgagaacgat tgtgatgcag   1500

agttaagaat ttggagcgtt caggaggatg acctggcagc agggctcagt tggataccgt   1560

tttttggccc tggaatcgaa ggactttata ctgctggttt aattaaaaac caaaacaatt   1620

tggtctgcag gttgaggcgt ctagccaatc aaactgccaa atccttggaa ctcttattaa   1680

gagtcacaac cgaggaaagg acattttcct taattaatag acatgccatt gactttctac   1740

tcacaaggtg gggaggaaca tgcaaagtgc ttggacctga ttgttgcatt ggaatagaag   1800

acttgtccag gaatatttcg gaacaaattg accaaatcaa aaaagatgaa caaaaagagg   1860

ggactggttg ggtctaggt ggtaaatggt ggacatcc                            1898


<210> SEQ ID NO 10
<211> LENGTH: 646
<212> TYPE: PRT
<213> ORGANISM: Ebola Zaire Virus

<400> SEQUENCE: 10

Arg Ser Ile Pro Leu Gly Val Ile His Asn Ser Thr Leu Gln Val Ser
1               5                   10                  15

Asp Val Asp Lys Leu Val Cys Arg Asp Lys Leu Ser Ser Thr Asn Gln
            20                  25                  30

Leu Arg Ser Val Gly Leu Asn Leu Glu Gly Asn Gly Val Ala Thr Asp
        35                  40                  45

Val Pro Ser Ala Thr Lys Arg Trp Gly Phe Arg Ser Gly Val Pro Pro
    50                  55                  60

Lys Val Val Asn Tyr Glu Ala Gly Glu Trp Ala Glu Asn Cys Tyr Asn
65                  70                  75                  80
```

```
Leu Glu Ile Lys Lys Pro Asp Gly Ser Glu Cys Leu Pro Ala Ala Pro
                85                  90                  95

Asp Gly Ile Arg Gly Phe Pro Arg Cys Arg Tyr Val His Lys Val Ser
            100                 105                 110

Gly Thr Gly Pro Cys Ala Gly Asp Phe Ala Phe His Lys Glu Gly Ala
        115                 120                 125

Phe Phe Leu Tyr Asp Arg Leu Ala Ser Thr Val Ile Tyr Arg Gly Thr
    130                 135                 140

Thr Phe Ala Glu Gly Val Val Ala Phe Leu Ile Leu Pro Gln Ala Lys
145                 150                 155                 160

Lys Asp Phe Phe Ser Ser His Pro Leu Arg Glu Pro Val Asn Ala Thr
                165                 170                 175

Glu Asp Pro Ser Ser Gly Tyr Tyr Ser Thr Thr Ile Arg Tyr Gln Ala
            180                 185                 190

Thr Gly Phe Gly Thr Asn Glu Thr Glu Tyr Leu Phe Glu Val Asp Asn
        195                 200                 205

Leu Thr Tyr Val Gln Leu Glu Ser Arg Phe Thr Pro Gln Phe Leu Leu
    210                 215                 220

Gln Leu Asn Glu Thr Ile Tyr Thr Ser Gly Lys Arg Ser Asn Thr Thr
225                 230                 235                 240

Gly Lys Leu Ile Trp Lys Val Asn Pro Glu Ile Asp Thr Thr Ile Gly
                245                 250                 255

Glu Trp Ala Phe Trp Glu Thr Lys Lys Asn Leu Thr Arg Lys Ile Arg
            260                 265                 270

Ser Glu Glu Leu Ser Phe Thr Val Val Ser Asn Gly Ala Lys Asn Ile
        275                 280                 285

Ser Gly Gln Ser Pro Ala Arg Thr Ser Ser Asp Pro Gly Thr Asn Thr
    290                 295                 300

Thr Thr Glu Asp His Lys Ile Met Ala Ser Glu Asn Ser Ser Ala Met
305                 310                 315                 320

Val Gln Val His Ser Gln Gly Arg Glu Ala Ala Val Ser His Leu Thr
                325                 330                 335

Thr Leu Ala Thr Ile Ser Thr Ser Pro Gln Ser Leu Thr Thr Lys Pro
            340                 345                 350

Gly Pro Asp Asn Ser Thr His Asn Thr Pro Val Tyr Lys Leu Asp Ile
        355                 360                 365

Ser Glu Ala Thr Gln Val Glu Gln His His Arg Arg Thr Asp Asn Asp
    370                 375                 380

Ser Thr Ala Ser Asp Thr Pro Ser Ala Thr Thr Ala Ala Gly Pro Pro
385                 390                 395                 400

Lys Ala Glu Asn Thr Asn Thr Ser Lys Ser Thr Asp Phe Leu Asp Pro
                405                 410                 415

Ala Thr Thr Thr Ser Pro Gln Asn His Ser Glu Thr Ala Gly Asn Asn
            420                 425                 430

Asn Thr His His Gln Asp Thr Gly Glu Glu Ser Ala Ser Ser Gly Lys
        435                 440                 445

Leu Gly Leu Ile Thr Asn Thr Ile Ala Gly Val Ala Gly Leu Ile Thr
    450                 455                 460

Gly Gly Arg Arg Thr Arg Arg Glu Ala Ile Val Asn Ala Gln Pro Lys
465                 470                 475                 480

Cys Asn Pro Asn Leu His Tyr Trp Thr Thr Gln Asp Glu Gly Ala Ala
                485                 490                 495

Ile Gly Leu Ala Trp Ile Pro Tyr Phe Gly Pro Ala Ala Glu Gly Ile
            500                 505                 510
```

```
Tyr Thr Glu Gly Leu Met His Asn Gln Asp Gly Leu Ile Cys Gly Leu
        515                 520                 525

Arg Gln Leu Ala Asn Glu Thr Thr Gln Ala Leu Gln Leu Phe Leu Arg
    530                 535                 540

Ala Thr Thr Glu Leu Arg Thr Phe Ser Ile Leu Asn Arg Lys Ala Ile
545                 550                 555                 560

Asp Phe Leu Leu Gln Arg Trp Gly Gly Thr Cys His Ile Leu Gly Pro
                565                 570                 575

Asp Cys Cys Ile Glu Pro His Asp Trp Thr Lys Asn Ile Thr Asp Lys
            580                 585                 590

Ile Asp Gln Ile Ile His Asp Phe Val Asp Lys Thr Leu Pro Asp Gln
        595                 600                 605

Gly Asp Asn Asp Asn Trp Trp Thr Gly Trp Arg Gln Trp Ile Pro Ala
    610                 615                 620

Gly Ile Gly Val Thr Gly Val Ile Ile Ala Val Ile Ala Leu Phe Cys
625                 630                 635                 640

Ile Cys Lys Phe Val Phe
                645


<210> SEQ ID NO 11
<211> LENGTH: 1964
<212> TYPE: DNA
<213> ORGANISM: Ebola Zaire Virus

<400> SEQUENCE: 11

acgtacagat ctatcccact tggagtcatc cacaatagca cattacaggt tagtgatgtc      60

gacaaactag tttgtcgtga caaactgtca tccacaaatc aattgagatc agttggactg     120

aatctcgaag ggaatggagt ggcaactgac gtgccatctg caactaaaag atggggcttc     180

aggtccggtg tcccaccaaa ggtggtcaat tatgaagctg gtgaatgggc tgaaaactgc     240

tacaatcttg aaatcaaaaa acctgacggg agtgagtgtc taccagcagc gccagacggg     300

attcggggct tcccccggtg ccggtatgtg cacaaagtat caggaacggg accgtgtgcc     360

ggagactttg ccttccataa agagggtgct ttcttcctgt atgatcgact tgcttccaca     420

gttatctacc gaggaacgac tttcgctgaa ggtgtcgttg catttctgat actgccccaa     480

gctaagaagg acttcttcag ctcacacccc ttgagagagc cggtcaatgc aacggaggac     540

ccgtctagtg gctactattc taccacaatt agatatcagg ctaccggttt tggaaccaat     600

gagacagagt acttgttcga ggttgacaat ttgacctacg tccaacttga atcaagattc     660

acaccacagt ttctgctcca gctgaatgag acaatatata caagtgggaa aaggagcaat     720

accacgggaa aactaatttg gaaggtcaac cccgaaattg atacaacaat cggggagtgg     780

gccttctggg aaactaaaaa aaacctcact agaaaaattc gcagtgaaga gttgtctttc     840

acagttgtat caaacggagc caaaaacatc agtggtcaga gtccggcgcg aacttcttcc     900

gacccaggga ccaacacaac aactgaagac cacaaaatca tggcttcaga aaattcctct     960

gcaatggttc aagtgcacag tcaaggaagg gaagctgcag tgtcgcatct aacaaccctt    1020

gccacaatct ccacgagtcc ccaatccctc acaaccaaac caggtccgga caacagcacc    1080

cataatacac ccgtgtataa acttgacatc tctgaggcaa ctcaagttga acaacatcac    1140

cgcagaacag acaacgacag cacagcctcc gacactccct ctgccacgac cgcagccgga    1200

cccccaaaag cagagaacac caacacgagc aagagcactg acttcctgga ccccgccacc    1260

acaacaagtc cccaaaacca cagcgagacc gctggcaaca acaacactca tcaccaagat    1320
```

```
accggagaag agagtgccag cagcgggaag ctaggcttaa ttaccaatac tattgctgga   1380

gtcgcaggac tgatcacagg cgggagaaga actcgaagag aagcaattgt caatgctcaa   1440

cccaaatgca accctaattt acattactgg actactcagg atgaaggtgc tgcaatcgga   1500

ctggcctgga taccatattt cgggccagca gccgagggaa tttacacaga ggggctaatg   1560

cacaatcaag atggtttaat ctgtgggttg agacagctgg ccaacgagac gactcaagct   1620

cttcaactgt tcctgagagc cacaactgag ctacgcacct tttcaatcct caaccgtaag   1680

gcaattgatt tcttgctgca gcgatggggc ggcacatgcc acattctggg accggactgc   1740

tgtatcgaac cacatgattg gaccaagaac ataacagaca aaattgatca gattattcat   1800

gattttgttg ataaaaccct tccggaccag ggggacaatg acaattggtg gacaggatgg   1860

agacaatgga taccggcagg tattggagtt acaggcgtta taattgcagt tatcgcttta   1920

ttctgtatat gcaaatttgt cttttagtaa ctcgaggtac gtac                   1964
```

```
<210> SEQ ID NO 12
<211> LENGTH: 1932
<212> TYPE: DNA
<213> ORGANISM: Ebola Zaire Virus

<400> SEQUENCE: 12

atcccacttg gagtcatcca caatagcaca ttacaggtta gtgatgtcga caaactagtt     60

tgtcgtgaca aactgtcatc cacaaatcaa ttgagatcag ttggactgaa tctcgaaggg    120

aatggagtgg caactgacgt gccatctgca actaaaagat ggggcttcag gtccggtgtc    180

ccaccaaagg tggtcaatta tgaagctggt gaatgggctg aaaactgcta caatcttgaa    240

atcaaaaaac ctgacgggag tgagtgtcta ccagcagcgc cagacgggat tcggggcttc    300

ccccggtgcc ggtatgtgca caaagtatca ggaacgggac cgtgtgccgg agactttgcc    360

ttccataaag agggtgcttt cttcctgtat gatcgacttg cttccacagt tatctaccga    420

ggaacgactt tcgctgaagg tgtcgttgca tttctgatac tgccccaagc taagaaggac    480

ttcttcagct cacacccctt gagagagccg gtcaatgcaa cggaggaccc gtctagtggc    540

tactattcta ccacaattag atatcaggct accggttttg gaaccaatga gacagagtac    600

ttgttcgagg ttgacaattt gacctacgtc caacttgaat caagattcac accacagttt    660

ctgctccagc tgaatgagac aatatataca agtgggaaaa ggagcaatac cacgggaaaa    720

ctaatttgga aggtcaaccc cgaaattgat acaacaatcg gggagtgggc cttctgggaa    780

actaaaaaaa acctcactag aaaaattcgc agtgaagagt tgtctttcac agttgtatca    840

aacggagcca aaaacatcag tggtcagagt ccggcgcgaa cttcttccga cccagggacc    900

aacacaacaa ctgaagacca caaaatcatg gcttcagaaa attcctctgc aatggttcaa    960

gtgcacagtc aaggaaggga agctgcagtg tcgcatctaa caacccttgc cacaatctcc   1020

acgagtcccc aatccctcac aaccaaacca ggtccggaca acagcaccca taatacaccc   1080

gtgtataaac ttgacatctc tgaggcaact caagttgaac aacatcaccg cagaacagac   1140

aacgacagca cagcctccga cactccctct gccacgaccg cagccggacc cccaaaagca   1200

gagaacacca acacgagcaa gagcactgac ttcctggacc ccgccaccac aacaagtccc   1260

caaaaccaca gcgagaccgc tggcaacaac aacactcatc accaagatac cggagaagag   1320

agtgccagca gcgggaagct aggcttaatt accaatacta ttgctggagt cgcaggactg   1380

atcacaggcg ggagaagaac tcgaagagaa gcaattgtca atgctcaacc caaatgcaac   1440

cctaatttac attactggac tactcaggat gaaggtgctg caatcggact ggcctggata   1500
```

```
ccatatttcg ggccagcagc cgagggaatt tacacagagg ggctaatgca caatcaagat   1560

ggtttaatct gtgggttgag acagctggcc aacgagacga ctcaagctct tcaactgttc   1620

ctgagagcca caactgagct acgcaccttt tcaatcctca accgtaaggc aattgatttc   1680

ttgctgcagc gatggggcgg cacatgccac attctgggac cggactgctg tatcgaacca   1740

catgattgga ccaagaacat aacagacaaa attgatcaga ttattcatga ttttgttgat   1800

aaaacccttc cggaccaggg ggacaatgac aattggtgga caggatggag acaatggata   1860

ccggcaggta ttggagttac aggcgttata attgcagtta tcgctttatt ctgtatatgc   1920

aaatttgtct tt                                                         1932


<210> SEQ ID NO 13
<211> LENGTH: 328
<212> TYPE: PRT
<213> ORGANISM: Ebola Zaire Virus

<400> SEQUENCE: 13

Arg Ser Met Arg Arg Val Ile Leu Pro Thr Ala Pro Pro Glu Tyr Met
1               5                   10                  15

Glu Ala Ile Tyr Pro Val Arg Ser Asn Ser Thr Ile Ala Arg Gly Gly
            20                  25                  30

Asn Ser Asn Thr Gly Phe Leu Thr Pro Glu Ser Val Asn Gly Asp Thr
        35                  40                  45

Pro Ser Asn Pro Leu Arg Pro Ile Ala Asp Asp Thr Ile Asp His Ala
    50                  55                  60

Ser His Thr Pro Gly Ser Val Ser Ser Ala Phe Ile Leu Glu Ala Met
65                  70                  75                  80

Val Asn Val Ile Ser Gly Pro Lys Val Leu Met Lys Gln Ile Pro Ile
                85                  90                  95

Trp Leu Pro Leu Gly Val Ala Asp Gln Lys Thr Tyr Ser Phe Asp Ser
            100                 105                 110

Thr Thr Ala Ala Ile Met Leu Ala Ser Tyr Thr Ile Thr His Phe Gly
        115                 120                 125

Lys Ala Thr Asn Pro Leu Val Arg Val Asn Arg Leu Gly Pro Gly Ile
    130                 135                 140

Pro Asp His Pro Leu Arg Leu Leu Arg Ile Gly Asn Gln Ala Phe Leu
145                 150                 155                 160

Gln Glu Phe Val Leu Pro Pro Val Gln Leu Pro Gln Tyr Phe Thr Phe
                165                 170                 175

Asp Leu Thr Ala Leu Lys Leu Ile Thr Gln Pro Leu Pro Ala Ala Thr
            180                 185                 190

Trp Thr Asp Asp Thr Pro Thr Gly Ser Asn Gly Ala Leu Arg Pro Gly
        195                 200                 205

Ile Ser Phe His Pro Lys Leu Arg Pro Ile Leu Leu Pro Asn Lys Ser
    210                 215                 220

Gly Lys Lys Gly Asn Ser Ala Asp Leu Thr Ser Pro Glu Lys Ile Gln
225                 230                 235                 240

Ala Ile Met Thr Ser Leu Gln Asp Phe Lys Ile Val Pro Ile Asp Pro
                245                 250                 255

Thr Lys Asn Ile Met Gly Ile Glu Val Pro Glu Thr Leu Val His Lys
            260                 265                 270

Leu Thr Gly Lys Lys Val Thr Ser Lys Asn Gly Gln Pro Ile Ile Pro
        275                 280                 285

Val Leu Leu Pro Lys Tyr Ile Gly Leu Asp Pro Val Ala Pro Gly Asp
    290                 295                 300
```

```
Leu Thr Met Val Ile Thr Gln Asp Cys Asp Thr Cys His Ser Pro Ala
305                 310                 315                 320

Ser Leu Pro Ala Val Ile Glu Lys
                325


<210> SEQ ID NO 14
<211> LENGTH: 1008
<212> TYPE: DNA
<213> ORGANISM: Ebola Zaire Virus

<400> SEQUENCE: 14

acgtacagat ctatgaggcg ggttatattg cctactgctc ctcctgaata tatggaggcc     60

atatacccctg tcaggtcaaa ttcaacaatt gctagaggtg gcaacagcaa tacaggcttc    120

ctgacaccgg agtcagtcaa tggggacact ccatcgaatc cactcaggcc aattgccgat    180

gacaccatcg accatgccag ccacacacca ggcagtgtgt catcagcatt catccttgaa    240

gctatggtga atgtcatatc gggccccaaa gtgctaatga agcaaattcc aatttggctt    300

cctctaggtg tcgctgatca aaagacctac agctttgact caactacggc cgccatcatg    360

cttgcttcat acactatcac ccatttcggc aaggcaacca atccacttgt cagagtcaat    420

cggctgggtc ctggaatccc ggatcatccc ctcaggctcc tgcgaattgg aaaccaggct    480

ttcctccagg agttcgttct tccgccagtc caactacccc agtatttcac ctttgatttg    540

acagcactca aactgatcac ccaaccactg cctgctgcaa catggaccga tgacactcca    600

acaggatcaa atggagcgtt gcgtccagga atttcatttc atccaaaact tcgccccatt    660

cttttaccca acaaaagtgg gaagaagggg aacagtgccg atctaacatc tccggagaaa    720

atccaagcaa taatgacttc actccaggac ttcaagatcg ttccaattga tccaaccaaa    780

aatatcatgg gaatcgaagt gccagaaact ctggtccaca agctgaccgg taagaaggtg    840

acttctaaaa atggacaacc aatcatccct gttcttttgc caaagtacat tgggttggac    900

ccggtggctc caggagacct caccatggta atcacacagg attgtgacac gtgtcattct    960

cctgcaagtc ttccagctgt gattgagaag taataactcg aggtacgt                1008


<210> SEQ ID NO 15
<211> LENGTH: 978
<212> TYPE: DNA
<213> ORGANISM: Ebola Zaire Virus

<400> SEQUENCE: 15

atgaggcggg ttatattgcc tactgctcct cctgaatata tggaggccat ataccctgtc     60

aggtcaaatt caacaattgc tagaggtggc aacagcaata caggcttcct gacaccggag    120

tcagtcaatg gggacactcc atcgaatcca ctcaggccaa ttgccgatga caccatcgac    180

catgccagcc acacaccagg cagtgtgtca tcagcattca tccttgaagc tatggtgaat    240

gtcatatcgg gccccaaagt gctaatgaag caaattccaa tttggcttcc tctaggtgtc    300

gctgatcaaa agacctacag ctttgactca actacggccg ccatcatgct tgcttcatac    360

actatcaccc atttcggcaa ggcaaccaat ccacttgtca gagtcaatcg gctgggtcct    420

ggaatcccgg atcatcccct caggctcctg cgaattggaa accaggcttt cctccaggag    480

ttcgttcttc cgccagtcca actaccccag tatttcacct ttgatttgac agcactcaaa    540

ctgatcaccc aaccactgcc tgctgcaaca tggaccgatg acactccaac aggatcaaat    600

ggagcgttgc gtccaggaat ttcatttcat ccaaaacttc gccccattct tttacccaac    660

aaaagtggga agaaggggaa cagtgccgat ctaacatctc cggagaaaat ccaagcaata    720
```

```
atgacttcac tccaggactt caagatcgtt ccaattgatc caaccaaaaa tatcatggga    780

atcgaagtgc cagaaactct ggtccacaag ctgaccggta agaaggtgac ttctaaaaat    840

ggacaaccaa tcatccctgt tcttttgcca aagtacattg ggttggaccc ggtggctcca    900

ggagacctca ccatggtaat cacacaggat tgtgacacgt gtcattctcc tgcaagtctt    960

ccagctgtga ttgagaag                                                  978


<210> SEQ ID NO 16
<211> LENGTH: 253
<212> TYPE: PRT
<213> ORGANISM: Ebola Zaire Virus

<400> SEQUENCE: 16

Arg Ser Met Ala Lys Ala Thr Gly Arg Tyr Asn Leu Ile Ser Pro Lys
1               5                   10                  15

Lys Asp Leu Glu Lys Gly Val Val Leu Ser Asp Leu Cys Asn Phe Leu
            20                  25                  30

Val Ser Gln Thr Ile Gln Gly Trp Lys Val Tyr Trp Ala Gly Ile Glu
        35                  40                  45

Phe Asp Val Thr His Lys Gly Met Ala Leu Leu His Arg Leu Lys Thr
    50                  55                  60

Asn Asp Phe Ala Pro Ala Trp Ser Met Thr Arg Asn Leu Phe Pro His
65                  70                  75                  80

Leu Phe Gln Asn Pro Asn Ser Thr Ile Glu Ser Pro Leu Trp Ala Leu
                85                  90                  95

Arg Val Ile Leu Ala Ala Gly Ile Gln Asp Gln Leu Ile Asp Gln Ser
            100                 105                 110

Leu Ile Glu Pro Leu Ala Gly Ala Leu Gly Leu Ile Ser Asp Trp Leu
        115                 120                 125

Leu Thr Thr Asn Thr Asn His Phe Asn Met Arg Thr Gln Arg Val Lys
    130                 135                 140

Glu Gln Leu Ser Leu Lys Met Leu Ser Leu Ile Arg Ser Asn Ile Leu
145                 150                 155                 160

Lys Phe Ile Asn Lys Leu Asp Ala Leu His Val Val Asn Tyr Asn Gly
                165                 170                 175

Leu Leu Ser Ser Ile Glu Ile Gly Thr Gln Asn His Thr Ile Ile Ile
            180                 185                 190

Thr Arg Thr Asn Met Gly Phe Leu Val Glu Leu Gln Glu Pro Asp Lys
        195                 200                 205

Ser Ala Met Asn Arg Met Lys Pro Gly Pro Ala Lys Phe Ser Leu Leu
    210                 215                 220

His Glu Ser Thr Leu Lys Ala Phe Thr Gln Gly Ser Ser Thr Arg Met
225                 230                 235                 240

Gln Ser Leu Ile Leu Glu Phe Asn Ser Ser Leu Ala Ile
                245                 250


<210> SEQ ID NO 17
<211> LENGTH: 783
<212> TYPE: DNA
<213> ORGANISM: Ebola Zaire Virus

<400> SEQUENCE: 17

acgtacagat ctatggctaa agctacggga cgatacaatc taatatcgcc caaaaaggac     60

ctggagaaag gggttgtctt aagcgacctc tgtaacttct tagttagcca aactattcag    120

gggtggaagg tttattgggc tggtattgag tttgatgtga ctcacaaagg aatggcccta    180
```

```
ttgcatagac tgaaaactaa tgactttgcc cctgcatggt caatgacaag gaatctcttt    240

cctcatttat ttcaaaatcc gaattccaca attgaatcac cgctgtgggc attgagagtc    300

atccttgcag cagggataca ggaccagctg attgaccagt ctttgattga acccttagca    360

ggagcccttg gtctgatctc tgattggctg ctaacaacca acactaacca tttcaacatg    420

cgaacacaac gtgtcaagga acaattgagc ctaaaaatgc tgtcgttgat tcgatccaat    480

attctcaagt ttattaacaa attggatgct ctacatgtcg tgaactacaa cggattgttg    540

agcagtattg aaattggaac tcaaaatcat acaatcatca taactcgaac taacatgggt    600

tttctggtgg agctccaaga acccgacaaa tcggcaatga accgcatgaa gcctgggccg    660

gcgaaatttt ccctccttca tgagtccaca ctgaaagcat ttacacaagg atcctcgaca    720

cgaatgcaaa gtttgattct tgaatttaat agctctcttg ctatctaata actcgaggta    780

cgt                                                                  783
```

<210> SEQ ID NO 18
<211> LENGTH: 753
<212> TYPE: DNA
<213> ORGANISM: Ebola Zaire Virus

<400> SEQUENCE: 18

```
atggctaaag ctacgggacg atacaatcta atatcgccca aaaaggacct ggagaaaggg     60

gttgtcttaa gcgacctctg taacttctta gttagccaaa ctattcaggg gtggaaggtt    120

tattgggctg gtattgagtt tgatgtgact cacaaaggaa tggccctatt gcatagactg    180

aaaactaatg actttgcccc tgcatggtca atgacaagga atctctttcc tcatttattt    240

caaaatccga attccacaat tgaatcaccg ctgtgggcat tgagagtcat ccttgcagca    300

gggatacagg accagctgat tgaccagtct ttgattgaac ccttagcagg agcccttggt    360

ctgatctctg attggctgct aacaaccaac actaaccatt tcaacatgcg aacacaacgt    420

gtcaaggaac aattgagcct aaaaatgctg tcgttgattc gatccaatat tctcaagttt    480

attaacaaat tggatgctct acatgtcgtg aactacaacg gattgttgag cagtattgaa    540

attggaactc aaaatcatac aatcatcata actcgaacta acatgggttt tctggtggag    600

ctccaagaac ccgacaaatc ggcaatgaac cgcatgaagc ctgggccggc gaaattttcc    660

ctccttcatg agtccacact gaaagcattt acacaaggat cctcgacacg aatgcaaagt    720

ttgattcttg aatttaatag ctctcttgct atc                                 753
```

<210> SEQ ID NO 19
<211> LENGTH: 741
<212> TYPE: PRT
<213> ORGANISM: Ebola Zaire Virus

<400> SEQUENCE: 19

```
Arg Ser Met Asp Ser Arg Pro Gln Lys Ile Trp Met Ala Pro Ser Leu
1               5                   10                  15

Thr Glu Ser Asp Met Asp Tyr His Lys Ile Leu Thr Ala Gly Leu Ser
            20                  25                  30

Val Gln Gln Gly Ile Val Arg Gln Arg Val Ile Pro Val Tyr Gln Val
        35                  40                  45

Asn Asn Leu Glu Glu Ile Cys Gln Leu Ile Ile Gln Ala Phe Glu Ala
    50                  55                  60

Gly Val Asp Phe Gln Glu Ser Ala Asp Ser Phe Leu Leu Met Leu Cys
65                  70                  75                  80
```

```
Leu His His Ala Tyr Gln Gly Asp Tyr Lys Leu Phe Leu Glu Ser Gly
                85                  90                  95

Ala Val Lys Tyr Leu Glu Gly His Gly Phe Arg Phe Glu Val Lys Lys
            100                 105                 110

Arg Asp Gly Val Lys Arg Leu Glu Glu Leu Leu Pro Ala Val Ser Ser
        115                 120                 125

Gly Lys Asn Ile Lys Arg Thr Leu Ala Ala Met Pro Glu Glu Glu Thr
    130                 135                 140

Thr Glu Ala Asn Ala Gly Gln Phe Leu Ser Phe Ala Ser Leu Phe Leu
145                 150                 155                 160

Pro Lys Leu Val Val Gly Glu Lys Ala Cys Leu Glu Lys Val Gln Arg
                165                 170                 175

Gln Ile Gln Val His Ala Glu Gln Gly Leu Ile Gln Tyr Pro Thr Ala
            180                 185                 190

Trp Gln Ser Val Gly His Met Met Val Ile Phe Arg Leu Met Arg Thr
        195                 200                 205

Asn Phe Leu Ile Lys Phe Leu Leu Ile His Gln Gly Met His Met Val
    210                 215                 220

Ala Gly His Asp Ala Asn Asp Ala Val Ile Ser Asn Ser Val Ala Gln
225                 230                 235                 240

Ala Arg Phe Ser Gly Leu Leu Ile Val Lys Thr Val Leu Asp His Ile
                245                 250                 255

Leu Gln Lys Thr Glu Arg Gly Val Arg Leu His Pro Leu Ala Arg Thr
            260                 265                 270

Ala Lys Val Lys Asn Glu Val Asn Ser Phe Lys Ala Ala Leu Ser Ser
        275                 280                 285

Leu Ala Lys His Gly Glu Tyr Ala Pro Phe Ala Arg Leu Leu Asn Leu
    290                 295                 300

Ser Gly Val Asn Asn Leu Glu His Gly Leu Phe Pro Gln Leu Ser Ala
305                 310                 315                 320

Ile Ala Leu Gly Val Ala Thr Ala His Gly Ser Thr Leu Ala Gly Val
                325                 330                 335

Asn Val Gly Glu Gln Tyr Gln Gln Leu Arg Glu Ala Ala Thr Glu Ala
            340                 345                 350

Glu Lys Gln Leu Gln Gln Tyr Ala Glu Ser Arg Glu Leu Asp His Leu
        355                 360                 365

Gly Leu Asp Asp Gln Glu Lys Lys Ile Leu Met Asn Phe His Gln Lys
    370                 375                 380

Lys Asn Glu Ile Ser Phe Gln Gln Thr Asn Ala Met Val Thr Leu Arg
385                 390                 395                 400

Lys Glu Arg Leu Ala Lys Leu Thr Glu Ala Ile Thr Ala Ala Ser Leu
                405                 410                 415

Pro Lys Thr Ser Gly His Tyr Asp Asp Asp Asp Asp Ile Pro Phe Pro
            420                 425                 430

Gly Pro Ile Asn Asp Asp Asp Asn Pro Gly His Gln Asp Asp Asp Pro
        435                 440                 445

Thr Asp Ser Gln Asp Thr Thr Ile Pro Asp Val Val Val Asp Pro Asp
    450                 455                 460

Asp Gly Ser Tyr Gly Glu Tyr Gln Ser Tyr Ser Glu Asn Gly Met Asn
465                 470                 475                 480

Ala Pro Asp Asp Leu Val Leu Phe Asp Leu Asp Glu Asp Asp Glu Asp
                485                 490                 495

Thr Lys Pro Val Pro Asn Arg Ser Thr Lys Gly Gly Gln Gln Lys Asn
            500                 505                 510
```

```
Ser Gln Lys Gly Gln His Ile Glu Gly Arg Gln Thr Gln Ser Arg Pro
        515                 520                 525

Ile Gln Asn Val Pro Gly Pro His Arg Thr Ile His His Ala Ser Ala
    530                 535                 540

Pro Leu Thr Asp Asn Asp Arg Arg Asn Glu Pro Ser Gly Ser Thr Ser
545                 550                 555                 560

Pro Arg Met Leu Thr Pro Ile Asn Glu Glu Ala Asp Pro Leu Asp Asp
                565                 570                 575

Ala Asp Asp Glu Thr Ser Ser Leu Pro Pro Leu Glu Ser Asp Asp Glu
            580                 585                 590

Glu Gln Asp Arg Asp Gly Thr Ser Asn Arg Thr Pro Thr Val Ala Pro
        595                 600                 605

Pro Ala Pro Val Tyr Arg Asp His Ser Glu Lys Lys Glu Leu Pro Gln
    610                 615                 620

Asp Glu Gln Gln Asp Gln Asp His Thr Gln Glu Ala Arg Asn Gln Asp
625                 630                 635                 640

Ser Asp Asn Thr Gln Ser Glu His Ser Phe Glu Glu Met Tyr Arg His
                645                 650                 655

Ile Leu Arg Ser Gln Gly Pro Phe Asp Ala Val Leu Tyr Tyr His Met
            660                 665                 670

Met Lys Asp Glu Pro Val Val Phe Ser Thr Ser Asp Gly Lys Glu Tyr
        675                 680                 685

Thr Tyr Pro Asp Ser Leu Glu Glu Glu Tyr Pro Pro Trp Leu Thr Glu
    690                 695                 700

Lys Glu Ala Met Asn Glu Glu Asn Arg Phe Val Thr Leu Asp Gly Gln
705                 710                 715                 720

Gln Phe Tyr Trp Pro Val Met Asn His Lys Asn Lys Phe Met Ala Ile
                725                 730                 735

Leu Gln His His Gln
            740


<210> SEQ ID NO 20
<211> LENGTH: 2247
<212> TYPE: DNA
<213> ORGANISM: Ebola Zaire Virus

<400> SEQUENCE: 20

atgctaggat ccatggattc tcgtcctcag aaaatctgga tggcgccgag tctcactgaa      60

tctgacatgg attaccacaa gatcttgaca gcaggtctgt ccgttcaaca ggggattgtt     120

cggcaaagag tcatcccagt gtatcaagta aacaatcttg aagaaatttg ccaacttatc     180

atacaggcct ttgaagcagg tgttgatttt caagagagtg cggacagttt ccttctcatg     240

ctttgtcttc atcatgcgta ccagggagat tacaaacttt tcttggaaag tggcgcagtc     300

aagtatttgg aagggcacgg gttccgtttt gaagtcaaga agcgtgatgg agtgaagcgc     360

cttgaggaat tgctgccagc agtatctagt ggaaaaaaca ttaagagaac acttgctgcc     420

atgccggaag aggagacaac tgaagctaat gccggtcagt ttctctcctt tgcaagtcta     480

ttccttccga aattggtagt aggagaaaag gcttgccttg agaaggttca aaggcaaatt     540

caagtacatg cagagcaagg actgatacaa tatccaacag cttggcaatc agtaggacac     600

atgatggtga ttttccgttt gatgcgaaca aattttctga tcaaatttct cctaatacac     660

caagggatgc acatggttgc cgggcatgat gccaacgatg ctgtgatttc aaattcagtg     720

gctcaagctc gtttttcagg cttattgatt gtcaaaacag tacttgatca tatcctacaa     780
```

```
aagacagaac gaggagttcg tctccatcct cttgcaagga ccgccaaggt aaaaaatgag    840

gtgaactcct ttaaggctgc actcagctcc ctggccaagc atggagagta tgctcctttc    900

gcccgacttt tgaacctttc tggagtaaat aatcttgagc atggtctttt ccctcaacta    960

tcggcaattg cactcggagt cgccacagca cacgggagta ccctcgcagg agtaaatgtt   1020

ggagaacagt atcaacaact cagagaggct gccactgagg ctgagaagca actccaacaa   1080

tatgcagagt ctcgcgaact tgaccatctt ggacttgatg atcaggaaaa gaaaattctt   1140

atgaacttcc atcagaaaaa gaacgaaatc agcttccagc aaacaaacgc tatggtaact   1200

ctaagaaaag agcgcctggc caagctgaca gaagctatca ctgctgcgtc actgcccaaa   1260

acaagtggac attacgatga tgatgacgac attccctttc caggacccat caatgatgac   1320

gacaatcctg gccatcaaga tgatgatccg actgactcac aggatacgac cattcccgat   1380

gtggtggttg atcccgatga tggaagctac ggcgaatacc agagttactc ggaaaacggc   1440

atgaatgcac cagatgactt ggtcctattc gatctagacg aggacgacga ggacactaag   1500

ccagtgccta atagatcgac caagggtgga caacagaaga acagtcaaaa gggccagcat   1560

atagagggca gacagacaca atccaggcca attcaaaatg tcccaggccc tcacagaaca   1620

atccaccacg ccagtgcgcc actcacggac aatgacagaa gaaatgaacc ctccggctca   1680

accagccctc gcatgctgac accaattaac gaagaggcag acccactgga cgatgccgac   1740

gacgagacgt ctagccttcc gcccttggag tcagatgatg aagagcagga cagggacgga   1800

acttccaacc gcacacccac tgtcgcccca ccggctcccg tatacagaga tcactctgaa   1860

aagaaagaac tcccgcaaga cgagcaacaa gatcaggacc acactcaaga ggccaggaac   1920

caggacagtg acaacaccca gtcagaacac tcttttgagg agatgtatcg ccacattcta   1980

agatcacagg ggccatttga tgctgttttg tattatcata tgatgaagga tgagcctgta   2040

gttttcagta ccagtgatgg caaagagtac acgtatccag actcccttga agaggaatat   2100

ccaccatggc tcactgaaaa agaggctatg aatgaagaga atagatttgt tacattggat   2160

ggtcaacaat tttattggcc ggtgatgaat cacaagaata aattcatggc aatcctgcaa   2220

catcatcagt gataactcga ggtacgt                                       2247
```

<210> SEQ ID NO 21
<211> LENGTH: 2217
<212> TYPE: DNA
<213> ORGANISM: Ebola Zaire Virus

<400> SEQUENCE: 21

```
atggattctc gtcctcagaa aatctggatg gcgccgagtc tcactgaatc tgacatggat     60

taccacaaga tcttgacagc aggtctgtcc gttcaacagg ggattgttcg gcaaagagtc    120

atcccagtgt atcaagtaaa caatcttgaa gaaatttgcc aacttatcat acaggccttt    180

gaagcaggtg ttgattttca agagagtgcg gacagtttcc ttctcatgct ttgtcttcat    240

catgcgtacc agggagatta caaacttttc ttggaaagtg gcgcagtcaa gtatttggaa    300

gggcacgggt tccgttttga agtcaagaag cgtgatggag tgaagcgcct tgaggaattg    360

ctgccagcag tatctagtgg aaaaaacatt aagagaacac ttgctgccat gccggaagag    420

gagacaactg aagctaatgc cggtcagttt ctctcctttg caagtctatt ccttccgaaa    480

ttggtagtag gagaaaaggc ttgccttgag aaggttcaaa ggcaaattca agtacatgca    540

gagcaaggac tgatacaata tccaacagct tggcaatcag taggacacat gatggtgatt    600

ttccgtttga tgcgaacaaa ttttctgatc aaatttctcc taatacacca agggatgcac    660
```

-continued

```
atggttgccg ggcatgatgc caacgatgct gtgatttcaa attcagtggc tcaagctcgt    720
ttttcaggct tattgattgt caaaacagta cttgatcata tcctacaaaa gacagaacga    780
ggagttcgtc tccatcctct tgcaaggacc gccaaggtaa aaaatgaggt gaactccttt    840
aaggctgcac tcagctccct ggccaagcat ggagagtatg ctcctttcgc ccgacttttg    900
aacctttctg gagtaaataa tcttgagcat ggtcttttcc ctcaactatc ggcaattgca    960
ctcggagtcg ccacagcaca cgggagtacc ctcgcaggag taaatgttgg agaacagtat   1020
caacaactca gagaggctgc cactgaggct gagaagcaac tccaacaata tgcagagtct   1080
cgcgaacttg accatcttgg acttgatgat caggaaaaga aaattcttat gaacttccat   1140
cagaaaaaga acgaaatcag cttccagcaa acaaacgcta tggtaactct aagaaaagag   1200
cgcctggcca agctgacaga agctatcact gctgcgtcac tgcccaaaac aagtggacat   1260
tacgatgatg atgacgacat tccctttcca ggacccatca atgatgacga caatcctggc   1320
catcaagatg atgatccgac tgactcacag gatacgacca ttcccgatgt ggtggttgat   1380
cccgatgatg gaagctacgg cgaataccag agttactcgg aaaacggcat gaatgcacca   1440
gatgacttgg tcctattcga tctagacgag gacgacgagg acactaagcc agtgcctaat   1500
agatcgacca agggtggaca acagaagaac agtcaaaagg gccagcatat agagggcaga   1560
cagacacaat ccaggccaat tcaaaatgtc ccaggccctc acagaacaat ccaccacgcc   1620
agtgcgccac tcacggacaa tgacagaaga aatgaaccct ccggctcaac cagccctcgc   1680
atgctgacac caattaacga agaggcagac ccactggacg atgccgacga cgagacgtct   1740
agccttccgc ccttggagtc agatgatgaa gagcaggaca gggacggaac ttccaaccgc   1800
acacccactg tcgccccacc ggctcccgta tacagagatc actctgaaaa gaaagaactc   1860
ccgcaagacg agcaacaaga tcaggaccac actcaagagg ccaggaacca ggacagtgac   1920
aacacccagt cagaacactc ttttgaggag atgtatcgcc acattctaag atcacagggg   1980
ccatttgatg ctgttttgta ttatcatatg atgaaggatg agcctgtagt tttcagtacc   2040
agtgatggca aagagtacac gtatccagac tcccttgaag aggaatatcc accatggctc   2100
actgaaaaag aggctatgaa tgaagagaat agatttgtta cattggatgg tcaacaattt   2160
tattggccgg tgatgaatca caagaataaa ttcatggcaa tcctgcaaca tcatcag      2217
```